(12) United States Patent
Lira et al.

(10) Patent No.: US 8,715,261 B2
(45) Date of Patent: May 6, 2014

(54) ABSORBENT ARTICLE HAVING LINE OF WEAKNESS FOR FOLDING THE ARTICLE

(75) Inventors: Carmen Lira, Appleton, WI (US); Adrienne Rae Loyd, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 146 days.

(21) Appl. No.: 13/423,400

(22) Filed: Mar. 19, 2012

(65) Prior Publication Data

US 2012/0215195 A1    Aug. 23, 2012

Related U.S. Application Data

(62) Division of application No. 12/335,316, filed on Dec. 15, 2008, now Pat. No. 8,157,780.

(51) Int. Cl.
*A61F 13/15* (2006.01)

(52) U.S. Cl.
USPC .................................. 604/385.201; 604/383

(58) Field of Classification Search
USPC ..................... 604/385.101, 385.201; 162/111
See application file for complete search history.

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 4,067,336 A | 1/1978 | Johnson | |
| 4,072,151 A | 2/1978 | Levine | |
| 4,340,563 A | 7/1982 | Appel et al. | |
| 4,488,928 A | 12/1984 | Ali Khan et al. | |
| 4,505,976 A | 3/1985 | Doehnert et al. | |
| 4,631,062 A | 12/1986 | Lassen et al. | |
| 4,673,403 A | 6/1987 | Lassen et al. | |
| 4,743,245 A | 5/1988 | Lassen et al. | |
| 4,798,603 A | 1/1989 | Meyer et al. | |

(Continued)

FOREIGN PATENT DOCUMENTS

| | | |
|---|---|---|
| DE | 69232589 | 12/2002 |
| EP | 0638303 | 2/1995 |

(Continued)

OTHER PUBLICATIONS

Lloyd et al., Female Genital Appearance: 'Normality' Unfolds; BJOB: An International Journal of Obstetrics and Gynecology; 2005; pp. 643-646; vol. 112.

(Continued)

*Primary Examiner* — Melanie Hand
(74) *Attorney, Agent, or Firm* — Armstrong Teasdale LLP

(57) ABSTRACT

A feminine care absorbent article has a longitudinal axis, a transverse axis, and an absorbent structure configured for disposition adjacent a female wearer's vaginal region to absorb bodily fluids discharged by the wearer. The absorbent structure has end portions and a middle portion located between the end portions. The absorbent structure has at least one line of weakness disposed in one of the end portions and configured to facilitate folding of the absorbent structure in a longitudinal direction in response to a lateral compressive force. The absorbent structure has a relief for inhibiting the longitudinal folding of the absorbent structure facilitated by the at least one line of weakness from extending beyond the middle portion of the absorbent structure.

18 Claims, 57 Drawing Sheets

(56) References Cited

U.S. PATENT DOCUMENTS

| | | | |
|---|---|---|---|
| 4,804,380 | A | 2/1989 | Lassen et al. |
| 4,846,824 | A | 7/1989 | Lassen et al. |
| 5,114,419 | A | 5/1992 | Daniel et al. |
| 5,147,938 | A | 9/1992 | Kuller |
| 5,194,550 | A | 3/1993 | Rance et al. |
| 5,221,275 | A | 6/1993 | Van Iten |
| 5,382,400 | A | 1/1995 | Pike et al. |
| 5,387,208 | A | 2/1995 | Ashton et al. |
| 5,445,627 | A | 8/1995 | Mizutani et al. |
| H1602 | H | 10/1996 | Brock |
| 5,611,790 | A | 3/1997 | Osborn, III et al. |
| 5,618,281 | A | 4/1997 | Betrabet et al. |
| 5,618,282 | A | 4/1997 | Schlangen |
| 5,658,270 | A | 8/1997 | Lichstein |
| 5,662,633 | A | 9/1997 | Doak et al. |
| 5,706,950 | A | 1/1998 | Houghton et al. |
| 5,759,560 | A | 6/1998 | Dillon |
| 5,800,417 | A | 9/1998 | Goerg-wood et al. |
| 5,807,367 | A | 9/1998 | Dilnik et al. |
| 5,830,202 | A | 11/1998 | Bogdanski et al. |
| 5,910,125 | A | 6/1999 | Cummings et al. |
| 5,994,613 | A | 11/1999 | Cummings et al. |
| 6,045,900 | A | 4/2000 | Haffner et al. |
| 6,156,818 | A | 12/2000 | Corzani et al. |
| 6,177,482 | B1 | 1/2001 | Cinelli et al. |
| 6,187,989 | B1 | 2/2001 | Corzani et al. |
| 6,191,189 | B1 | 2/2001 | Cinelli et al. |
| 6,211,263 | B1 | 4/2001 | Cinelli et al. |
| 6,213,993 | B1 | 4/2001 | Zacharias et al. |
| 6,255,552 | B1 | 7/2001 | Cummings et al. |
| 6,316,524 | B1 | 11/2001 | Corzani et al. |
| 6,336,935 | B1 | 1/2002 | Davis et al. |
| 6,362,389 | B1 | 3/2002 | McDowall et al. |
| 6,365,645 | B1 | 4/2002 | Cinelli et al. |
| 6,369,126 | B1 | 4/2002 | Cinelli et al. |
| 6,582,411 | B1 | 6/2003 | Carstens et al. |
| 6,617,490 | B1 | 9/2003 | Chen et al. |
| 6,620,143 | B1 | 9/2003 | Zacharias et al. |
| 6,632,210 | B1 | 10/2003 | Glasgow et al. |
| 6,641,569 | B1 | 11/2003 | Coles et al. |
| 6,657,095 | B2 | 12/2003 | Zhou |
| 6,670,402 | B1 | 12/2003 | Lee et al. |
| 6,997,915 | B2 | 2/2006 | Gell et al. |
| 7,033,342 | B2 | 4/2006 | Mizutani et al. |
| 7,045,559 | B2 | 5/2006 | Yahiaoui et al. |
| 7,053,131 | B2 | 5/2006 | Ko et al. |
| 7,122,022 | B2 | 10/2006 | Drevik |
| 7,125,401 | B2 | 10/2006 | Yoshimasa |
| 7,198,689 | B2 | 4/2007 | Van Gompet et al. |
| 7,217,259 | B2 | 5/2007 | McDaniel |
| 7,265,158 | B2 | 9/2007 | Risen, Jr. et al. |
| 7,358,282 | B2 | 4/2008 | Krueger et al. |
| 7,378,450 | B2 | 5/2008 | Erkey et al. |
| 2001/0039407 | A1 | 11/2001 | Widlund |
| 2002/0193766 | A1 | 12/2002 | Gell et al. |
| 2003/0004484 | A1 | 1/2003 | Hammons et al. |
| 2003/0106825 | A1 | 6/2003 | Molina et al. |
| 2004/0116883 | A1 | 6/2004 | Krautkramer et al. |
| 2004/0151930 | A1 | 8/2004 | Rouns et al. |
| 2004/0158221 | A1 | 8/2004 | Mizutani et al. |
| 2004/0167488 | A1 | 8/2004 | Bellucci et al. |
| 2005/0010185 | A1 | 1/2005 | Mizutani et al. |
| 2005/0124960 | A1 | 6/2005 | Ruman |
| 2005/0137549 | A1 | 6/2005 | Lindsay et al. |
| 2005/0148984 | A1 | 7/2005 | Lindsay et al. |
| 2005/0182378 | A1 | 8/2005 | Bonelli et al. |
| 2005/0261652 | A1 | 11/2005 | Digiacomantonio et al. |
| 2006/0058764 | A1 | 3/2006 | Bohlen et al. |
| 2006/0063322 | A1 | 3/2006 | Hsu et al. |
| 2006/0129114 | A1 | 6/2006 | Mason, Jr. et al. |
| 2006/0148917 | A1 | 7/2006 | Radwanski et al. |
| 2006/0161125 | A1 | 7/2006 | Bohlen et al. |
| 2006/0206077 | A1 | 9/2006 | Warren et al. |
| 2006/0224133 | A1 | 10/2006 | Gannon et al. |
| 2006/0264884 | A1 | 11/2006 | Carstens |
| 2007/0100313 | A1 | 5/2007 | Luizzi |
| 2007/0124850 | A1 | 6/2007 | Buettner |
| 2007/0250028 | A1 | 10/2007 | Woltman et al. |
| 2007/0287973 | A1 | 12/2007 | Cohen et al. |
| 2008/0015535 | A1 | 1/2008 | Gannon et al. |
| 2008/0057811 | A1 | 3/2008 | Yahiaoui et al. |
| 2008/0207779 | A1 | 8/2008 | Yahiaoui et al. |
| 2008/0234647 | A1 | 9/2008 | Arterburn |

FOREIGN PATENT DOCUMENTS

| | | |
|---|---|---|
| EP | 0850628 | 7/1998 |
| EP | 0609236 | 5/2002 |
| GB | 2284767 | 6/1995 |
| JP | 04279159 | 10/1992 |
| KR | 1020010022000 | 3/2001 |
| KR | 100563880 | 3/2006 |
| WO | 9307841 | 4/1993 |
| WO | 9516424 | 6/1995 |
| WO | 9827910 | 7/1998 |
| WO | 9827912 | 7/1998 |
| WO | 9827913 | 7/1998 |
| WO | 9827915 | 7/1998 |
| WO | 9827916 | 7/1998 |
| WO | 9827917 | 7/1998 |
| WO | 9827918 | 7/1998 |
| WO | 9828015 | 7/1998 |
| WO | 9828017 | 7/1998 |
| WO | 9828019 | 7/1998 |
| WO | 9828022 | 7/1998 |
| WO | 9828023 | 7/1998 |
| WO | 9855065 | 12/1998 |
| WO | 9901094 | 1/1999 |
| WO | 9901095 | 1/1999 |
| WO | 9930659 | 6/1999 |
| WO | 0000235 | 1/2000 |
| WO | 2006028612 | 3/2006 |

OTHER PUBLICATIONS

Mahdavi et al., "A Biodegradable and Biocompatible Gecko-Inspired Tissue Adhesive"; Proceedings of the National Academy of Sciences; 2008; pp. 2307-2312; vol. 105, No. 7.

American Society for Testing Materials (ASTM) Designation: D1300-53T, Tentative Specifications and Methods of Test for Laminated Thermosetting Decorative Sheets; 1953; pp. 148-166.

Berner et al., "Photo Initiators—An Overview"; 1979, Journal of Radiation Curing; 8 pages.

Final Rule for U.S. Antiperspirant Drug Products for Over-the-Counter Human Use; Final Monograph; Federal Register, 2003, pp. 34273-34293; vol. 68; No. 110.

International Search Report for PCT/IB2009/05073 dated Mar. 26, 2010; 6 pages.

International Search Report for PCT/IB2009/053074; dated Mar. 26, 2010; 4 pages.

International Search Report for PCT/IB2010/050407; dated Oct. 21, 2010; 4 pages.

International Search Report for PCT/US2010/050408; dated Nov. 1, 2010; 4 pages.

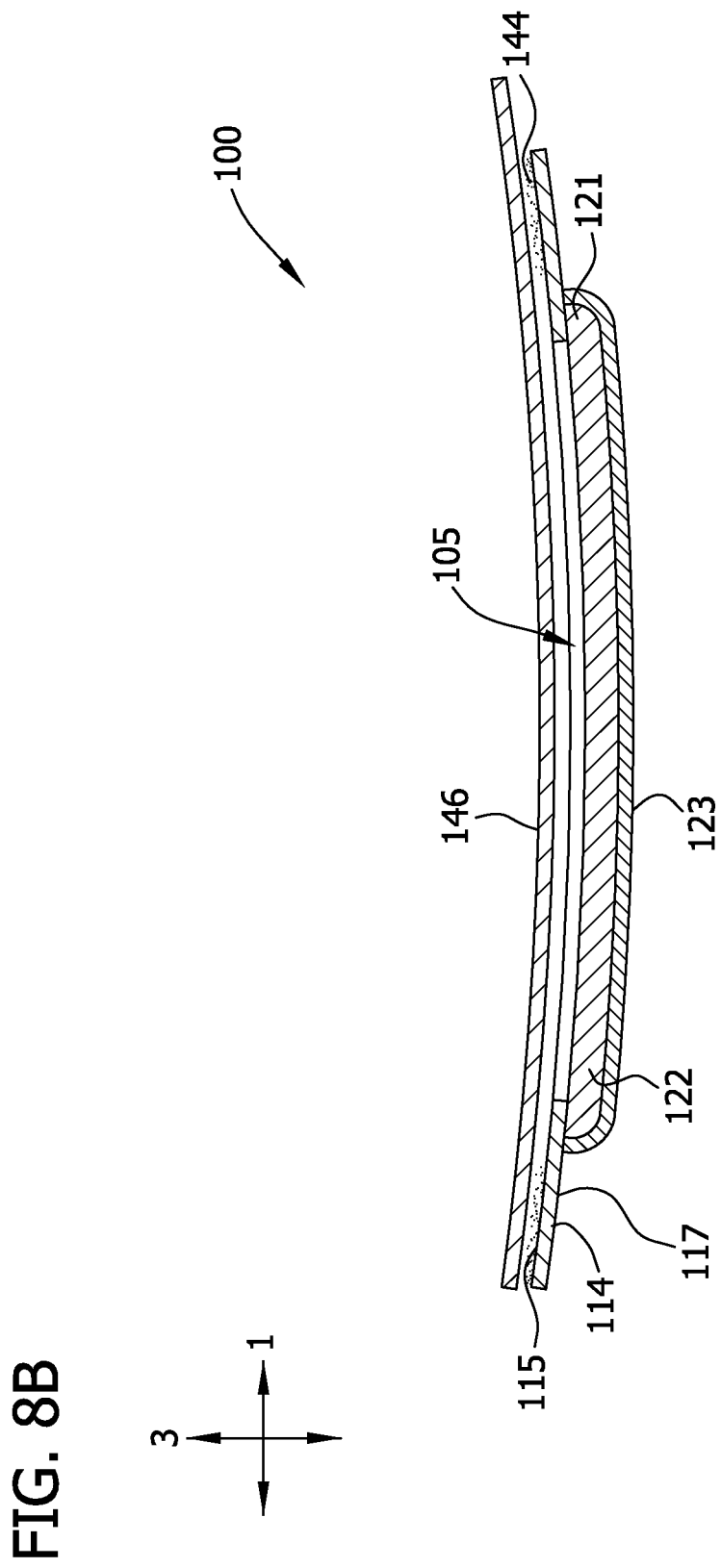

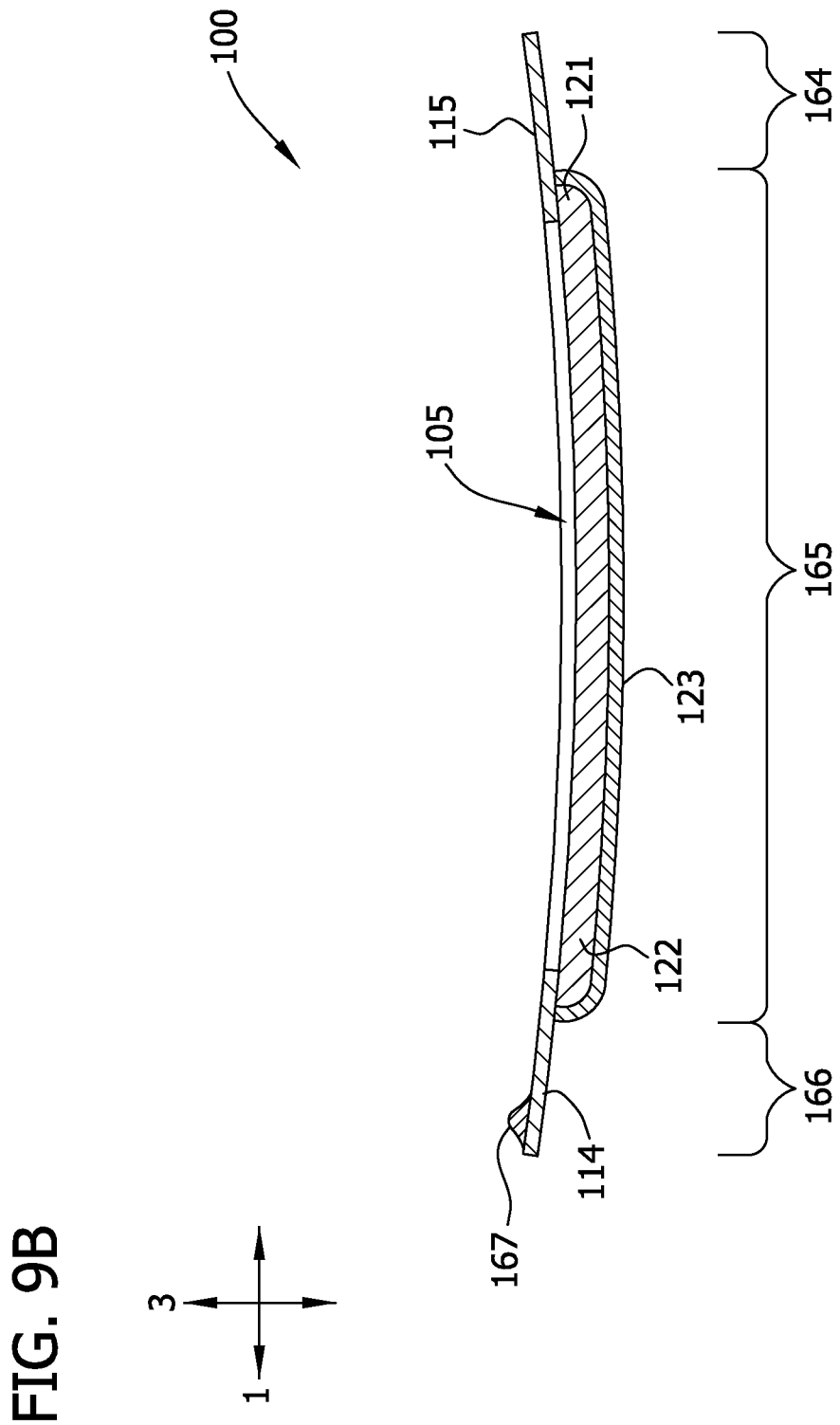

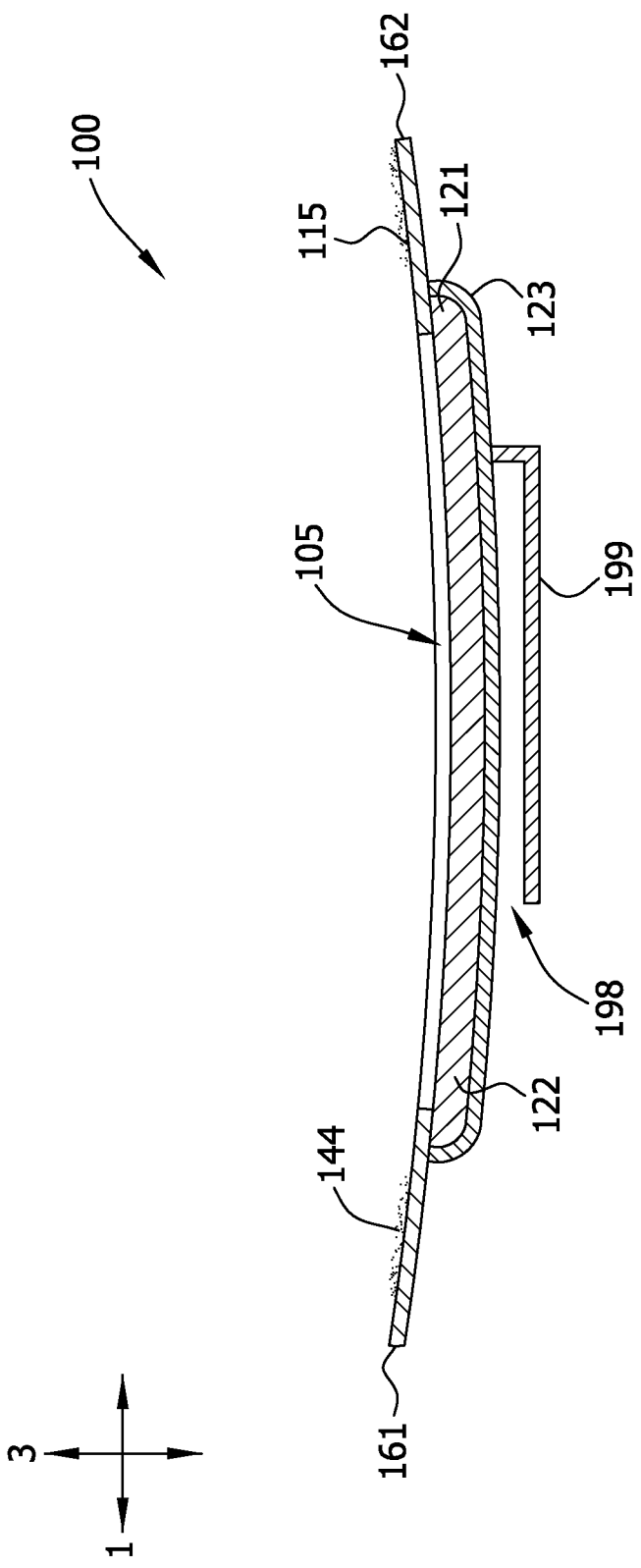

ABSORBENT ARTICLE HAVING LINE OF WEAKNESS FOR FOLDING THE ARTICLE

CROSS REFERENCE TO RELATED APPLICATION

This application is a divisional of U.S. patent application Ser. No. 12/335,316 filed Dec. 15, 2008, which is hereby incorporated by reference in its entirety.

BACKGROUND

The present invention relates generally to an absorbent article for absorbing bodily fluids.

Absorbent personal care articles intended to absorb discharged bodily fluids (i.e., exudates) are well known in the art. Such absorbent articles generally comprise a fibrous mass or other absorbent core which can absorb and hold body fluids. Similarly, it is well known that feminine care articles have been employed to absorb and hold liquids, such as urine and/or menses. A typical structure of an absorbent article includes a fluid impermeable back sheet, a fluid permeable top sheet, and an absorbent core positioned between the back sheet and the top sheet. In these absorbent personal care articles, the top sheet defines the body-facing side of the absorbent article and the back sheet defines the garment-facing side of the absorbent article. Prior absorbent articles have also included various other features to improve fluid handling, such as intake layers, distribution layers, retention layers, and the like.

Generally, the absorbent articles are held in place on a wearer's waist using elastic materials and fasteners in the waist portion of the absorbent product in the case of pant-like garments such as diapers and training pants, or by attaching the absorbent article to a crotch portion of the underwear or undergarment of a wearer in the case of pads or liners. Current methods of attaching the absorbent article to the underwear or undergarment of a wearer include placing an adhesive on the garment-facing side of the back sheet, having optional flaps (i.e., wings) that extend from the longitudinal sides of the absorbent article which wrap around the crotch portion of the underwear or undergarment of the wearer, and a combination of the adhesive and the flaps.

It has also been suggested to use an adhesive to adhere the absorbent article to the skin of the wearer. However, the design of such absorbent articles was essentially the same as the absorbent articles being attached to the underwear or undergarment of the wearer. That is, the adhesive is applied to the body-facing surface of the top sheet for attaching the article to the skin of the wearer. Alternatively, in another design, a portion of the back sheet was wrapped around and over the top sheet to partially define a body facing surface to which adhesive is applied for attaching the article to the wearer's skin. While these designs are effective for adhering the absorbent article to the skin of a wearer, they are not comfortable for the wearer because the shape and size of the absorbent articles are the same as those absorbent articles which are traditionally attached to the undergarment or underwear of the wearer.

Absorbent articles that are attached to the underwear or undergarment of a wearer can also be uncomfortable for the wearer. During normal movement of the body, portions of the body place opposed forces on the undergarment, which may cause the undergarment to become bunched or twisted. When this occurs, the absorbent article attached to the underwear or undergarment may also become bunched or twisted causing discomfort to the wearer of the absorbent article. For example, the presence and absence of pressure from the absorbent article on the inner thighs as the wearer moves, which is often described by wearers as feeling "like a diaper", is one source that compromises comfort for wearers of conventional absorbent articles, including liners, ultra-thin absorbent pads, and maxi pads. In addition, the movement of the wearer or deformation of the underwear while being worn may also cause the absorbent article to have a poor fit against the body of the wearer, which can result in leaks from the absorbent article.

Another disadvantage of conventional absorbent articles is that the silhouette or outline of the absorbent article may be visible to others through the clothing of the wearer. Even currently available ultra-thin absorbent articles may be visible through tight fitting outer clothing of a wearer. Therefore, conventional absorbent personal care articles do not always provide discretion for wearers.

Moreover, conventional feminine care absorbent articles (e.g., panty liners, ultra-thin absorbent pads, maxi pads) do not provide a suitable anatomic fit for most female wearers. Instead, typical conventional feminine care absorbent articles have a generally flat body-facing surface. However, the female vaginal region is not flat but rather complex. In use, the generally flat body-facing surface of conventional feminine care absorbent articles does not contour well with respect to the complex female vaginal region. As a result, gaps are often formed between the article and vaginal region. These gaps allow the article to move relative to the wearer and provide passages through which body fluids can leak.

There is therefore a need in the art to provide wearers of absorbent articles with a discrete absorbent product that is as easy to use, comfortable to wear, and inhibits leakage from the absorbent article.

SUMMARY

In one aspect, a feminine care absorbent article having a longitudinal axis and a transverse axis generally comprises an absorbent structure configured for disposition adjacent a female wearer's vaginal region to absorb bodily fluids discharged by the wearer. The absorbent structure has end portions and a middle portion located between the end portions. The absorbent structure has a pair of lines of weakness disposed in one of the end portions and configured to facilitate folding of the absorbent structure in a longitudinal direction in response to a lateral compressive force. The pair of lines of weakness diverges from each other as the pair of lines of weakness extends from the one of the end portions toward the middle portion of the absorbent structure. The absorbent structure has a relief for inhibiting the longitudinal folding of the absorbent structure facilitated by the at least one line of weakness from extending beyond the middle portion of the absorbent structure.

In another aspect, a feminine care absorbent article having a longitudinal axis and a transverse axis generally comprises an absorbent structure configured for disposition adjacent a female wearer's vaginal region to absorb bodily fluids discharged by the wearer. The absorbent structure has an upper end portion, a lower end portion and a middle portion located between the end portions. Both the upper and lower end portions of the absorbent structure include a line of weakness configured to facilitate folding of the absorbent structure in a longitudinal direction in response to a lateral compressive force. The absorbent structure has a relief for inhibiting the longitudinal folding of the absorbent structure facilitated by at least one of the lines of weakness from extending beyond the middle portion of the absorbent structure.

In yet another aspect, a feminine care absorbent article having a longitudinal axis and a transverse axis generally comprises an absorbent structure configured for disposition adjacent a female wearer's vaginal region to absorb bodily fluids discharged by the wearer. The absorbent structure has an upper portion, a middle portion, and a lower portion. The absorbent structure has a first line of weakness disposed in the lower portion and configured for folding the absorbent structure in a longitudinal direction in response to a compressive force. The absorbent structure has a generally V-shaped second line of weakness disposed in the upper portion and is configured to resist folding of the absorbent structure in the upper portion of the absorbent structure.

In still another aspect, a feminine care absorbent article having a longitudinal axis and a transverse axis generally comprises an absorbent structure configured for disposition adjacent a female wearer's vaginal region to absorb bodily fluids discharged by the wearer. The absorbent structure has an upper portion, a middle portion, and a lower portion. The lower portion has a first line of weakness configured for longitudinally folding the absorbent structure in response to a lateral compressive force. The absorbent structure has a second line of weakness defining a relief for inhibiting the longitudinally folding the absorbent structure facilitated by the first line of weakness from extending into the middle portion of the absorbent structure. The second line of weakness includes an arcuate portion for facilitating transverse folding of the absorbent article.

BRIEF DESCRIPTION OF THE DRAWINGS

FIGS. 8A and 8B each show an absorbent article of the present invention having a release sheet applied thereto.

FIG. 9B shows a cross-sectional view of FIG. 9A along line 9B-9B.

FIGS. 10A and 10B show embodiments of the present invention with placement guides.

DEFINITIONS

Figure 1:
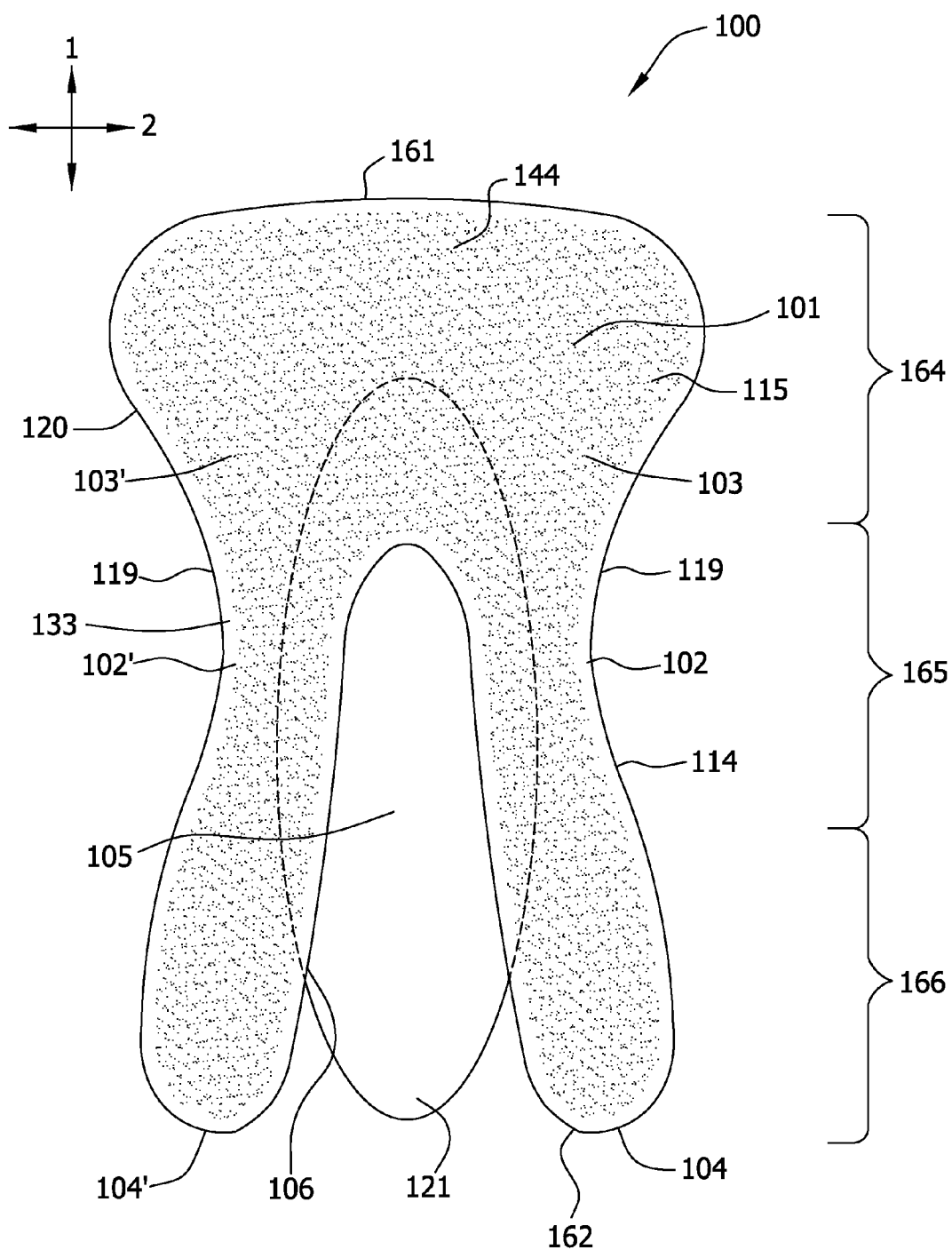
FIG. 1 shows a top view of an embodiment of an absorbent article of the present invention.

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

It should be understood that the term "absorbent product" or "absorbent article", as used herein, refers to any article used to control bodily fluids that are configured to absorb and retain bodily exudates, including urine, blood, menses, and other bodily discharges, such as sweat and vaginal secretions resulting from sexual activity and the like. In addition, the term is intended to include odor absorbing articles.

As used herein, the term "polymer" generally includes, but is not limited to, homopolymers, copolymers, such as, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to, isotactic, syndiotactic, and random symmetries.

As used herein, "body-facing surface" means that surface of the absorbent article which is intended to be disposed toward or placed adjacent to the body of the wearer during ordinary use. The "garment-facing surface" is on the opposite side of the absorbent article from the body-facing surface. The garment-facing surface is an outward surface of the absorbent article and is intended to be disposed to face away from the wearer's body during ordinary use. The garment-facing surface is generally arranged to face toward or placed adjacent to the wearer's undergarments when the absorbent article is worn.

As used herein, the term "connected" is intended to mean directly connected and indirectly connected. By directly connected, it is intended that the connected elements are in contact with one another or affixed to one another. By indirectly connected, it is intended that one or more intervening or intermediate elements are between the two elements which are secured or "connected" together. The intervening elements may be affixed.

As used herein, the term "absorbent structure" is intended to mean a configuration of an absorbent material that allows bodily fluids to be absorbed by the absorbent material.

DETAILED DESCRIPTION

The absorbent product of the present invention provides an absorbent article that is designed to adhere to the body of a wearer in the area of the body of the wearer that may need bodily fluids absorbed. In one particular use, the absorbent article is attached to the body of a female wearer to or around the vulva region of the body. By "to or around the vulva region", it is meant adjacent regions of the body of a female including the pubic region and the perinea region. When applied to or around the vulva region of the female body, the absorbent article may be used as a panty-liner, sanitary napkin, or incontinence article.

In addition, the absorbent article may be worn as an underwear substitute since the absorbent article of the present invention does not need underwear to hold the absorbent article in place. As an underwear substitute, the absorbent article provides protection to the vulva area by creating a barrier between the outer clothing and the vulva of a wearer. When worn as an underwear substitute, the absorbent article serves to protect the outer clothing of the wearer from bodily discharges from the vulva region of the wearer's body. In addition, when the absorbent article is worn as an underwear substitute, the absorbent article also serves to protect the sensitive skin and body features of the vulva region from roughness of the outer clothing, thereby preventing or alleviating irritation to the sensitive skin and body features of the vulva region.

Figure 2:
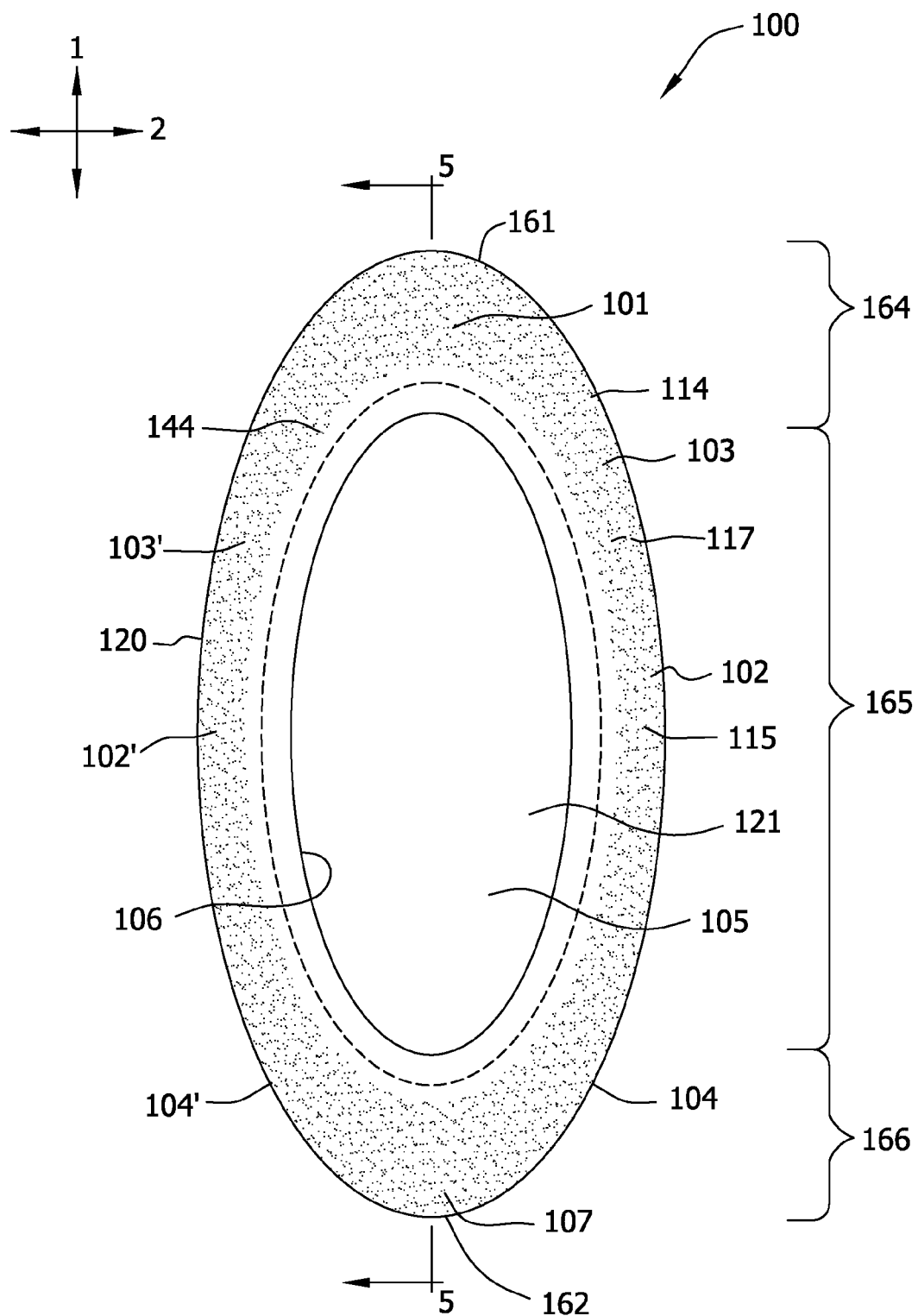
FIG. 2 shows a top view of another embodiment of an absorbent article of the present invention.
Figure 3:
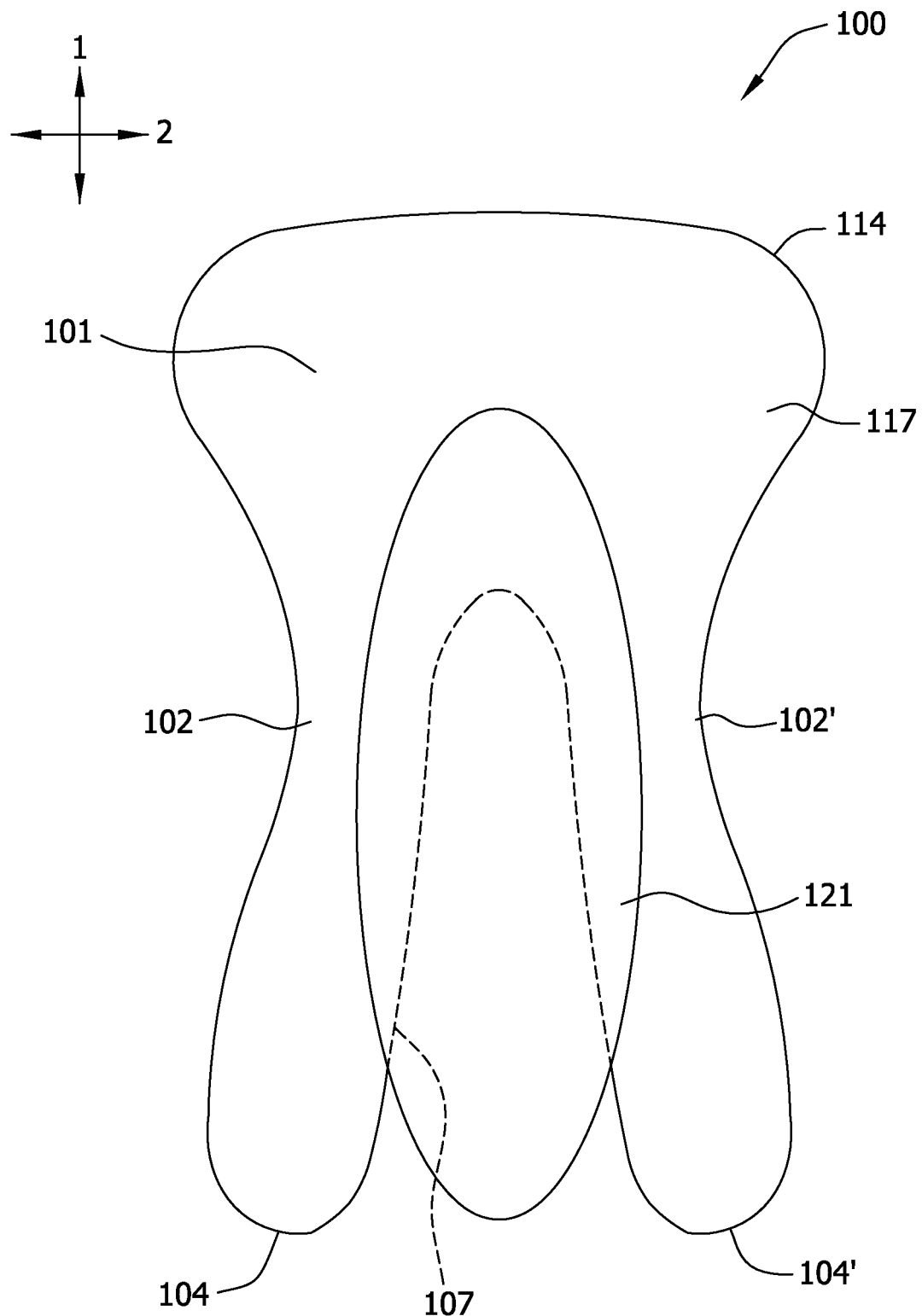
FIG. 3 shows a bottom view of the absorbent article shown in the embodiment of absorbent article of the present invention shown in FIG. 1.
Figure 4:
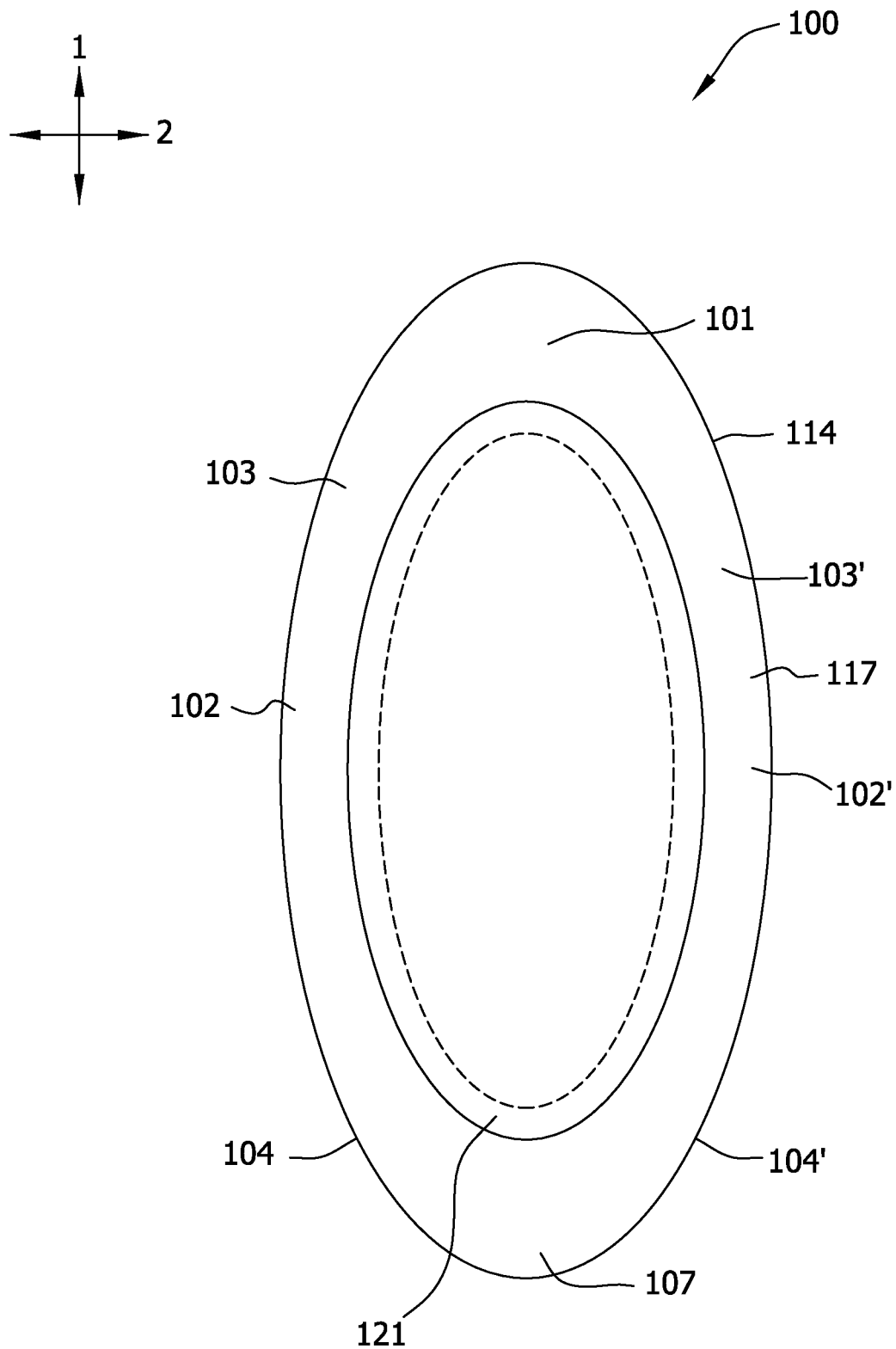
FIG. 4 shows a bottom view of the absorbent article shown in the embodiment of absorbent article of the present invention shown in FIG. 2.

To gain a better understanding of the present invention, attention is directed to the figures of the present specification. As seen in FIGS. 1 and 2, an absorbent article 100 has a longitudinal direction 1 and a lateral direction 2. One component of the absorbent article 100 is a shell 114 having a first side 115, as shown in FIGS. 1 and 2, and a second side 117, as shown in FIGS. 3 and 4. The first side 115 of the shell 114 is the body facing side of the absorbent article 100 and the second side 117 of the shell 114 is the garment facing side of the absorbent article. The shell 114 serves to provide the overall contour or silhouette of the absorbent article 100 of the present invention. In addition, the shell 114 also provides a surface for attachment or adhesion of the absorbent article 100 to the body of a wearer.

The shell 114 of the absorbent article 100 has a first region 101. This first region 101 has a pair of lateral side regions 102, 102' extending from the first region. This pair of lateral side regions each has a proximate end 103, 103' adjacent the first region 101 and a distal end 104, 104'. The pair of lateral side regions 102, 102' and the first region 101 together define an opening 105 in the shell 114. This opening 105 may be open near the distal ends 104, 104' of the lateral side regions 102, 102', as seen in FIG. 1 or, as shown in FIG. 2, the lateral side regions 102, 102' may be joined at the distal end 104, 104' to form a second region 107. The portions of the lateral side regions 102, 102' and the first region 101 adjacent the opening 105 form a circumference or edge 106 around the opening 105. This circumference or edge 106 typically has thickness in the z-direction 3 which is about equal to the thickness of the shell. However, the thickness of the edge may be increase or decreased to improve comfort for a wearer or performance of the absorbent article.

The absorbent article 100 further has an absorbent structure 121 attached to the second side 117 of the shell 114, as seen in FIGS. 1-6. At least a portion of the absorbent structure 121 is positioned in the absorbent article such that a majority of the opening 105 in the shell has the absorbent structure 121 positioned therein, as can be seen in FIGS. 1 and 2. In one particular embodiment, the entire area of the opening 105 has the absorbent structure 121 positioned therein. Generally to hold the absorbent structure in place, a portion of the absorbent structure 121 is attached to the second side 117 of the shell 114. Suitable methods of attaching the absorbent structure 121 to the second side 117 of the shell 114 include adhesives, mechanically bonding the absorbent structure 121 to the second side 117 using bonding means such as ultrasonic bonding, heat and pressure bonding, and the like, which are discussed in more detail below.

In one embodiment, the opening 105 in the shell may be a hole, which is devoid of any material, or and in another embodiment, the opening 105 may be a region which is permeable to body fluids. If the opening is a region which is permeable, the opening may have a material such as hydrogel or similar material that will allow body fluids to flow through the material.

In one embodiment, the first side 115 of the shell 114 is adapted to be the body contacting side of the absorbent article. The first region 101, the lateral sides regions 102, 102' and the second region 107, when present, on the first side 115 of the shell 114 are designed or adapted to contact and attach or adhere to the wearer's skin. In one particular embodiment, the first region 101 of the shell 114 is designed or adapted to contact a female wearer's skin surrounding the vulva region of the female torso when the absorbent article 100 is applied to the wearer. By "designed or adapted to contact a female wearer's skin surrounding the vulva region of the female torso", it is meant that the size and shape of the shell 114, including the first region and the lateral side regions and second region, if present, is such that the shell 114 fits in the vulva region and possibly the surrounding pubic region and perinea regions of the female torso. Generally, the shell 114 is sized and shaped such that the extent of the first side 115 of the shell 114 only contacts and attaches or adheres to the skin surrounding and proximate to the vulva area and possibly the pubic and perinea regions of the wearer. In addition to contacting the skin in the vulva, pubic and perinea regions of the wearer, the first side 115 of the shell 114 may also contact and attach or adhere to any hair in the vulva area of the wearer which may be present. The first side 115 of the shell 114 is what holds the absorbent article in place on the body of a wearer.

To gain a better understanding of the vulva region and surrounding regions of the female body, a general description of the anatomical structures can be found in *The Illustrated Running Press Edition of the American Classic Gray's Anatomy* (1974) by Henry Gray and Structure and Function in Man (1974) by Stanley W. Jacob, M.D., F.A.C.S. and relevant portions are included herein by reference. The general form can be found in *Anatomy for an Artist: Elements of Form* by Eliot Goldfinger and relevant portions are included herein by reference. The general description of the pubic hair covering these regions can be found in *Woman's Body: A Manual for Life* and relevant portions are included herein by reference.

The female anatomical structures to be described include the leg and the lower torso. The external anatomical structures of the lower torso include gluteal region and perineum region. The gluteal region includes the buttocks and the anus. The anatomical structure involved on the leg is the medial surface of the upper thigh.

The gluteal region includes generally the buttocks and anus and is typically bound in front by the line of the buttocks and the gluteal folds, in the back by the sacral triangle and the sides by lines extending through the greater trochanters. The shape of the gluteal region is roughly hemi-spherical and convex, and is determined by a series of muscles including the gluteus maximus and a series of fat pads including the posterior gluteal fat pad. The line of the buttocks separates the gluteal region and the perineum region.

The upper thigh region includes typically the right and left thigh and is typically bound on top by the thigh lines and the sides by the front and back of the leg. The thigh lines are two lines that are on either side of the labia and each of the lines runs along the line of the inguinal ligament to the gluteal folds and marks where the upper thigh meets the lower torso. The shape of the region is roughly a portion of a tapered cylinder and convex, and is shaped by a series of muscle groups including the gracilis, pectineus, adductor longus, adductor brevis, and adductor magnus and series of fat pads including the inner thigh fat pad.

The perineum region, which extends from the inferior outlet of the pelvis to the bony structure of the coccyx, is comprised of two divisions, the urogenital triangle and the anal division or obstetrical perineum. The region includes the external organs of reproduction: the mons pubis, labia majora and minora, clitoris, meatus urinarius, and the opening to the vagina. The region is generally bound in front by the lower abdominal line, on the sides the thigh lines, and in the back the line of the buttocks. The abdominal line is a line that passes across the top of the pubis. The lines of the buttocks are lines that connect the thigh lines to the gluteal cleft. For convenience in describing the form and created spaces in the perineum region, this region will be subdivided into three regions an anterior region including the mons pubis, a central region including the labia majora and minora, and posterior region. The anterior region is bound in front by the lower abdominal line, in back by anterior commissure, and on the sides by line of the labia. The central region is bound in front by the anterior commissure, in the back by the posterior commissure, and on the side by the line of the labia. The posterior region is bound in front by the line of the labia, in the back by the lines of the buttocks, and on the sides the thigh line.

The vulva region (or vaginal region) includes the female external genitalia and generally includes the anterior and central regions of the perineum. The mons pubis (or veneris) is generally a rounded eminence in front of the symphysis pubis, formed by a collection of fatty tissue including the pubic fat pad beneath the integument and is generally covered with pubic hair. The labia majora are generally two prominent longitudinal cutaneous folds extending downward from the mons veneris to the anterior boundary of the perineum, and generally enclosing the common urinary-sexual opening. The space between the two folds is the labial cleft. Each labium has generally two surfaces, an outer, which is pigmented and covered generally with strong, crisp pubic hairs, and an inner within the labia cleft, which is smooth and is beset with large sebaceous follicles and is continuous with the genito-urinary mucous tract; between the two there is considerable quantity of areolar tissue, fat including the labia fat pad, and tissue besides vessels, meeting the anterior commissure. Posteriorly they are typically not joined, but generally appear to become lost in the neighboring integument, terminating close to, and nearly parallel with each other. Together with the connecting skin between them, they form the posterior commissure or posterior boundary of the vulval orifice. The interval between the posterior commissure and the anus constitutes the perineum region. The fourchette is the anterior edge of the perineum, and between it and the hymen is a depression, the fossa navicularis. The line of the labia separates the labia and the perineum region.

The labia minora are two small cutaneous folds, situated generally within the labia majora, and extending from the clitoris obliquely downward, outward, and backward on each side of the orifice of the vagina.

The form of the perineum, gluteal, and upper thigh regions combine to form a very intricate skin topography and spaces. The roughly two-hemispherical-like forms of the buttocks, the roughly tapered-cylinder-like form of the upper thigh, split-teardrop-like form of the vulvar region create intricate generally convex topography with intersections to form a series of recesses. The generally convex topography of the buttocks, the vulvar region, and upper thigh join to create spaces including two inner thigh grooves along two thigh lines, a depression in the posterior perineum region and a cleft extending through the labia and gluteal clefts. The grooves, depression, and cleft are like interconnected recesses in the topography. The central region general has lateral sides separated by a distal surface created by the labial cleft and includes the labial cleft.

Pubic hair generally cover some of these regions and fill in a portion of these recesses especially the labial cleft and the portion of the groove of the thigh parallel to the labial cleft to create a hair surface topography. The hair topography is the surface topography of an imaginary distal surface created by the hair. The depression of the perineum, thigh groove parallel to the gluteal cleft, and the gluteal cleft generally has little or no pubic hair. The skin topography combines with the hair topography to create an overall body topography.

This intricate space created by the intricate body form in this region of the body varies between women in both size and form, and varies with the position and movement of the women. Some of these variations are summarized in "Female genital appearance: 'normality' unfolds" by Jillian Lloyd et. al., BJOG: An International Journal of Obstetrics and Gynecology, May 2005, Vol. 112, pp. 643-646 and is included herein by reference.

As a woman ages, many changes occur to the vulva region. Skin begins to lose its elasticity and hangs more loosely from the body. In addition, the fat pads tend to be reduced, changing the topography of the vulva region. As a result, there is a need for a product which can be adapted to these changing conditions.

When the absorbent article 100 is positioned for use on a wearer, generally the first side 115 of the shell, including the first region 101, the lateral side regions 102, 102' and the second region 107, if present, are positioned on the wearer outside the labia majora of the wearer. This will allow any fluid coming from the vulvo-vaginal area of the body of a wearer to pass through the opening 105 present in the shell 114, so that the fluid may flow into the absorbent structure 121. The opening 105 can be an area that is devoid of the shell material or any other material. Alternatively, the opening can be a permeable area, which is permeable to body fluids, containing a material that is permeable. Typically, the absorbent structure 121 is the portion of the absorbent article which provides absorbency to the absorbent article. In an alternative embodiment, the first side 115 of the shell 114 may also provide some absorbency to the absorbent article. For example, the second first side 115 of the shell 114 may contain an absorbent material integrated into the shell 114, such that the first side of the shell 114 has some degree of absorbency. The first side 115 of the shell 114 may have an absorbent material coated or impregnated into the shell material.

When the second region 107 is present, as shown in FIG. 2, the entire opening 105 is surrounded by the shell 114. When the second region 107 is not present, as shown in FIG. 1, the opening 105 has an unbound end, meaning that the distal ends 104, 104' of the lateral side regions 102, 102' are not connected. Each configuration of the absorbent articles shown in FIGS. 1 and 2 have advantages. For example, the configuration shown in FIG. 1, where the second region 107 is not present in the absorbent article 100, the absorbent article 100 may provide more comfort to the wearer when being worn. That is, in use of the absorbent article 100, the first region 101 is designed to be placed towards the anterior region of the vulva region of the wearer. By not having the second region, the absorbent article 100 will not be positioned in the perinea region of the wearer, which may provide improved comfort to the wearer. Alternatively, by having the second region 107 present, the absorbent article may provide superior leak protection to the wearer, by creating a seal completely surrounding the labia majora of a wearer. As a result, any and all fluid leaving the vaginal cavity will be confined to the absorbent article.

Figure 6:
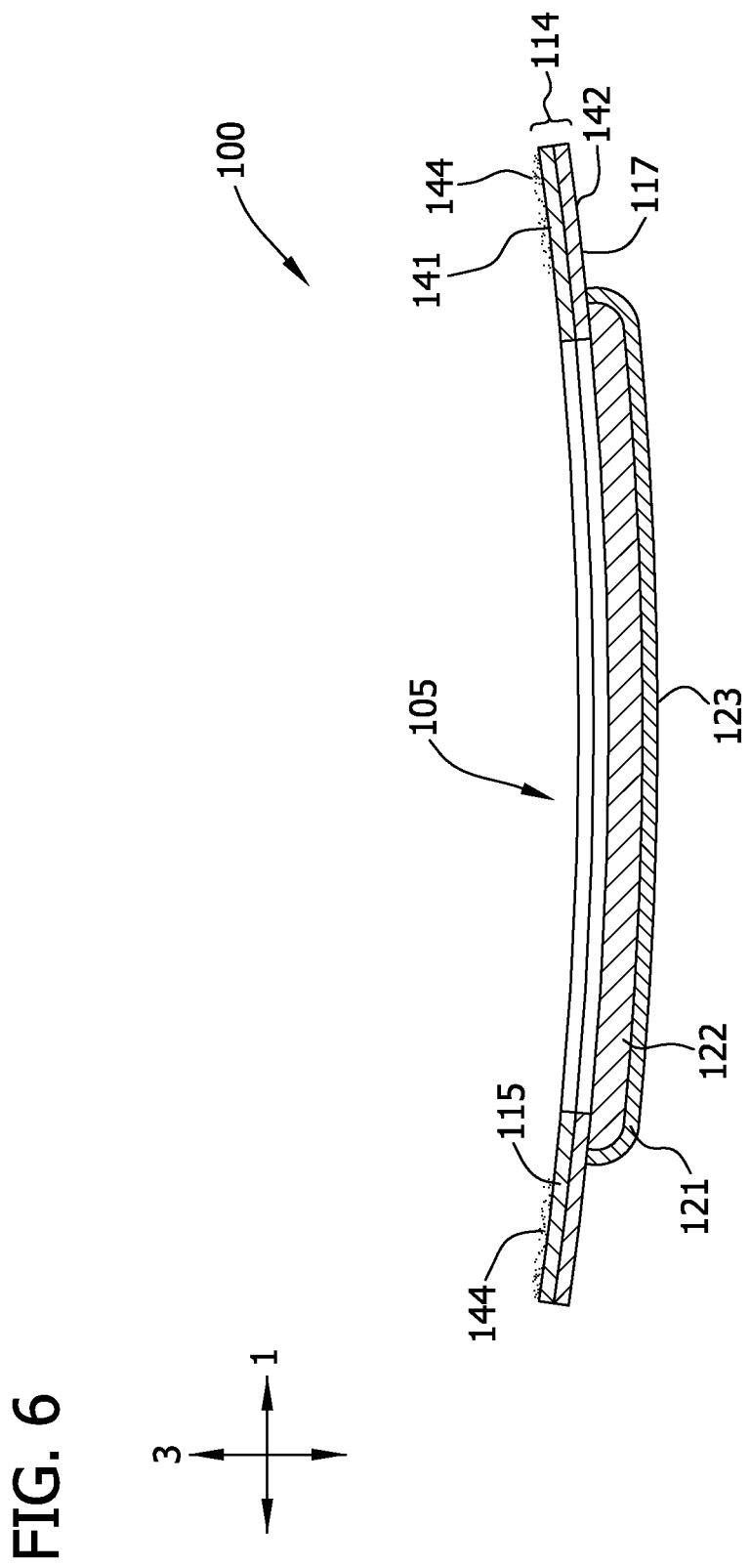
FIG. 6 shows a side cut-away view of an embodiment of an absorbent article of the present invention shown in FIG. 2 along line 5-5 having a two-layer shell.

The shell 114 of the absorbent article 100 may be prepared from a variety of materials. The shell may include a layer constructed of any material which will function to be operatively liquid impermeable. The shell 114 may, for example, include a polymeric film, a woven fabric, a nonwoven fabric or the like, as well as combinations or composites thereof. For example, the shell 114 may include a polymer film laminated to a woven or nonwoven fabric. A laminate shell 114 structure is shown in FIG. 6, having an upper layer 141 and a lower layer 142, wherein the upper layer 141 is the body-facing side of the shell 114 and the lower layer 142 is the garment facing side of the shell 114. In a particular feature, the polymer film can be composed of polyethylene, polypropylene, polyester, silicone or the like, as well as combinations thereof. Additionally, the polymer film may be micro-embossed, have a printed design, have a printed message to the consumer, and/or may be at least partially colored. Suitably, the shell 114 can operatively permit a sufficient passage of air and moisture vapor out of the absorbent article 100, particularly out of an absorbent structure 121 while blocking the passage of bodily fluids and odors often associated with bodily fluids. An example of a suitable shell material can include a breathable, microporous film, such as those described in, for example, U.S. Pat. No. 6,045,900 to Haffner et al., the entire disclosure of which is incorporated herein by reference and made a part hereof. Other shell materials which are extensible may be used in the present invention, including, for example foams. One example of a suitable foam is a polyurethane foam with a negative Poissons ratio. Examples of extensible backsheet materials are described in U.S. Pat. No. 5,611,790, issued Mar. 18, 1997, to Osborn, III et al., herein incorporated by reference in its entirety. Other materials that are inherently breathable, such as polyurethanes, may be used to form the shell 114.

In one particular embodiment, the shell 114 may be a laminate of a woven or nonwoven fabric with a silicone polymer, wherein the silicone polymer has adhesive properties. The second side 117 of the shell will be woven or nonwoven fabric and the first side 115 of the shell will be silicone polymer. One commercially available laminate is an Oleeva Fabric® 1 available from Bio Med Sciences, Inc., which have offices at 7584 Morris Court, Suite 218 Allentown, Pa. 18106. The Oleeva Fabric® is a silicone sheeting having adhesive properties laminated to a fabric backing. The silicone sheeting will form the body facing first side 115 of the shell material. Relating this particular structure to the Figures, in FIG. 6, the silicone polymer is the upper layer 141 of the shell 114 and the nonwoven or woven layer is the lower layer 142 of the shell.

Bicomponent films or other multi-component films can also be used as the shell 114 material. In addition, woven and/or nonwoven fabrics which have been treated to render them operatively liquid-impermeable can also be used as an effective shell 114 material. Another suitable shell material can include foams. Examples of foam include a closed-cell polyolefin foam, a foam with a negative Poissons ratio and other similar foams. Other suitable polymeric materials include a polyurethane polymer material, a silicone polymer, or other similar materials. Silicone polymers having naturally occurring adhesive properties, or silicone polymers having a silicone adhesive layer applied thereto are of particular interest for the shell material. Such silicone polymers will allow the first side 115 of the shell 114 to adhere to the body of the wearer without the need of an additional adhesive. These materials may be laminated to another material, such that the second side 117 of the shell 114, which is the garment facing side of the absorbent article 100 is laminated to the other material, so that the adhesive nature of the silicone polymer does not adhere the garment to the undergarments of the wearer. In another embodiment, the shell material may be prepared from an interpenetrating polymer network or two or more polymers. Generally, one of the polymers of the interpenetrating polymer network may be a silicone material. Examples of interpenetrating polymer networks are described in U.S. Pat. No. 5,759,560, issued to Dillion, which is hereby incorporated by reference in its entirety.

The shell material should be selected such that the overall properties of the shell allow the shell material to move with the skin of the wearer during normal use and normal movements by the wearer during use. By "normal movement by the wearer" it is meant any movement that normally occurs during use of the absorbent article, including walking, running, sitting, standing, kneeling, riding a bicycle, exercising, playing sports, getting into and out of an automobile, and other similar movements made by wearers when wearing an absorbent article. The shell should not be too rigid, such that the shell detaches from the skin of the wearer during use and the shell should not be so flexible that the shell tends to twist and bunch during use. The shell should have sufficient flexibility to conform to the skin of the wearer. The shell should also have the ability to remain attached to the body of the wearer under moist or wet conditions.

Generally, the shell material should have sufficient thickness to allow the shell 114 to mold to the body of the wearer, but not too thick that the shell 114 becomes uncomfortable for the wearer to wear. In addition, the shell 114 should not be so thin that it ineffectively forms a seal with the skin of the wearer when applied to the wearer, or becomes detached from the skin of the wearer during use and normal movement of the wearer during use or that it does not adequately conform to the shape and skin of the wearer at the point of attachment to the wearer. Depending on the material used for the shell, the typical thickness of the shell is between 0.03 mm and about 5.0 mm, more particularly between 0.1 mm and 3.0 mm. In one particular embodiment, the thickness of the shell is between 0.25 mm and about 3.0 mm. Again, the actual thickness used is dependent of several factors including rigidity of the material, the flexibility of the material, and the ability of the material to assume the shape of the skin of the wearer at the location of use (i.e., the vulva region of a wearer).

The second side 117 of the shell 114 may form a portion of the garment-facing side of the absorbent article 100 when worn by a wearer. The shell material should be selected such that the second side 117 of the shell will freely move against the undergarment or clothing of a wearer. One way to achieve this result is to construct the second side 117 of the shell 114 to have a fairly low coefficient of friction. This will allow the second side 117 of the shell 114 to freely move against the undergarment or other clothing worn by the wearer. If the second side 117 of the shell 114 does not freely move against the undergarment or other clothing worn by the wearer, the absorbent article may catch on the undergarment or clothing, which can result in the absorbent article being prematurely and undesirably removed from the wearer or may cause the absorbent article to be shifted from its desired placement against the body of a wearer.

In order to achieve the desired coefficient of friction on the second side 117 of the shell 114, the materials used to prepare the shell can be selected such that the second side 117 of the shell material will inherently have the desired coefficient of friction. Alternatively, the second side 117 of the shell 114 may be treated with a coating composition, such a polytetrafluoroethylene containing coating, a silicone containing coating, or other similar coating having low coefficient of friction properties. Alternatively, the shell 114 can be made from a laminate of two or more materials such that the first side 115 of the shell 114 is prepared from a material that meets the needed properties of the first side 115, while the material selected for the second side 117 of the shell 114 meets the desired coefficient of friction such that the second side 117 will move freely against the undergarment or garment being worn by a wearer.

Figure 5:
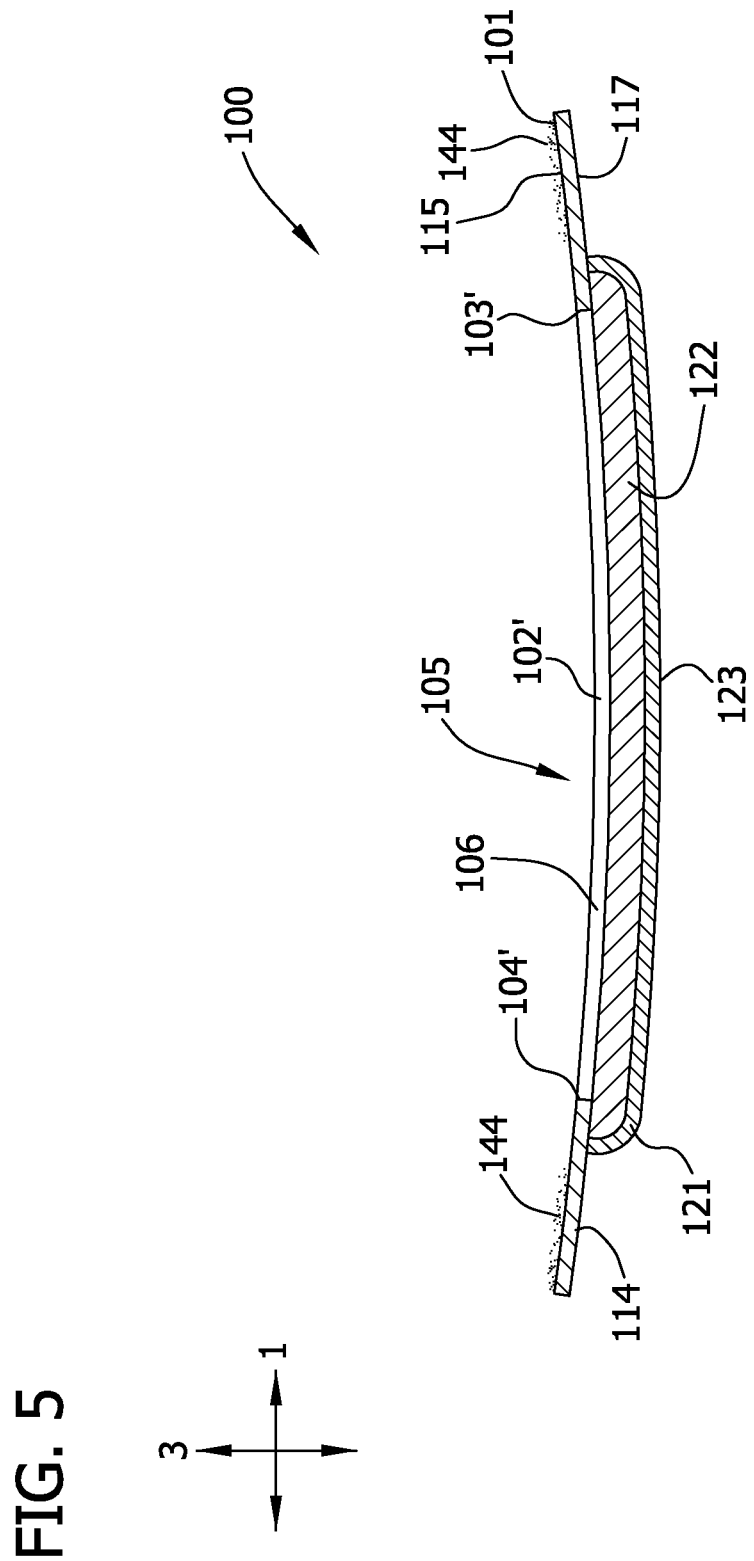
FIG. 5 shows a side cut-away view of an embodiment of an absorbent article of the present invention shown in FIG. 2 along line 5-5.

The shell 114 of the absorbent article 100 may be flat or may have a three-dimensional shape. As seen in FIG. 5, which is a cross-sectional side view of the absorbent article, the shell 114 has a three-dimensional concave shape. Alternatively, as seen in cross-sectional side views of FIG. 6, the shell 114 may have a generally flat shape. By providing the absorbent article 100 with a three-dimensional concave shape, as seen in FIG. 5, placement of the article may be easier for the wearer. Generally, the three-dimensional shape could be such that it closely matches the overall general curvature of the vulva region and optionally the pubic and perinea regions of most women, when the absorbent article is used as a panty-liner, sanitary napkin, or a feminine incontinence article. To form the shell 114 with a three-dimensional shape, the shell may be molded in any manner known to those skilled in the art, for example heat molding. The manner in which the three-dimensional shape is imparted to the shell 114 is not critical to the present invention.

When the shell 114 is a generally flat shape, for example as shown in FIG. 6, meaning that the shell does not have a third dimension other than thickness, the shell 114 should be made to be flexible enough that the shell 114 can conform to the body of the wearer at the point of attachment. In addition to being flat, the overall shape of the shell 114 may be contoured, as seen in FIG. 1. In one embodiment, the contour shape may be such that the narrowest point of the contour is in the crotch area of the shell 114 nearest the vulva region, as seen in FIG. 1. The contour shape shown in FIG. 1 is one of many possible shapes, in which the shell 114 and absorbent article may be prepared. Other shapes may be used, without departing from the scope of the present invention. Generally, the shape selected should be such that the shell 114 and absorbent article 100 are comfortable for the wearer to wear, while providing leakage protection to the wearer. It is noted that a contour shape may also be used in conjunction with a three-dimensional shell. Further discussion of the overall shape of the absorbent article may be found below.

The shell may be any desired color or may be translucent. In addition, the shell may have a matte finish, satin finish, or a smooth finish. The particular finish color or translucency can be a matter of choice for the manufacturer of the absorbent article of the present invention. However, providing a shell which is translucent may assist the wearer in placing the absorbent article 100 prior to use, since the wearer may be able to see where the article is placed compared to the genitalia of the wearer.

The absorbent structure 121 is designed to absorb body exudates, including menstrual fluid, blood, urine, and other bodily fluids, such as sweat and vaginal discharges. The absorbent structure 121 has a longitudinal direction 1 and a lateral direction 2 and is shown in FIGS. 1-4, and a thickness in the z-direction 3, as seen in FIGS. 5 and 6. This absorbent structure 121 may be a single layer or may be multiple layers. Typically, the absorbent structure 121 has an absorbent core 122 and a generally liquid impermeable backsheet 123. This absorbent core 122 may contain one or more layers of absorbent materials. That is, the absorbent core 122 may be a single layer of absorbent materials or may be a multilayer structure. Each of the layers of the absorbent core 122 can contain similar materials or different materials. The materials that can be used to form the absorbent core 122 include those materials conventionally used in absorbent articles, such as, cellulose, wood pulp fluff, rayon, cotton, and meltblown polymers such as polyester, polypropylene, or coform. Coform is a meltblown air-formed combination of meltblown polymers, such as polypropylene, and absorbent staple fibers, such as cellulose. A desired material is wood pulp fluff, for it is low in cost, relatively easy to form, and has good absorbency.

The absorbent core 122 can also be formed from a composite comprised of a hydrophilic material that may be formed from various natural or synthetic fibers, wood pulp fibers, regenerated cellulose or cotton fibers, or a blend of pulp and other fibers. One particular example of a material that may be used as the absorbent core is an airlaid material. The absorbent core 122 may have other properties including extensibility, which will allow the absorbent core to be extended or fit to a particular wearer. One example of extensible absorbent cores is described in U.S. Pat. No. 5,611,790, issued Mar. 18, 1997, to Osborn, III et al., herein incorporated by reference in its entirety.

In one embodiment, the absorbent core 122 may also include a superabsorbent material, in addition to or in place of the hydrophilic material, which increases the ability of the absorbent core to absorb a large amount of fluid in relation to its own weight. Generally stated, the superabsorbent material can be a water-swellable, water-insoluble, hydrogel-forming polymeric absorbent material, which is capable of absorbing at least about 15 times, suitably about 30 times, and possibly about 60 times or more its weight in physiological saline (e.g., saline with 0.9 wt % NaCl). The superabsorbent materials can be inserted as particles or in sheet form. The superabsorbent material may be biodegradable or bipolar. The hydrogel-forming polymeric absorbent material may be formed from organic hydrogel-forming polymeric material, that can include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers, and mixtures thereof. The hydrogel-forming polymers may be lightly crosslinked to render the material substantially water insoluble. Crosslinking may, for example, be by irradiation or covalent, ionic, Van der Waals, or hydrogen bonding. Hydroxyfunctional polymers have been found to be good superabsorbents for sanitary napkins. Such superabsorbents are commercially available from Dow Chemical, Hoechst-Celanese, and Stockhausen, Incorporated, among others, and are a partially neutralized salt of cross-linked copolymer of polyacrylic acid and polyvinyl alcohol having an absorbency under load value above 25 grams of absorbed liquid per gram of absorbent material (g/g). Other types of superabsorbent materials known to those skilled in the art can also be used.

The generally liquid impermeable backsheet 123 is present in the absorbent structure 121 to prevent fluid entering the absorbent core 122 from flowing through the absorbent core 122 and onto a garment or undergarment being worn by a wearer. Suitable liquid impermeable backing sheets include, for example, a polymeric film, a woven fabric, a nonwoven fabric or the like, as well as combinations or composites thereof. Generally, any material that may be used as the shell material describe above may be used as the backsheet 123 of the absorbent structure 121. The liquid impermeable backsheet 123 may be a polymeric film, a woven fabric, a nonwoven fabric or the like, as well as combinations or composites thereof. For example, the liquid impermeable backsheet 123 may include a polymer film laminated to a woven or nonwoven fabric. The polymer film can be composed of polyethylene, polypropylene, polyester, silicone or the like, as well as combinations thereof. Additionally, the polymer film may be micro-embossed, have a printed design, have a printed message to the consumer, and/or may be at least partially colored. Suitably, the liquid impermeable backsheet 123 can operatively permit a sufficient passage of air and moisture vapor out of the absorbent article 100, particularly out of an absorbent structure 121 while blocking the passage of bodily fluids and odors often associated with bodily fluids. An example of suitable materials for the liquid impermeable backsheet 123 can include a breathable, microporous film, such as those described in, for example, U.S. Pat. No. 6,045,900 to Haffner et al., the entire disclosure of which is incorporated herein by reference and made a part hereof.

The side of the backsheet 123 that faces the undergarment or garments of a wearer should have a low coefficient of friction for the same reasons that the second side 117 of the shell should have a low coefficient of friction. This will allow the garment facing side of the backsheet 123 to move freely against the undergarment or clothing of a wearer. If the garment facing side of the backsheet 123 does not freely move against the undergarment or other clothing worn by the wearer, the absorbent article may catch on the undergarment or clothing, which may result in the absorbent article or the absorbent structure being prematurely and undesirably removed from the wearer or may cause the absorbent article to be shifted from its desired placement against the body of a wearer. In addition by having both the garment facing side of the backsheet 123 and the second side 117 of the shell freely move against the undergarment or clothing of the wearer, the body attached absorbent article will be comfortable for a wearer to wear and may provide improved protection since the undergarment or clothing will not cause the absorbent article to shift during use.

Generally, the absorbent structure will be positioned adjacent to the second side 117 of the shell 114, as can be seen in FIGS. 1-6. By "adjacent to the shell", it is meant that the absorbent structure 121 is directly in contact with the second side 117 of the shell 114 or may be separated by one or two additional layers or a construction or pressure sensitive adhesive. The absorbent structure should be positioned such that the absorbent core 122 is beneath the opening 105 so that any fluid flowing through the opening 105 will come into contact with the absorbent core 122.

In addition to the absorbent core 122, the absorbent structure 121 may have other additional layers that aid the absorbent core 122 in capturing and holding the bodily fluid into the absorbent core 122. These other layers, when present and in combination with the absorbent core 122, form the absorbent structure 121 of the absorbent article 100. There may be a single layer or multiple layers in addition to the absorbent core 122 in the absorbent structure 121.

One particular example of an additional layer which may be used in addition to the absorbent core 122 in the absorbent structure 121 is a top sheet 124, which is generally a liquid permeable material, that allows bodily fluids to pass through the top-sheet into the absorbent core. The top sheet 124 also may provide a wearer with a dry feeling by separating the absorbent core 122 from the body of the wearer. That is, the top sheet 124 is placed between the absorbent core 122 and the body of the wearer such that the absorbent core 122 is between the top sheet 124 and the shell 114.

Optionally, the top sheet 124 may be formed from one or more materials. The top sheet 124 should be able to manage different body excretions depending on the type of product. In feminine care products, often the top sheet 124 must be able to handle menses and urine. In addition, the top sheet 124 may be comfortable, soft, and friendly to the wearer's skin. The top sheet 124 may include a layer constructed of any operative material, and may be a composite material. For example, the top sheet can include a woven fabric, a nonwoven fabric, a polymer film, a film-nonwoven fabric laminate or the like, as well as combinations thereof. Examples of a nonwoven fabric useable in the top sheet 124 include, for example, an airlaid nonwoven web, a spunbond nonwoven web, a meltblown nonwoven web, a bonded-carded web, a hydroentangled nonwoven web, a spunlace web or the like, as well as combinations thereof. Other examples of suitable materials for constructing the top sheet 124 can include rayon, bonded-carded webs of polyester, polypropylene, polyethylene, nylon, or other heat-bondable fibers, finely perforated film webs, netlike materials, and the like, as well as combinations thereof. These webs can be prepared from polymeric materials such as, for example, polyolefins, such as polypropylene and polyethylene and copolymers thereof, polyesters in general including aliphatic esters such as polylactic acid, nylon or any other heat-bondable materials. When the top sheet is a film or a film laminate, the film should be apertured or otherwise be made to allow fluids to flow through the top sheet to the absorbent core.

Other examples of suitable materials for the top sheet 124 are composite materials of a polymer and a nonwoven fabric material. The composite materials are typically in the form of integral sheets generally formed by the extrusion of a polymer onto a nonwoven web, such as a spunbond material. In a particular arrangement, the top sheet 124 can be configured to be operatively liquid-permeable with regard to the liquids that the article is intended to absorb or otherwise handle. The operative liquid-permeability may, for example, be provided by a plurality of pores, perforations, apertures or other openings, as well as combinations thereof, which are present or formed in the liner or body contacting layer. The apertures or other openings can help increase the rate at which bodily liquids can move through the thickness of the liner or body contacting layer and penetrate into the other components of the article (e.g., into the absorbent core 122). The selected arrangement of liquid permeability is desirably present at least on an operative portion of the top sheet 124 that is appointed for placement on the body-side of the article. The top sheet 124 can provide comfort and conformability, and can function to direct bodily exudates away from the body and toward the absorbent core 122. The top sheet 124 can be configured to retain little or no liquid in its structure, and can be configured to provide a relatively comfortable and non-irritating surface next to the body tissues of a wearer. The top sheet 124 positioned over the absorbent core may have a surface which is embossed, printed, or otherwise imparted with a pattern.

Additional layers or substrates, such as, a liquid acquisition and distribution layer, also referred to as a surge or transfer layer, and an optional tissue layer can be incorporated into the absorbent structure 121 of the absorbent article 100 between the top sheet 124 and the absorbent core 122. The distribution layer may be shorter than the absorbent core 122 or have the same length as the absorbent core. The distribution layer serves to temporarily hold an insulting fluid to allow the absorbent core sufficient time to absorb the fluid, especially when a superabsorbent material is present.

In another embodiment, the absorbent core, transfer layer, and other components, such as tissue layers, may be free floating (unattached) between the shell 114 and the top sheet 124, and only are secured along only the peripheral edges thereof. Alternatively, the absorbent core 122, transfer layer, if present, and any other layer or component, if present, may be attached to one or both of the second side 117 of the shell 114 and top sheet 124 and/or to each other.

The absorbent structure 121, including the absorbent core 122, is generally attached to the second side 117 of the shell 114, such that the absorbent core is positioned under the opening 105 in the shell. The absorbent structure 121 may be attached to the shell 114 in a permanent manner, meaning that the absorbent structure is generally intended not to be removable by the wearer of the absorbent article 100. Alternatively, the absorbent structure 121 may be made to be removably attached to the shell, such that the absorbent structure 121 may be removed by a wearer of the absorbent article 100 and replaced with the same absorbent structure 121 or with another new absorbent structure 121. When the absorbent structure 121 is attached to the shell 114 in a permanent manner, meaning that the absorbent structure is not intended to be removed by the wearer, a construction adhesive may be used. The construction adhesive include any adhesive that will effectively hold the absorbent structure 121 in place, so as not to be separated from the shell 114. Commercially available construction adhesives usable in the present invention include, for example Rextac adhesives available from Huntsman Polymers of Houston, Tex., as well as adhesives available from Bostik Findley, Inc, of Wauwatosa, Wis. Other means may be used to hold the absorbent structure 121 to the shell, including heat bonding, ultrasonic bonding, or other similar mechanical attachments.

When the absorbent structure 121 is removably attached, the absorbent structure 121 is held in place to the second side 117 of the shell 114 by a means that will allow the wearer to remove the absorbent structure. One such means of holding the absorbent structure is by using a pressure sensitive adhesive. Suitable pressure sensitive adhesives include any commercially available pressure sensitive adhesive. Examples of suitable pressure sensitive adhesives usable to removably hold the absorbent structure 121 in place on the second side 117 of the shell 114 include pressure sensitive adhesives available from National Starch and, having offices in Bridgewater, N.J. 08807. By providing an absorbent structure 121 that is removable, the shell 114 may be reused several times. That is, the shell 114 does not need to be replaced when the absorbent structure is replaced. Other means, such as mechanical attachment may also be used to removably attach the absorbent structure 121 to the shell 114. By having a removable absorbent structure 121, the absorbent structure can be selected by the wearer prior to use. This would allow the wearer to select an appropriate level of protection for a given day or allow the wearer to select a size or shape of the absorbent that the wearer finds to be more comfortable. When the absorbent structure 121 is removable, and adhesively attached to the shell 114, the adhesive could be designed to remain on the shell or remain only on the absorbent structure. Generally, the adhesive should be placed on the absorbent structure 121 since this will provide fresh adhesive to hold the new absorbent in place each time the absorbent structure 121 is replaced. If the adhesive is present on the absorbent structure 121, a release sheet may be place over the adhesive so that the adhesive is not contaminated with dirt or debris that may have an adverse effect in holding the absorbent structure 121 to the shell 114.

To aid a wearer in replacing the absorbent structure 121, a placement aid may be present on the shell 114 and/or the absorbent structure. Suitable placement aids include the use of color, tactile indicators, or any other means that would assist the wearer in replacing a removed absorbent structure.

Figure 7:
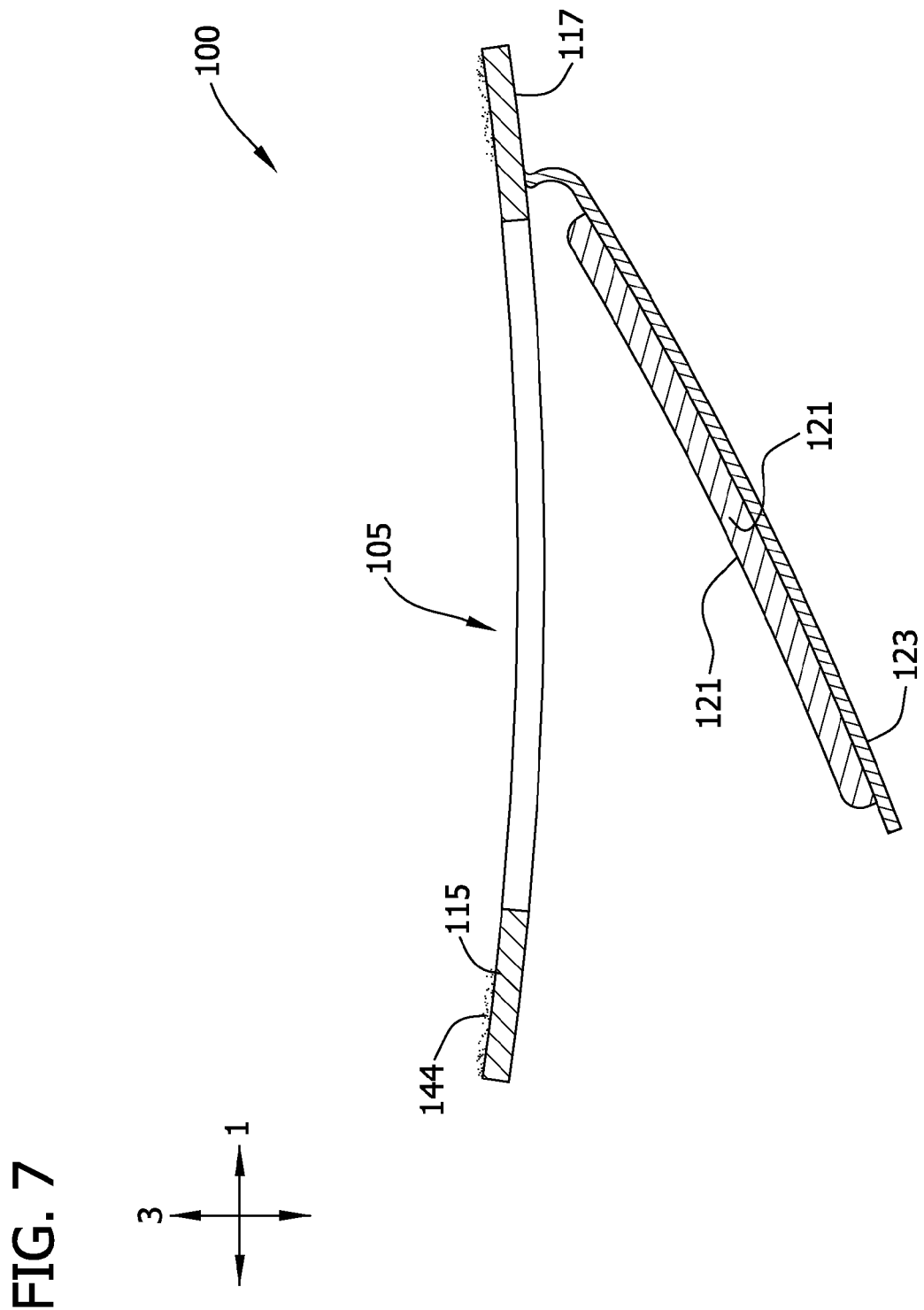
FIG. 7 shows a cross-sectional view of an embodiment of an absorbent article of the present invention having a hinged absorbent structure.

By having the absorbent that is removable, a wearer could remove the absorbent structure, urinate and then replace the absorbent structure. This would alleviate the need of a wearer to have to replace the entire absorbent article 100 in order to form bodily functions. As another alternative, the absorbent structure 121 can be hingely attached to the shell by a hinging means, as seen in FIG. 7.

The absorbent structure 121 may be a relatively flat structure, as shown in FIG. 6 or the absorbent structure 121 may be curved to match the shape of the shell 114, as seen in FIG. 5. The size, location, and shape of the absorbent structure 121 may also be selected for an intended use. For example, in an overnight use, the absorbent may be located further back on the wearer towards the perinea region of the wearer. In an overnight use, the absorbent structure may be larger than in a product intended for daytime use. In a daytime use, the absorbent structure will generally be centrally located in the vulva region.

In another embodiment, the shell 114 material may also be provided with some absorbency in addition to the absorbent structure 121. One way to achieve absorbency in the shell is to have the shell 114 prepared from a material that is a laminate of two or more materials. The first side 115 of the shell 114 contains an absorbent material within the body facing side of the laminate. For example, superabsorbent particles or materials may be incorporated into the material making up the body facing layer of the laminate. Another way is to place a very light coating onto the first side 115 of the shell material, wherein the coating contains a superabsorbent particles or materials. Of course other absorbent materials, other than superabsorbent materials may be used in place of or in addition to the superabsorbent materials.

The absorbent core 122 of the absorbent structure 121 may be located entirely within the opening 105 in the shell 114, or the absorbent core 122 of the absorbent structure may extend past the opening 105 in the shell, as seen in FIGS. 5 and 6, meaning that a portion of the absorbent core 122 contacts or is facing the second side 117 of the shell 114. Alternatively, the absorbent structure 121 may extend past the ends 104, 104' of the shell 114 or the second region 107 of the shell.

The liquid backsheet 123 may be a polymeric film, a woven fabric, a nonwoven fabric or the like, as well as combinations or composites thereof. For example, the liquid backsheet 123 may include a polymer film laminated to a woven or nonwoven fabric. In a particular feature, the polymer film can be composed of polyethylene, polypropylene, polyester, silicone or the like, as well as combinations thereof. Additionally, the polymer film may be micro-embossed, have a printed design, have a printed message to the consumer, and/or may be at least partially colored. Suitably, the liquid backsheet 123 can operatively permit a sufficient passage of air and moisture vapor out of the absorbent article 100, particularly out of an absorbent structure 121 while blocking the passage of bodily fluids and odors often associated with bodily fluids. An example of a suitable material for the liquid backsheet 123 can include a breathable, microporous film, such as those described in, for example, U.S. Pat. No. 6,045,900 to Haffner et al., the entire disclosure of which is incorporated herein by reference and made a part hereof. Other materials that may be used in preparing the backsheet 123 include materials which are inherently breathable, such as polyurethanes.

As is stated above, the first side 115 of the shell 114 either directly or indirectly attaches to the body of a wearer. Stated another way, the shell is the body attachment member and the first area 115 is the portion of the shell 114 that is attached to the body of the wearer. Depending on the material selected for the shell, the shell may actively attach to the body of the wearer using electrostatic mean, suction means, or a body adhesive may be placed on the first side 115 of the shell 114 to attach the absorbent article to the body of a wearer. Electrostatic means that can be used is by selecting the shell material to be a material that has an affinity for the body of a wearer, such that the shell material "clings" to the body of the wearer. Examples of such materials include ethylene vinyl acetate, low density polyethylene and other similar materials know to those skilled in the art. Suction means may be achieved by shaping the shell to conform to the body of the wearer, much like a contact lens fits to the eye. Generally, suction means can be achieved by forming the shell 114 into a three-dimensional shape. The easiest way, however, to achieve body attachment is to place a body adhesive in the first side 115 of the shell 114.

A body adhesive 144 is positioned on the first side 115 of the shell 114. The body adhesive 144 contacts the skin and hair, if present, in the vulva region and possibly the pubic region and/or the perinea region of the wearer's body, thereby supporting and holding the absorbent article 100 against the body of the wearer during use. The body adhesive 144 can overlie a portion of the first side 115 or can overlie the first side 115 of the shell 114. Generally, the body adhesive 144 will be present on at least the outer portion first side of the shell near the edge 120 of the absorbent article 100. The adhesive may cover the entire first side 115 of the absorbent article (not shown in the drawings). Alternatively, the body adhesive 144 may be placed on a portion of the first side, as seen in FIGS. 1 and 2. The body adhesive 144 may also be placed in a pattern of the first side 115 of the absorbent article. The body adhesive 144 can be applied to the first side 115 of the shell 114 of using any known process including inkjet printing, screen printing, or extruding the body adhesive 144 from one or more nozzles, slot coating and the like.

Generally, any pressure sensitive adhesive known to those skilled in the art may be used, provided that the pressure sensitive adhesive is not a known irritant to human skin or that the adhesive is so aggressive that it causes pain to the wearer when the absorbent article is removed from the skin. It is also desirable that the adhesive is selected such that the adhesive does not leave a substantial amount of residue on the skin of the wearer, when the absorbent article 100 is removed. Particularly suitable pressure sensitive adhesive materials are disclosed in the commonly assigned U.S. Pat. No. 6,213,993 to Zacharias et al., U.S. Pat. No. 6,620,143 to Zacharias et al., the entire disclosure of each is incorporated herein by reference and made a part hereof. Other suitable adhesives are disclosed in U.S. Pat. No. 5,618,281 to Batrabet et al., the entire disclosure of which is incorporated herein by reference and made a part hereof. Other known body adhesives, such as those described in U.S. Pat. No. 6,316,524 to Corzani et al. which is hereby incorporated in its entirety, may also be used. Additional examples of pressure sensitive adhesives include hydrogels, hydrocolloids, acrylics based adhesives, and rubber based adhesives, such as Kraton based adhesives.

The body adhesive 144 may be positioned on the first side 115 of the shell 114 in an open pattern or a closed pattern. By "open pattern" is meant that the adhesive can have an intermittent or discontinuous pattern that does not substantially encircle the entire opening 105. For example, there may be breaks in the body adhesive at certain portions of the first side 115. "Closed pattern" means the adhesive 144 would encircle the entire opening 105 in the shell. In one embodiment, the pattern of the body adhesive 144 will substantially surround the cover of the first side 115 and substantially surround the opening 105. An example of an "open" pattern of the adhesive would be to have individual beads of adhesive applied in a discontinuous fashion. The closed pattern can be advantageous since the body adhesive 144 may form a seal with the body of the wearer which will assist in preventing leaks from the absorbent article 100. The body adhesive may form a dam, which may prevent leaks from the entire perimeter of the absorbent article 100.

In one embodiment, the body adhesive 144 may be placed on the entire first side 115 of the shell 114, as seen in FIG. 1. In another embodiment, as seen in FIG. 2, the body adhesive 144 may placed along the outer portions of the first side 115 near the periphery of the shell 114, such that no adhesive is near the opening 105. The body adhesive 144 may also be placed on the absorbent structure 121 positioned on the second side 117 of the shell 114 to help hold the absorbent article in place on the wearer. Generally, however, the body adhesive 144 is confined to being placed on the first side 115 of the shell 114, since placing the body adhesive on an area of the absorbent product 100 that contacts the female genitalia such as the labia majora may cause discomfort to the wearer of the absorbent product 100.

The adhesive may be applied in a pattern of small discrete dots so as to leave numerous areas free from adhesive. Alternatively, the adhesive may be applied as a continuous bead, or may be applied as a series of semi-continuous beads. Other suitable adhesive patterns may be selected for applying the body adhesive 144 to the body-contacting first side 115 of the absorbent article 100. For example, adhesive patterns can be oval, swirls, various linear or non-linear arrays of adhesive longitudinally, and/or transversely oriented and reticulated webs having unobstructed interstices between the adhesive fibers or combinations thereof. As stated above, the adhesive patterns may be open or closed. The weights of adhesives are limited to less than about 800 grams per square meter ($g/m^2$), and generally less than about 400 $g/m^2$. Generally, the weight of the adhesive is at least 20 $g/m^2$. Typically, the adhesive is applied in an amount of about 100 $g/m^2$ to about 400 $g/m^2$. The limitations on the basis weight of the adhesive are important to provide the correct adhesive characteristics for applying directly to the wearer's vulva region and optionally the pubic and perinea regions of the wearer's body. If the basis weight is too high, the absorbent article will have a sticky feeling or otherwise uncomfortable feeling. If the basis weight of the adhesive is too low, there may be insufficient adhesion to the body of the wearer.

Generally, the body adhesive 144 is applied in a manner that is symmetrical about the longitudinal axis that bisects the absorbent article 100 and divides the absorbent article 100 into substantially equal portions. This symmetrical pattern provides the wearer a balanced feel when wearing the absorbent article 100. The symmetrical pattern also reduces the perception of any associated discomfort when the absorbent article 100 is removed from the body.

Figure 8A:
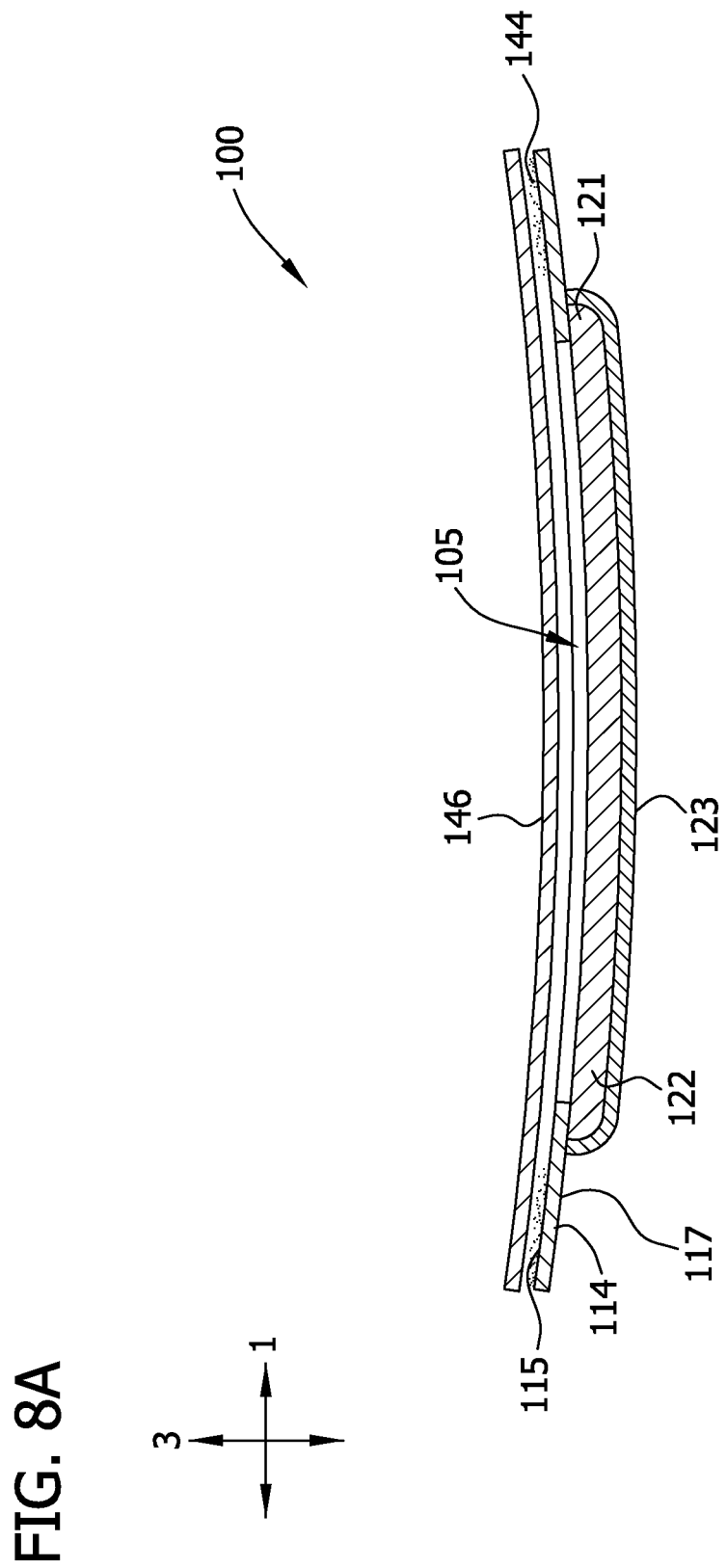

As seen in FIGS. 8A and 8B, to protect the body adhesive 144, a peel sheet or release sheet 146 may be used to prevent the body adhesive 144 from becoming contaminated, thus loosing its ability to stick to the body of an wearer and/or prematurely adhering to an unintended surface. Suitable materials for use as the release strip 146 are well known in the art and are commercially available. Examples of suitable release sheets 146 include, a silicone coated Kraft paper, a silicone coated film or the like. Other release coatings include coatings containing polytetrafluoroethylene. The release sheet 146 may extend beyond one or both of the ends and/or sides of the shell, as shown in FIG. 8B. Alternatively, the release sheet 146 may be sized to only cover the body adhesive on the first side 115 of the shell 114, as seen in FIG. 8A. In yet another embodiment, the release sheet 146 may extend beyond the adhesive at one or more locations, such as one of the ends or one of the sides of the shell as seen in FIG. 8C by providing the release sheet 146 with a tab 147 for the wearer to grasp to remove the release sheet 146 from the absorbent article 100 and the body adhesive 144 on the absorbent article 100. When the release sheet 146 extends beyond the adhesive, it is generally easier for the wearer to remove the release sheet to place the absorbent article 100 for use.

Alternatively, the release sheet 146 may be provided with a pressure sensitive adhesive to hold the release sheet 146 in place when the absorbent article is devoid of an adhesive for body attachment. In this configuration, the release sheet 146 serves to protect the absorbent structure and first side of the shell from dirt and damage prior to use.

In another embodiment, the release sheet 147 may not be necessary. For example, the absorbent article may be rolled, folded onto itself or stacked upon each other. In these configurations, a release sheet is not needed. If rolled, the body adhesive 144 will generally contact the second side 117 of the shell 114 or the liquid impermeable backsheet 123 of the absorbent structure. The body adhesive 144 should releasably stick to one second side of the shell by readily releasing when unrolled by the wearer or wearer. In addition, the body adhesive 144 should not leave a residue on the second side 117 of the shell 114, of the backsheet 123. This should similarly occur when the absorbent articles 100 are stacked upon each other such that the body adhesive 144 of one article will attach the second side 117 of the shell and/or backing sheet of a second article. In another possible configuration, the absorbent article 100 may be folded along the longitudinal axis 1 of the lateral axis such that the body adhesive 144 in one area comes into contact with body adhesive in another area. In the folded configuration, the body adhesive should be selected such that the body adhesive will release from itself when manipulated by a wearer.

The dimensions and shape of the shell 114 should be such that it is appropriately sized for its intended use. The same is true for the size and shape of the absorbent structure 121 and the size of the opening 105. Generally, the size and shape of the absorbent structure 121 will dictate the size of the shell 114. The shape of the shell 114 is selected so that the absorbent article will have a comfortable feeling for the wearer, thereby providing protection against leaks and preventing the absorbent article from becoming dislodged from the body of the wearer during use. Generally, the shell 114 will be curved to fit the body of a wearer. The shell 114 also generally gives the absorbent article 100 its overall size and shape in the longitudinal 1 and lateral 2 directions. That is, the shell is generally longer and wider than the absorbent structure, as can be seen in the figures. In other words, the shell 114 will be wider in the lateral direction 2 than the absorbent structure 121, and the shell will be longer in the longitudinal direction 1 than the absorbent structure 121. As is mentioned above, it is possible for the absorbent structure 121 to be longer than the shell 114 but it is not generally wider.

When the absorbent article 100 is intended for use as a pantiliner, a sanitary napkin, or a feminine incontinence article, the shell 114 should be wider and longer than the absorbent structure 121 attached to the second side 117 of the shell 114. The opening 105 in the shell 114 should generally be at least as wide and as long as the labia majora of the wearer. This will prevent the shell 114 from contacting the sensitive parts of a wearer's body. The absorbent structure 121 should be as large as or larger than the opening 105. As a result, to fit most women, the absorbent structure 121 is longer in the longitudinal direction 1 than it is wide in the lateral direction 2 of the absorbent structure. Generally, for most women, the labia majora are generally between about 40 millimeters (mm) and about 70 mm in width and between about 80 mm and 150 mm in length. Ideally, the absorbent structure 121 and opening 105 should be wider than the labia majora and slightly longer than the labia minora and slightly longer than or equal to the labia majora. Generally, the absorbent structure 121 and opening 105 should be between about 40 mm and 90 mm in width in the lateral direction 2 and between about 95 mm and about 150 mm in length in the longitudinal direction 1. The shape of the absorbent structure 121 and opening 105 will generally tend to be oblong and may be an oval, a rectangle, tear drop shaped, hourglass shaped or racetrack shaped. As can be seen in FIGS. 1 and 2, the absorbent structure 121 may be generally elliptical or oval in shape to match the size and shape of the vaginal area of most women.

Generally, the shape of the shell 114 may vary from a general oval, as shown in FIGS. 2 and 4, to a shape that is generally hourglass-like, shown in FIGS. 1 and 3. By generally hourglass-like, it is meant shape in which the sides 119 of the shell 114 converge towards one another at a point along the longitudinal axis of the shell 114 to form a narrowest portion 133 of the absorbent article 100. Generally, the hourglass-like shape provides a cut-out for the wearer's legs. By having an hourglass-like shape, the shell 114 will not be attached to the legs of a wearer during use. This will provide more comfort for the wearer of the absorbent article 100. The shape of the shell 114 should be selected such that the absorbent article 100 will be comfortable to wear, while providing very effective leakage protection to the wearer. The shell 114 and the absorbent structure 121 should be able to adapt to the curvature of a wearers body during use. Other possible shapes for the shell 114 not specifically shown may also be used, provided that the shape will provide comfort to the wearer of the absorbent article.

To obtain an effective attachment of the absorbent article to the wearer, when the absorbent article is used as a sanitary napkin or an incontinence article, generally the width of the of the shell should be at least 10 mm on either side of the labia majora. Generally, the shell 114 of the absorbent article 100 will have a width, in the lateral direction 2, between about 50 mm up to 200 mm or more. Typically, the shell will be between about 60 and 120 mm at its narrowest point. This will allow the shell 114 to have a first side 115 that can be effectively attached to the skin of a wearer on either side of the labia majora.

In addition, the absorbent article 100 may also be configured to have an anterior region 164, a central region 165, and a posterior region 166, as seen in FIG. 1. As used herein, the term "anterior" refers to the direction towards the front of the wearer during use. As used herein, the term "posterior" refers to the direction towards the back of the wearer during use. A particular embodiment is shown in FIG. 1 of an absorbent article having a configuration designed to fit specific areas of the vulva region of a wearer. By providing specific portions for attachment to specific areas of the body of the wearer, the absorbent article may be configured to better fit the body of the wearer. The anterior region 164 of the absorbent article will be the portion of the absorbent article between the absorbent structure 121 and the first end 161 of the absorbent article 100. The posterior region 166 of the absorbent article 100 will be the portion of the absorbent article between the absorbent structure 121 and the second end 162 of the absorbent article 100. Generally, the posterior region 166 will be designed to be placed between the vagina area and the anal area of the wearer. The anterior region 164 is designed to be placed on the mons Veneris region of a female wearer. The central region 165 of the absorbent article 100 is designed to cover the vagina area of the wearer and the skin area surrounding the lateral sides of the labia majora, when the absorbent article is used as a pantiliner, sanitary napkin, or an incontinence article. In an alternative use, the absorbent article of the present invention may also be used as an underwear replacement, or a guard for a swimming suit.

Figure 9A:
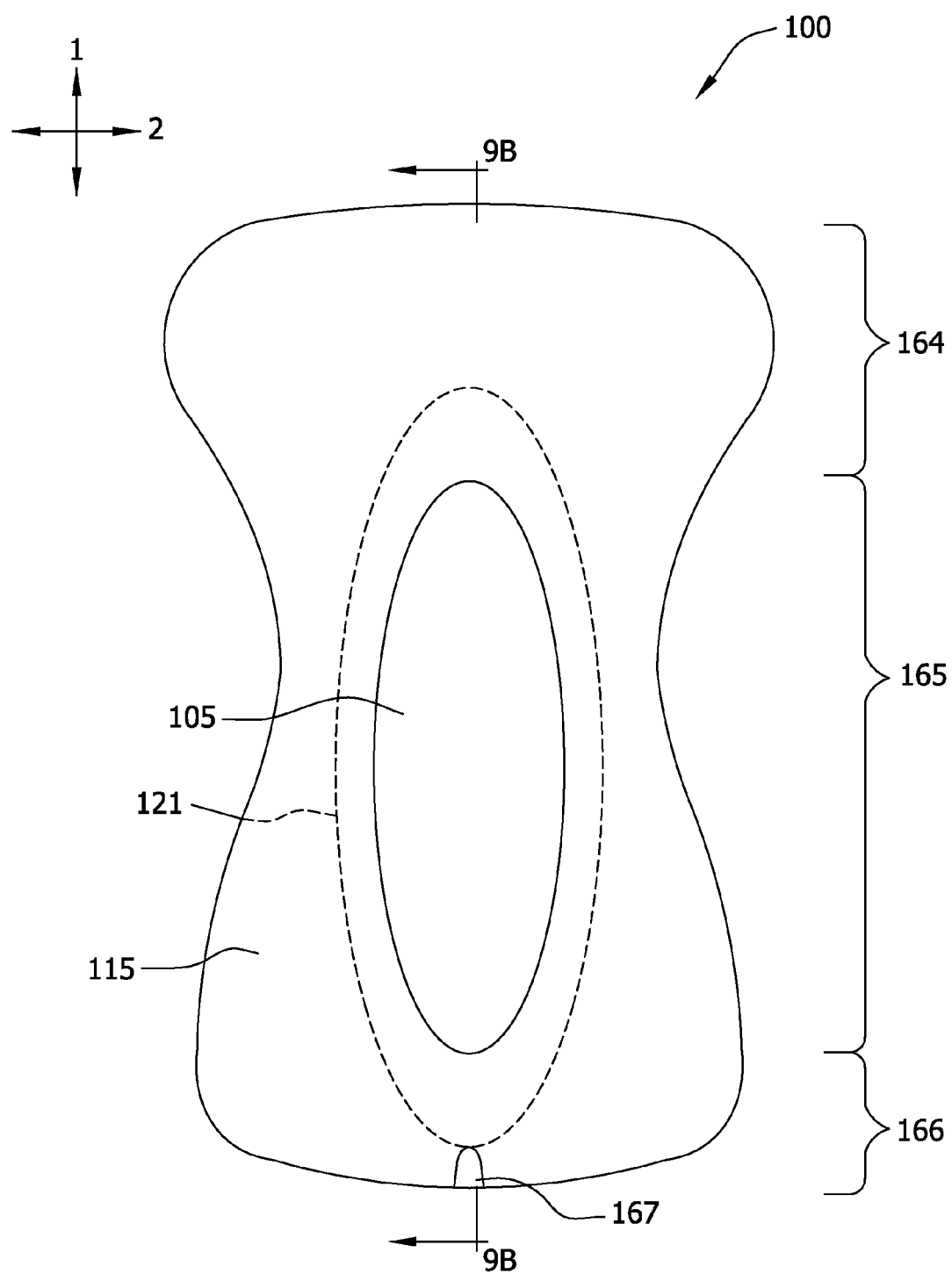
FIG. 9A shows a top view of another absorbent article of the present invention having a design for attachment to the wearer's body.

To obtain an effective attachment to the body of the wearer, the shell 114 can be configured to be anatomically correct for a wearer. As seen in FIG. 9A, the shape of the absorbent article 100 is such that it will correctly and securely fit in the vulva region of a wearer. The general shape of the absorbent article shown in FIG. 9A has been found to effectively attach to the vulva region of female wearers of the absorbent article. Additional features may be included to ensure an anatomically correct shape. For example, in the posterior region of the absorbent article 100, more particularly, the posterior region of the shell on the first side 115, the shell 114 may be imparted with a three-dimensional protrusion 167, as shown in FIGS. 9A and 9B. The protrusion 167 acts to fit comfortably in the perinea region of the wearer. The protrusion 167 may be formed from the shell material or may be formed from the body adhesive 144. By providing the three-dimensional protrusion 167, the absorbent article 100 can effectively fit to the typical body shape of the female wearer, thereby preventing leaks from the posterior region of the absorbent article. The protrusion 167 may also serve as a guide to the wearer in placement of the absorbent article 100 on the body of a wearer prior to use.

Figure 10A:
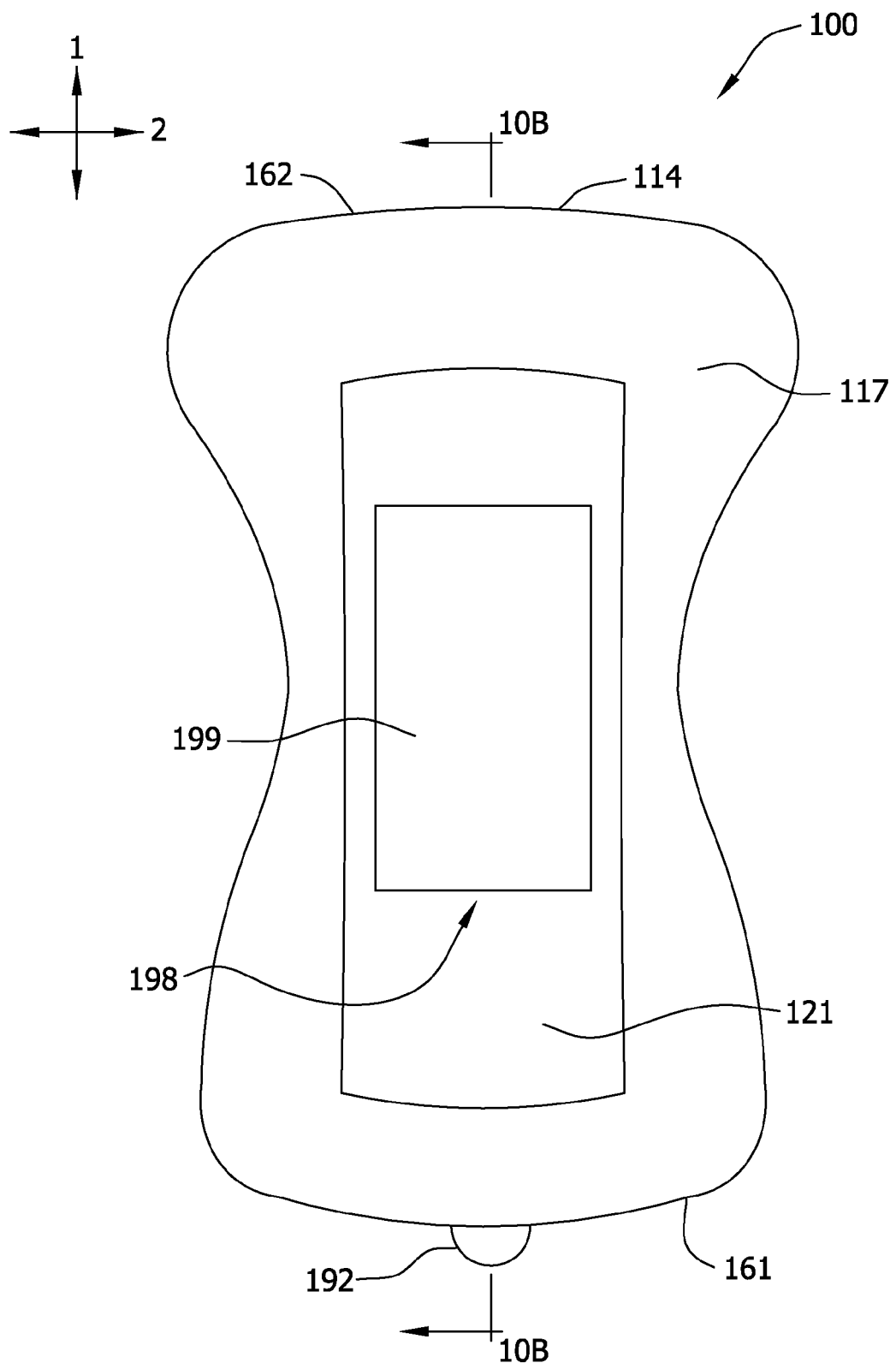
Figure 11:
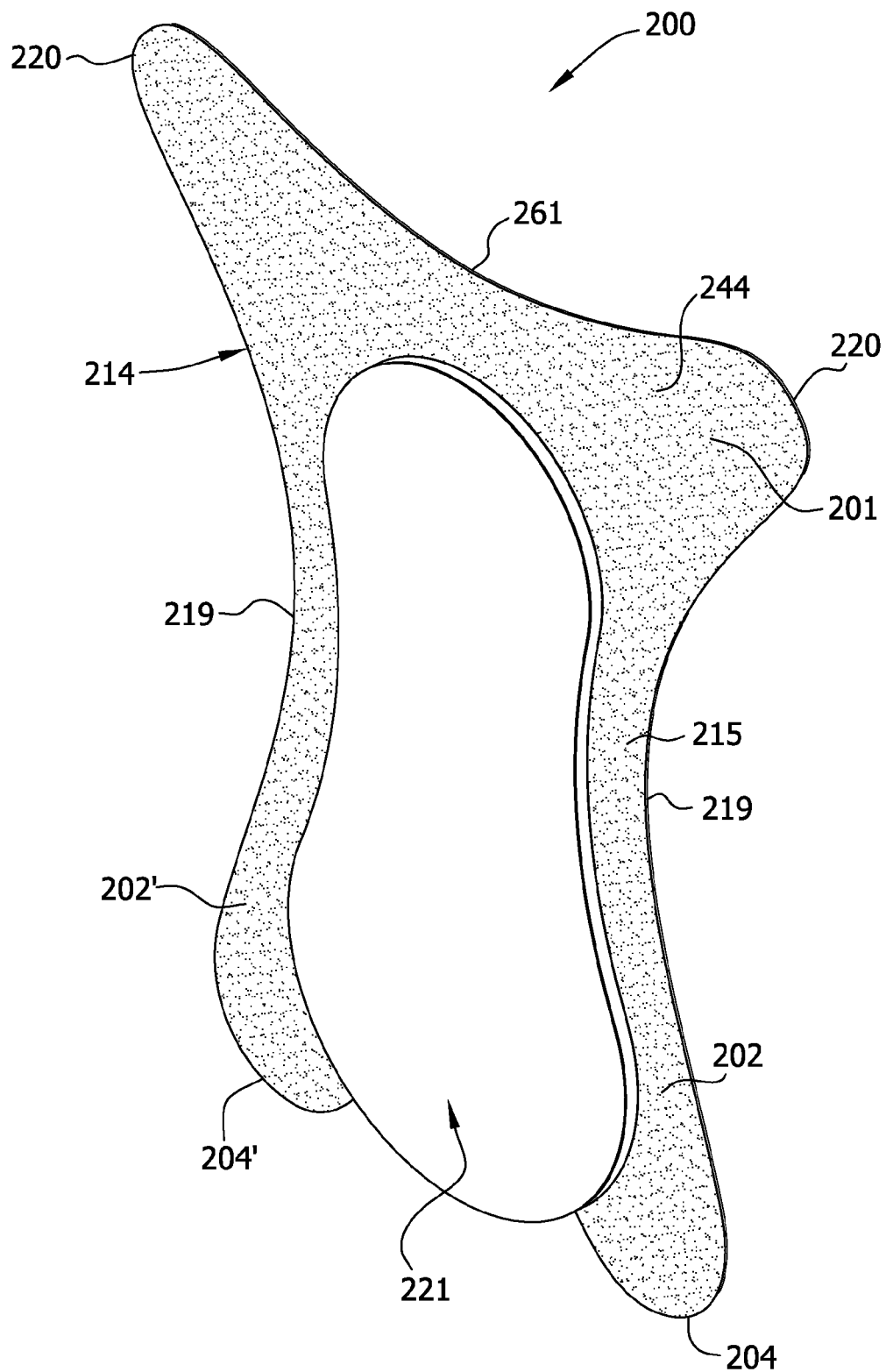
FIG. 11 shows a perspective view of another embodiment of an absorbent article of the present invention.
Figure 12:
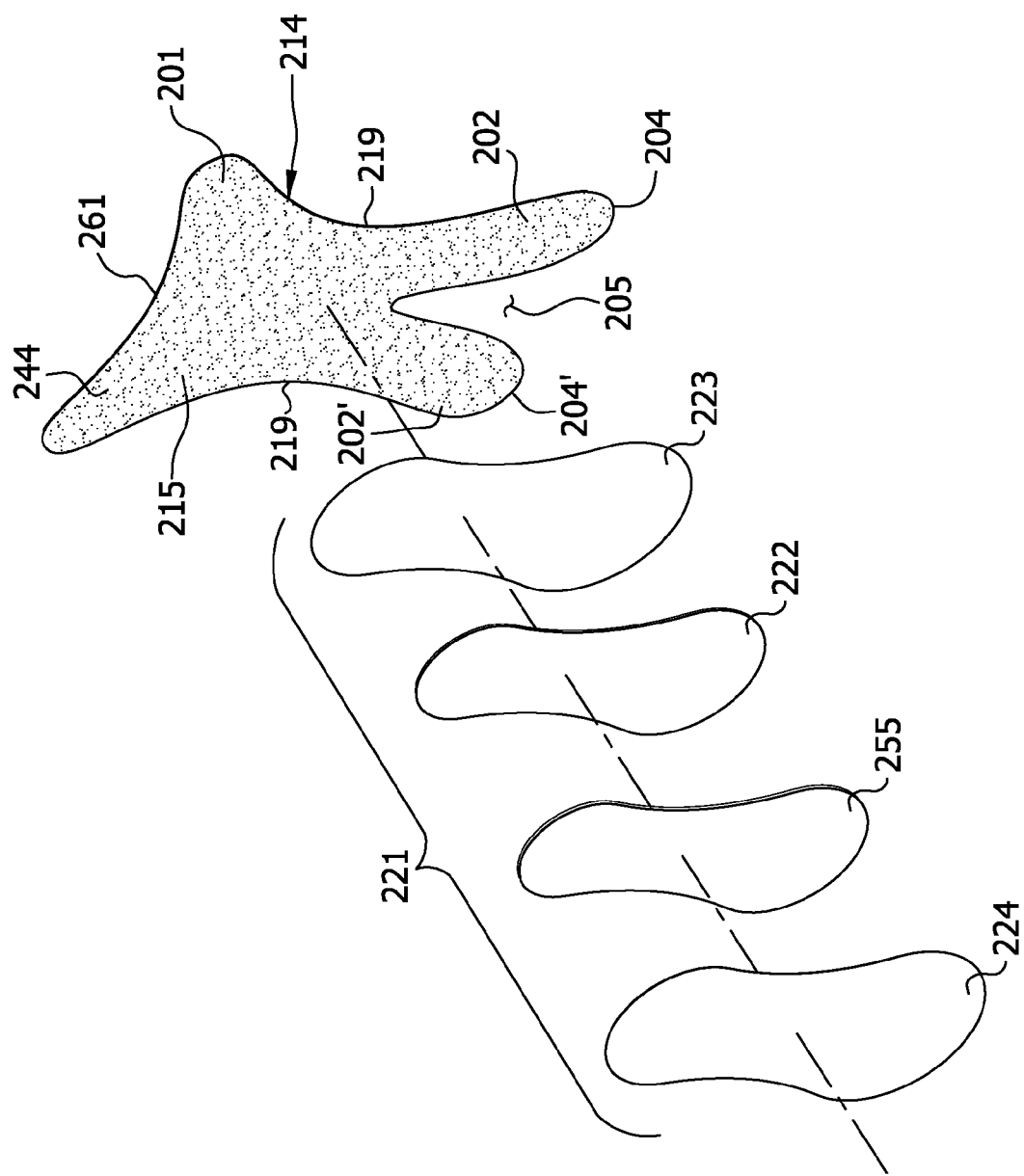
FIG. 12 shows an exploded perspective of the absorbent article.

The absorbent article 100 of the present invention may have other features that aid the wearer in placing and removing the absorbent article from the body. As seen in FIGS. 10A and 10B, the second side 117 of the shell 114 or the backsheet 123 may be provided with positioning aids such as a finger pocket 199 or finger grooves in the shell 114 (not shown) material or backsheet 123 of the absorbent structure 121. Generally, the finger pocket 199 has an opening 198 positioned such that a wearer inserts their fingers towards the posterior region 166 or second end 162 of the absorbent article 100. The pocket 199 gives the wearer a location to place her fingers during placement of the absorbent article 100 onto the wearer's body. The pocket 199 may be an opening wide enough for the wearer to place at least two fingers in the pocket. Alternatively, there may be two or more openings which allow the wearer to place only one finger in each opening. Other similar positioning aids may be used to help guide a wearer to properly place the absorbent article for use. For example, grooves may be placed in the second side 117 of the shell 114 or backsheet 123 of the absorbent structure. This may allow the wearer to feel the location of the absorbent structure relative to the vulva region during application of the absorbent article 100 to the vulva region of the body. The pocket 199 may also assist the wearer in removing the absorbent article from their body or removing the absorbent structure when it needs to be replaced.

The absorbent article 100 may also be provided with a removal aid which provides the wearer with an easy way to grasp and remove the absorbent article applied to the body. One particular removal aid is shown in FIG. 10A including a tab 192 located on the first end 161 of the shell that is not adhered to the body or is devoid of adhesive. Alternatively, other removal aids, such as having an area of the first end 161 being devoid of the body attaching adhesive 144 may be used. Other types of removal aid that may be present include loops and pull strings. The removal aid allows the wearer to effectively begin the process of gently removing the absorbent article from the body of the wearer without the need of having to find a portion of the shell that may not be completely attached.

Other features or additives may be incorporated into the absorbent article. For example, the absorbent article may contain an odor control agent, or a fragrance, skin wellness agents, and other similar additives used in currently available absorbent articles. Any odor control agent or fragrance known to those skilled in the art may be used in the absorbent article 100. The odor control agent or fragrance may be added in various components of the absorbent article, including the shell 114, the absorbent structure 121, or the body adhesive 144. Skin wellness additives may be added onto the absorbent structure, any portion of the first surface 115 of the shell 114 attached to the wearer or in the body adhesive 144.

Generally, to apply the absorbent article 100 to the body of a wearer, the release sheet 146, protecting the absorbent structure and adhesive, if present, is removed from first surface of the shell. Next, the wearer positions the absorbent structure of the portion of the body in which absorbency is needed. If positioning pockets or other positioning aids are present on the absorbent structure, the wearer may optionally use these positioning aids to properly place the absorbent article for use. In the case of sanitary napkins and incontinence absorbent articles for females, the absorbent is positioned over the vagina area such that the absorbent structure will absorb body fluids. The wearer then checks to ensure that the first region 101 of the shell or the adhesive 144, if present, is contacting the skin around the vagina area.

If the absorbent article is intended to have a front and a back portion, the wearer first identifies the anterior region 164 and/or the posterior region 166 of the absorbent article. To aid in identification of the anterior and posterior regions, indicia located on the release sheet 146, shell 114 or absorbent structure 121 viewable through the opening 105 in the shell 114 to indicate the anterior region and/or posterior region of the absorbent article may be present. Indicia can be simply lettering or a picture to indicate the front or back of the absorbent article. Once the anterior region and posterior region are identified by the wearer, the wearer places the absorbent article in the same manner described above. Examples of indicia that may be used include, color, wording, diagrams and the like, that would indicate to a wearer the anterior and posterior regions of the absorbent article.

In each case, the absorbent structure, which is designed to cover the labia majora of the wearer, may be positioned with the aid of the absorbent structure 121 or the opening 105. More specifically, the absorbent structure and/or the opening, when sized and shaped to the approximate size of the labia majora, can serve to guide the placement of the absorbent structure 121 over the labia majora. Once properly placed, pressure is applied by the wearer to the second side 117 and or backsheet 123 of the shell that will allow the first surface of the shell to contact the skin of the wearer, or to allow any adhesive applied to the first surface to be applied to the skin of the wearer.

By having the absorbent article 100 attached to the body of a wearer, the absorbent article 100 will tend to move with the skin of the wearer. This results in a comfortable to wear absorbent article that will be less likely to leak than conventional absorbent articles. The absorbent article has a very close-to-the-body fit that may provide improved discretion for the wearer.

Other benefits of the absorbent article 100 may also be provided. For example, when the first side 115 of the shell has an adhesive applied thereto, upon removal of the absorbent article after use, the wearer may fold the first side of the shell onto itself to dispose of the used absorbent article. An effective seal may be formed around the perimeter of the shell, thereby effectively encapsulating the absorbent structure within a closure and the backing sheet of the absorbent layer. As a result, any odors associated with the absorbed fluids will be contained within the shell material and backing layer. Another use of the absorbent article 100 is a tampon backup absorbent article. The absorbent article can also be effective in hiding the withdraw string of a tampon, while providing additional leakage protection.

The absorbent article described above can be an individual absorbent article or may be part of an absorbent system, offering the wearer a wide variety of options to fulfill the needs of the wearer. For example, the shell can be provided to wearers in a variety of shapes or sizes to allow the wearers to select the appropriate shape and/or size for their given body shape. Likewise, the body adhesive may be provided in a variety of adhesive strengths to match the adhesive strength needed or desired by the wearer. By providing a variety of adhesive or other attachment means, a wearer could select the shells to match body type, body condition, and other various factors that may vary from one wearer to another. Similarly, the absorbent structure could be provided in various absorbent capacities so that the wearer could select the appropriate absorbency to match the wearer's needs.

The absorbent system may be provided to wearers in a variety of packaging arrangements. In one packaging arrangement, a plurality of shells having different properties may be provided in separate packages or could be provided in a single package. It is generally a better packaging arrangement if shells having similar properties, shapes or sizes are provided in a single package. That is, in a given package, the wearer is provided with a plurality of shells all having the same shape, size, and properties, such as the body attachment properties. Regarding the absorbent structures, the absorbent structures could be provided to the wearer in packages sorted by absorbent capacity or various absorbent capacity structures could be provided in a single package. By having all absorbent structures in a single package with a single absorbent capacity, a wearer is able to select the correct absorbent capacity for their typical needs. However, by providing different absorbent capacity absorbent structures in a single package, the wearer will be provided with the ability to select the absorbent structure with the appropriate absorbent capacity for a given situation, without the need to purchase multiple packages of absorbent articles.

Figure 13:
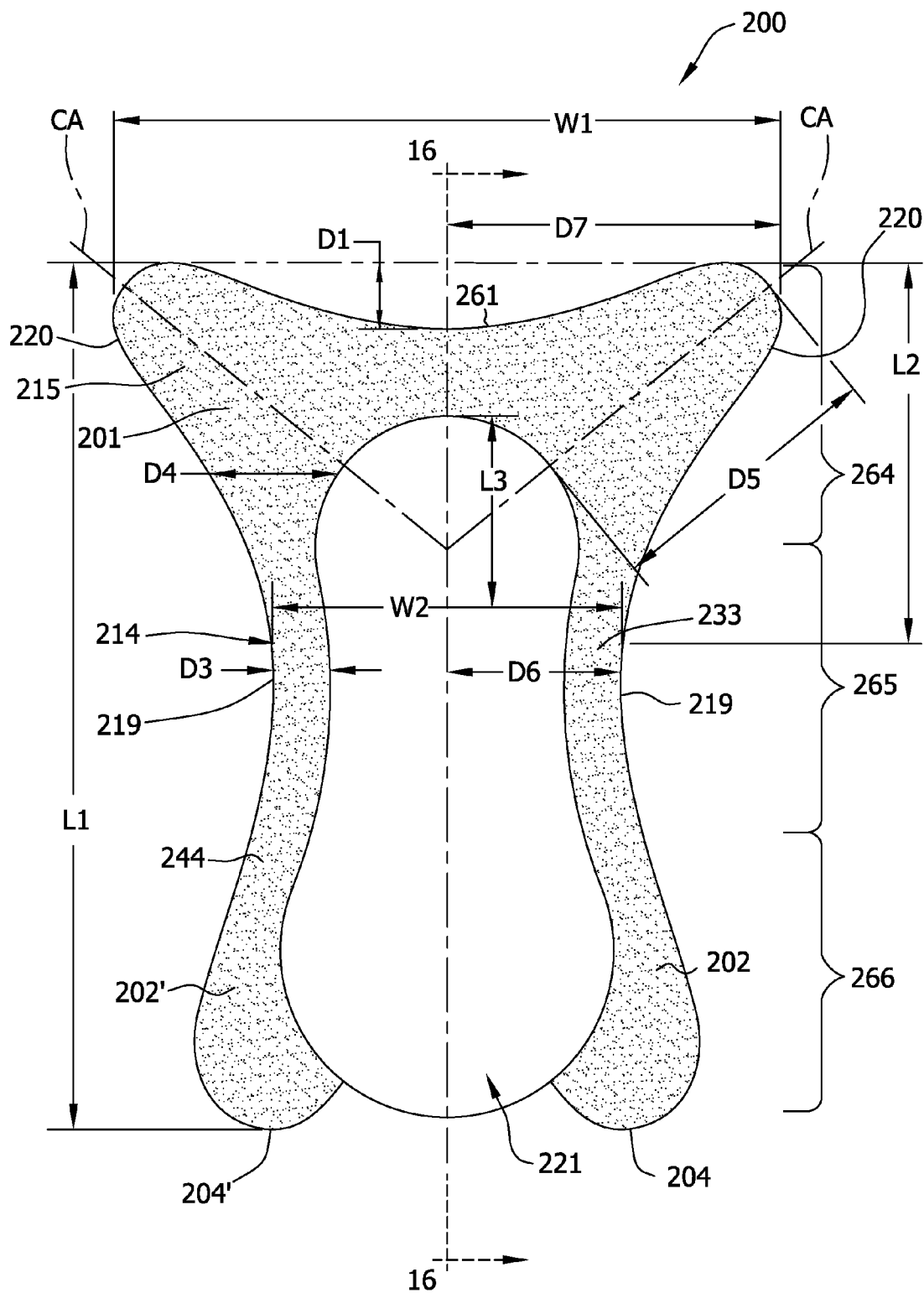
FIG. 13 shows a top view of the absorbent article.
Figure 14:
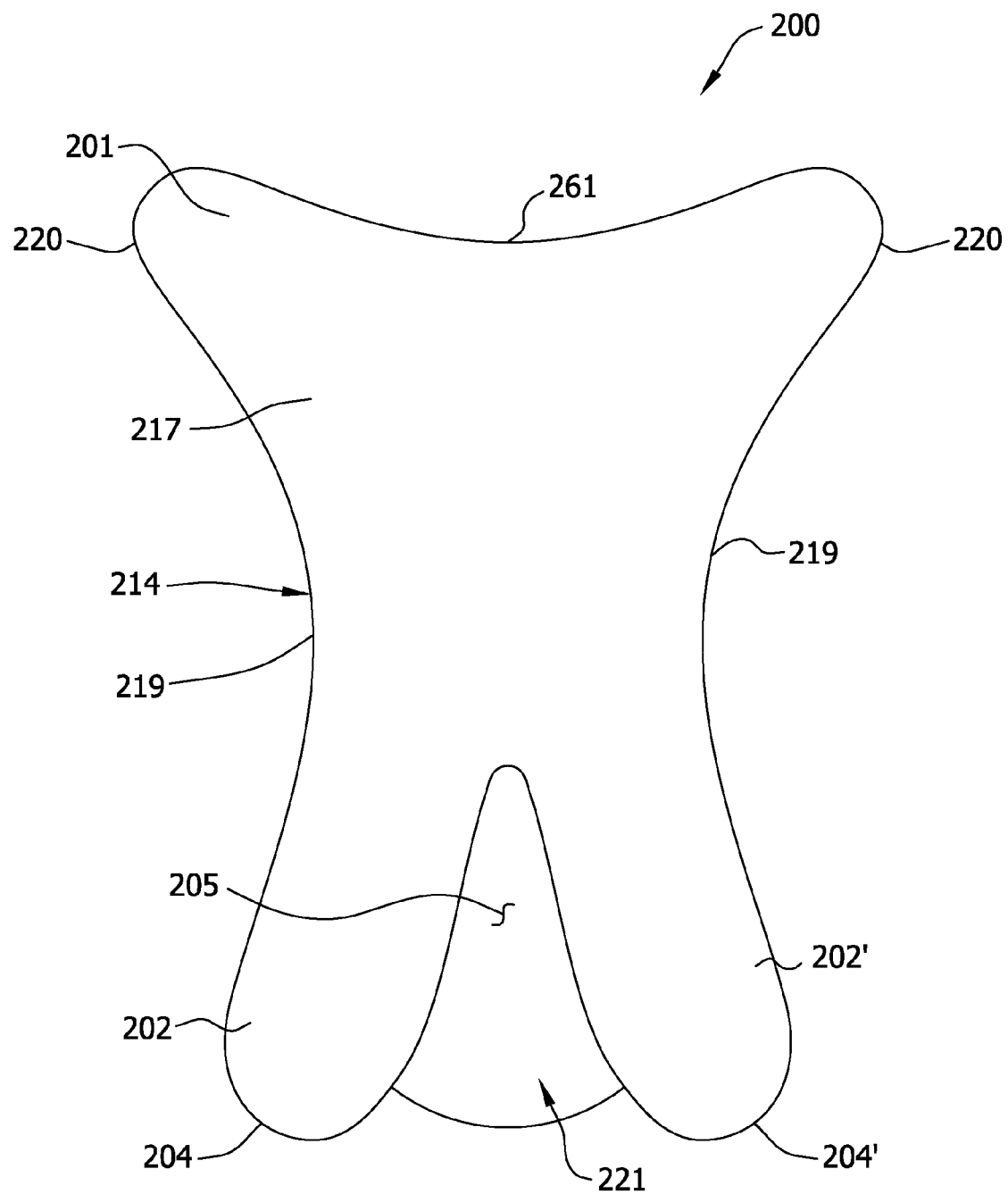
FIG. 14 shows a bottom view of the absorbent article.

In another embodiment, a body adhesive absorbent article 200, which is illustrated in FIGS. 11-18, also comprises a shell 214 and an absorbent structure 221 and has a longitudinal axis X and a transverse axis Y. The shell 214 has a first region 201, a pair of lateral side regions 202, 202' extending from the first region, and an opening 205 (FIG. 12) extending longitudinally at least in part between the side regions. The shell 214 also has a first side 215, which defines a body-facing surface (FIG. 11), and a second side 217, which defines a garment-facing surface (FIG. 14). In the illustrated embodiment, the first side 215 of the shell 214 has a body adhesive 244 on at least a portion thereof for adhering the absorbent article 200 directly to the wearer's skin, and particularly, to a female wearer's skin surrounding her vulva region for the illustrated absorbent article. The body adhesive 244 contacts the skin and hair, if present, in the vulva region and possibly the pubic region and/or the perinea region of the wearer's body, thereby supporting and holding the shell 214 and absorbent structure 221 against the body of the wearer during use. A peel sheet or release sheet (not shown) may be used to prevent the body adhesive 244 from becoming contaminated, thus losing its ability to stick to the body of the wearer and/or prematurely adhering to an unintended surface.

Generally, the size and shape of the absorbent structure 221, depending on its intended use, will dictate the size of the shell 214. The shape of the shell 214 is selected so that the absorbent article 200 will have a comfortable feeling for the wearer and inhibit the absorbent article against becoming detached from the body of the wearer during use thereby providing protection against leaks. In one suitable embodiment, the absorbent article 200, including the shell 214 and absorbent structure 221, is dimensioned and shaped to fit approximately 75 percent of adult females. It is understood, however, that the absorbent article 200 can be dimensioned and shaped to fit more or fewer females. It is also contemplated that different sizes of the absorbent article 200 may be provided to accommodate a greater percentage of females.

With reference to FIG. 13, the absorbent article 200 (and hence the shell 214) can be suitably divided into three general longitudinal regions: an anterior region 264, a posterior region 266 and a central region 265 extending longitudinally between and interconnecting the anterior and posterior regions. Each of these regions 264, 265, 266 is sized and shaped for alignment with different body regions of a wearer of the absorbent article. More specifically, the anterior region 264 of the article 200 is adapted to be disposed adjacent the wearer's lower abdomen region. The central region 265 is adapted to be disposed between the upper thigh region of the wearer to cover the wearer's perineum region and vaginal region. The posterior region 266 of the article 200 is adapted to be disposed in the gluteal region of the wearer.

In the illustrated embodiment, the anterior region 264, the central region 265, and the posterior region 266 of the absorbent article 200 are of roughly equal length, with each region corresponding generally to about ⅓ of a total length L1 of the absorbent article 200. The length L1 is defined herein as the longitudinal distance from a longitudinally outermost extent of the article 200 (and in the illustrated embodiment, the shell 214) in the anterior region 264 to a longitudinally outermost extent of the article (and in the illustrated embodiment, the shell) in the posterior region 266. As an example, the length L1 of the shell 214 (and hence the absorbent article 200 in the illustrated embodiment) may suitably be in the range of about 170 mm to about 220 mm, and more suitably in the range of about 190 mm to about 200 mm. As an additional example, the absorbent article 200, and more particularly the shell 214, has a length L1 of about 194 mm. It is understood that the absorbent article 200 may have a length L1 different that those set forth above without departing from some aspects of this invention. It is also contemplated that two or all three of the article regions 264, 265, 266 may instead be of unequal lengths depending on the desired fit and the intended body placement of the article without departing from the scope of this invention.

The absorbent structure 221 of FIGS. 11-18 is suitably adhered to the first side (i.e., body-facing surface) 215 of the shell 214 and is sized and located relative to the shell such that the shell extends both longitudinally and transversely outward beyond the periphery of the absorbent structure in at least the anterior region 264 and the central region 265, and more suitably in at least a portion of the posterior region 266 as well. The absorbent structure 221 is offset longitudinally, i.e., not centered lengthwise on the transverse or lateral axis of the absorbent article, such that the shell 214 extends longitudinally outward beyond the absorbent structure a greater distance in the anterior region 264 of the article 200 than in the posterior region. It is understood, though, that the absorbent structure 221 may be longitudinally centered so that the shell 214 extends equally longitudinally outward beyond the absorbent structure, or may be offset longitudinally toward the anterior region 264 so that the outward longitudinal extension of the shell beyond the absorbent structure is greater in the posterior region 265 than in the anterior region without departing from the scope of this invention.

As illustrated in FIG. 13, the anterior region 264 of the absorbent article 200 comprises the first region 201 of the shell 214 and includes a portion of the absorbent structure 221. Since much of the first side (i.e., body-facing surface) 215 of the shell 214 is exposed (i.e., not covered by the absorbent structure 221) in the anterior region 264 of the absorbent article 200, a relatively large surface area of the first side of the shell has body adhesive 244 applied thereto for adhering the shell, and hence the absorbent article, to the wearer.

A first end 261 of the absorbent article 200, and more particularly a longitudinal edge of the anterior region 264 defining this first end of the absorbent article 200, is suitably contoured along the width of the shell at this first end to accommodate the lower abdomen region of the wearer. In the illustrated embodiment, for example, the longitudinal extent (e.g., length) of the shell 214 relative to the transverse axis of the article is non-uniform across the width of the shell at the first end 261 of the article, and more suitably increases as the shell extends transversely outward from the longitudinal axis of the article to transversely, or laterally opposite sides 219 of the article and more particularly laterally opposite side edges of the shell. Accordingly, a greatest longitudinal extent of the shell 214 is generally adjacent the intersection of the longitudinal end 261 with the respective sides 219 of the article (i.e., the shell in the embodiment of FIG. 13). More suitably, the longitudinal edge of the shell 214 (i.e., at first end 261 of article 200 in the illustrated embodiment) is generally arcuate as it extends across the width of the shell at its longitudinal edge. It is understood, however, that the contour of the longitudinal edge of the shell 214 in the anterior region 264 of the article may be V-shaped, U-shaped or other suitable shape without departing from the scope of this invention.

The contoured longitudinal edge of the shell 214 (i.e., first end 261 of the article 200 in the illustrated embodiment) thus broadly defines a recess in the anterior region 264 of the article (and thus of the shell in this instance). This recess defines a longitudinal distance D1 between the longitudinally outermost extent of the longitudinal edge of the shell 214 in the anterior region 264 and the longitudinal extent of the longitudinal edge of the shell at the longitudinal axis of the article 200 in the anterior region. In one suitable embodiment, the distance D1 of the recess is in the range of about 5 mm to about 35 mm, and more suitably about 12 mm to about 18 mm. As one example, the distance D1 of the recess at the anterior region 264 in the embodiment of FIG. 13 is approximately 15 mm.

The sides 219 of the illustrated article 200 are suitably defined by transversely opposite side edges of the shell 214. These side edges of the shell 214 are contoured so that the overall width of the article 200 (i.e., the distance between the transversely opposite sides 219 thereof), and more particularly the width of the shell in the illustrated embodiment, is non-uniform along the length L1 of the article to define leg cutouts for accommodating the upper thighs of the wearer. In one suitable embodiment, the width of the article 200 and hence the shell 214 increases from a narrowest width W2 in the central region 265 of the article toward each of the longitudinally opposite ends (261 and 204, 204') of the article. Still more suitably, the width of the article 200 and more suitably the shell 214 is also greater in the anterior region 264 of the article than in the posterior region 266. In the illustrated embodiment, for example, a greatest width W1 of the article 200 is defined by the transverse side edges of the shell 214 adjacent the longitudinal edge of the shell (e.g., first end 261 of the article 200) in the anterior region 264 of the article. As additional examples, the greatest width W1 of the article 200 and more particularly the shell 214 is in the range of about 52 mm to about 180 mm and more suitably about 140 mm to about 170 mm. In the illustrated embodiment of FIG. 13, the greatest width W1 of the article 200 is approximately 150 mm. The narrowest width W2 of the article 200 and more particularly the shell 214 is in the range of about 45 mm to about 85 mm, and more suitably about 60 mm to about 80 mm. In the illustrated embodiment, for example, the narrowest width W2 of the shell 214 is approximately 78 mm. In other embodiments, a ratio of the length L1 of the shell 214 (and hence the article 200 in the illustrated embodiment) to the narrowest width W2 of the shell 214 (and hence article 200) is in the range of about 3 to about 1, and more suitably about 2 to about 1.

In the article 200 illustrated in FIG. 13, the sides 219 of the article 200 and more particularly the transverse side edges of the shell 214 are generally arcuate along substantially the entire length L1 of the article. Alternatively, the sides 219 may be arcuate along only a portion of the length L1 of the article. It is also understood that the sides 219 defining the leg cutouts may be V-shaped, U-shaped or other suitably shape, or it they may be uniform (e.g., straight or longitudinal) along substantially the entire length L1 of the article 200. It is also understood that the sides 219 of the article may be contoured to define article 200 widths other than those set forth above without departing from the scope of this invention. It is further understood that the greatest width of the article 200 may be other than in the anterior region 264, and/or the narrowest width may be other than in the central region 265 of the article and remain within the scope of this invention.

Still referring to FIG. 13, the contoured longitudinal edge of the shell 214 (e.g., first end 261 of the article 200) at the anterior region 264, together with the contoured transverse side edges of the shell (e.g., article sides 219) where these side edges generally intersect the longitudinal edge of the shell, define a pair of transversely spaced tabs 220 in the anterior region. Each tab 220 has a central axis CA extending in part transversely outward of the shell 214 and in part longitudinally outward of the shell. Each of the tabs 220 suitably has body adhesive 244 on the body-facing surface (e.g., first side 215) for adhering the tabs directly to the wearer and more suitably to the abdomen region of the wearer. In one particularly suitable embodiment, the tabs 220 are sized to extend to a region of the wearer that has little or no pubic hair to facilitate better adherence to the wearer's skin. For example, in one embodiment each of the tabs 220 extends outward along its central axis CA away from the peripheral edge of the absorbent structure 221*a* distance D5 in the range of about 20 mm to about 90 mm, and more suitably about 45 mm to about 70 mm. Each tab 220 also has a transversely outermost extent (which in the illustrated embodiment defines the greatest width W1 of the shell 214 and hence the article 200) defining a distance D6 from the longitudinal axis of the article to the transversely outermost extent of a respective one of the tabs (which is approximately half of the width W1 of the shell). In a particularly suitable embodiment, a ratio of the distance D6 (that the tab 220 extends transversely outward) to the distance D5 (the length of the tab along its central axis CA) is in the range of about 1 to about 2. In another suitable embodiment, a ratio of the distance D6 to a distance between the longitudinal axis of the shell 214 and a side edge of the absorbent structure 221 (i.e., about half of the width W5 shown in FIG. 18) is in the range of about 2 to about 5.

Each of the tabs 220 further has a longitudinally outermost extent (which in the illustrated embodiment defines the outermost extent of the longitudinal edge of the shell 214) in the anterior region 264 defining a length L2 from the transverse axis of the shell 214 to the longitudinally outermost extent of the tab 220. This length L2 is suitably in the range of about 50 mm to about 120 mm, and more suitably about 70 mm to about 100 mm. As illustrated in FIG. 3, the absorbent structure 221 extends longitudinally into the anterior region 264 of the article and has a longitudinally outermost extent defining a length L3 from the transverse axis to the longitudinally outermost extent of the absorbent structure in the anterior region. For example, this length L3 may suitably be in the range of about 30 mm to about 90 mm, and more suitably about 50 mm to about 70 mm. In another embodiment, a ratio of the length L2 (the longitudinally outermost extent of the tabs 220) to the length L3 (the longitudinally outermost extent of the absorbent structure 221 in the anterior region 264) is in the range of about 3 to about 1 and more suitably about 2 to about 1.

Figure 17:
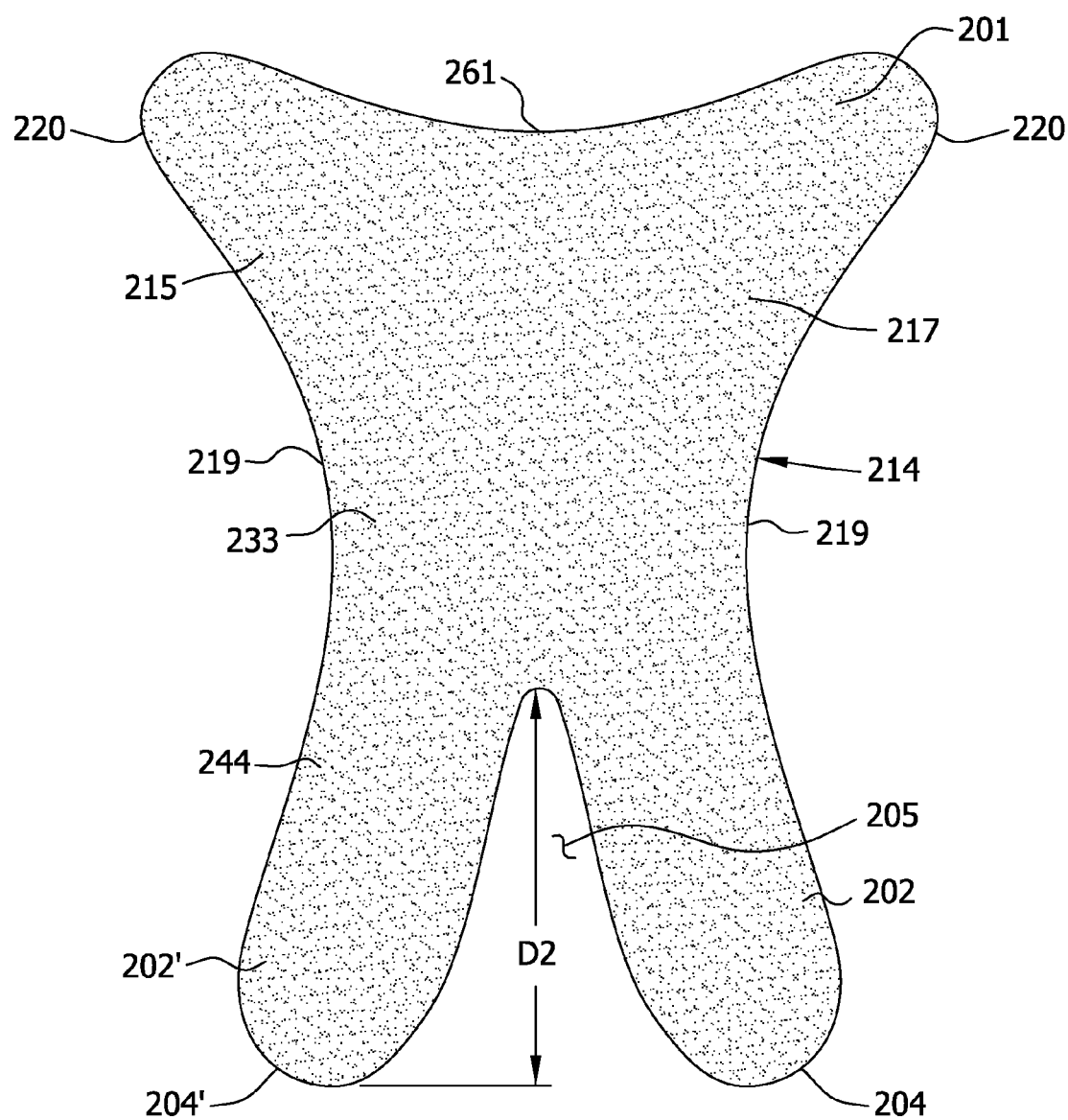
FIG. 17 shows a top view of a shell of the absorbent article.

With reference now to FIG. 17, the posterior region 266 of the absorbent article 200 includes the opening 205 in the shell 214 with portions of the lateral side regions 202, 202' broadly defining a pair of transversely spaced tabs disposed on opposite sides of the opening. The posterior region 266 disposition of these tabs is such that the tabs are aligned generally with the buttocks of the wearer rearward of the perineal region. In the illustrated embodiment, the opening 205 is in the form of a generally V-shaped ingress extending longitudinally on the longitudinal axis of the article 200 such that the tabs are free to flex relative to the central region 265 of the article and generally independent of each other to accommodate normal movement of the wearer's thighs and buttocks. In one particularly suitable embodiment, the ingress 205 extends longitudinally inward from the distal end 204, 204' of the absorbent article 200 (and more particularly a greatest longitudinal extent of the shell in the posterior region 266) a distance D2 in the range of about 5 mm to about 100 mm, and more suitably about 50 mm to about 80 mm. In the illustrated embodiment, for example, the ingress 205 has a distance D2 of about 75 mm. In another embodiment, the distance D2 of the ingress 205 is in the range of about 5 percent to about 60 percent of the length L1 of the shell 214, and more suitably about 25 percent to about 40 percent of the length L1. In other embodiments, a ratio of the distance D1 of the recess in the anterior region 264 of the shell 214 to the distance D2 of the ingress 205 in the posterior region 266 is in the range of about 4 to about 1, and more suitably between about 3 and about 1. In still another embodiment, a ratio of the distance D1 of the recess in the anterior region 264 of the shell 214 to the total length L1 of the shell is suitably in the range of about 0.03 to about 0.2 and more suitably in the range of about 0.06 to about 0.09. It is understood, however, that the ingress 205 can be larger or smaller without departing from some aspects of this invention.

Figure 15:
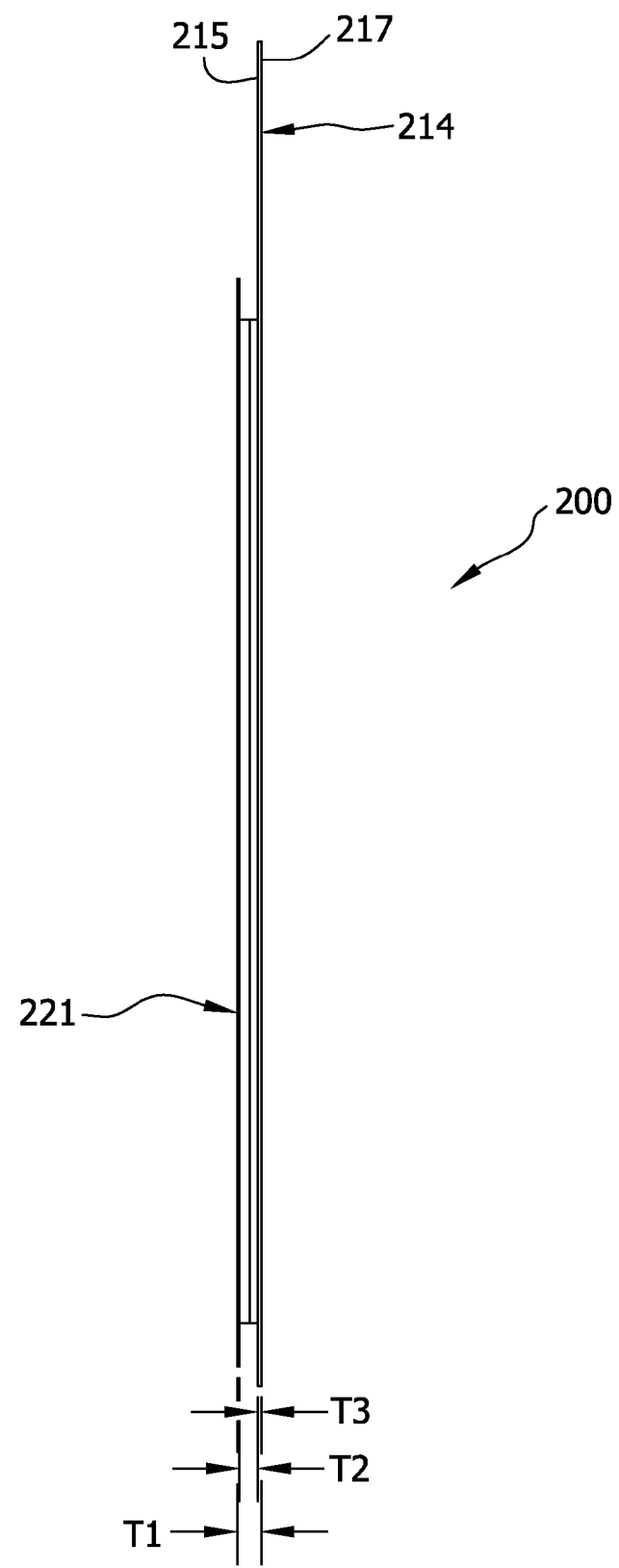
FIG. 15 shows a side view of the absorbent article.
Figure 16:
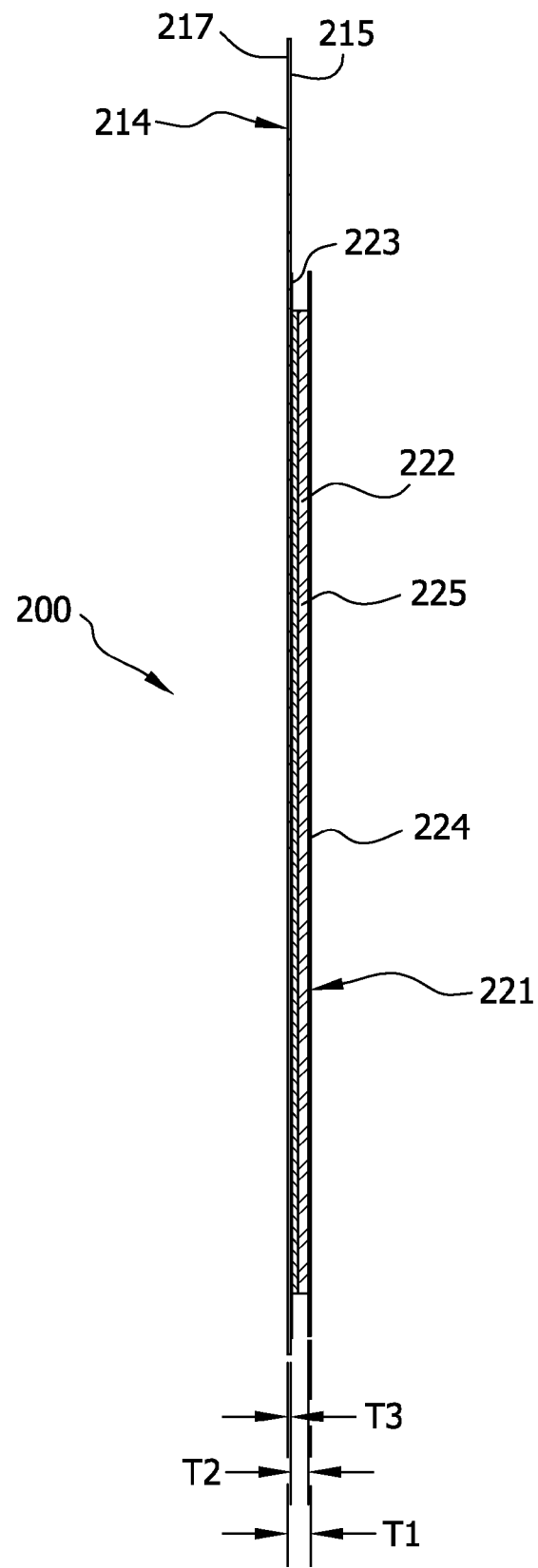
FIG. 16 shows a side cut-away view of the absorbent article taken along line 16-16 of FIG. 13.

Turning now to FIGS. 15 and 16, the absorbent structure 221 may comprise a single layer structure or be constructed of multiple layers. The illustrated absorbent structure 221, for example, comprises an absorbent core 222, an intake layer 225, a top sheet 224, and a liquid impermeable backsheet 223. A total thickness T1 of the absorbent article 200 is suitably in the range of about 1 mm to about 12 mm, and more suitably about 2.5 mm to about 5 mm. As one example, the thickness T1 of the illustrated absorbent article is approximately 3.5 mm. It understood, however, that the thickness T1 may be other than as set forth above depending at least in part on the intended use of the absorbent article 200. For example, an absorbent article 200 in which the absorbent structure 221 is intended to be used in the manner a maxi-pad may have a greater thickness T1 than an absorbent article in which the absorbent structure is to be used in the manner of a pantyliner. In another suitable embodiment, the absorbent structure 221 has a thickness T2 in the range of about 1 mm to about 12 mm, and more suitably in the range of about 1.5 mm to about 5 mm. In the illustrated embodiment, for example, the thickness T2 of the absorbent structure is approximately 3 mm. The shell 214 itself may have a thickness T3 between about 0.03 mm and about 5.0 mm, and more suitably about 0.1 mm to about 3.0 mm. In one particularly suitable embodiment, the thickness T3 of the shell 214 is between 0.25 mm and about 3.0 mm. In the illustrated embodiment, for example, the shell 214 has a thickness T3 of about 0.5 mm.

Figure 18:
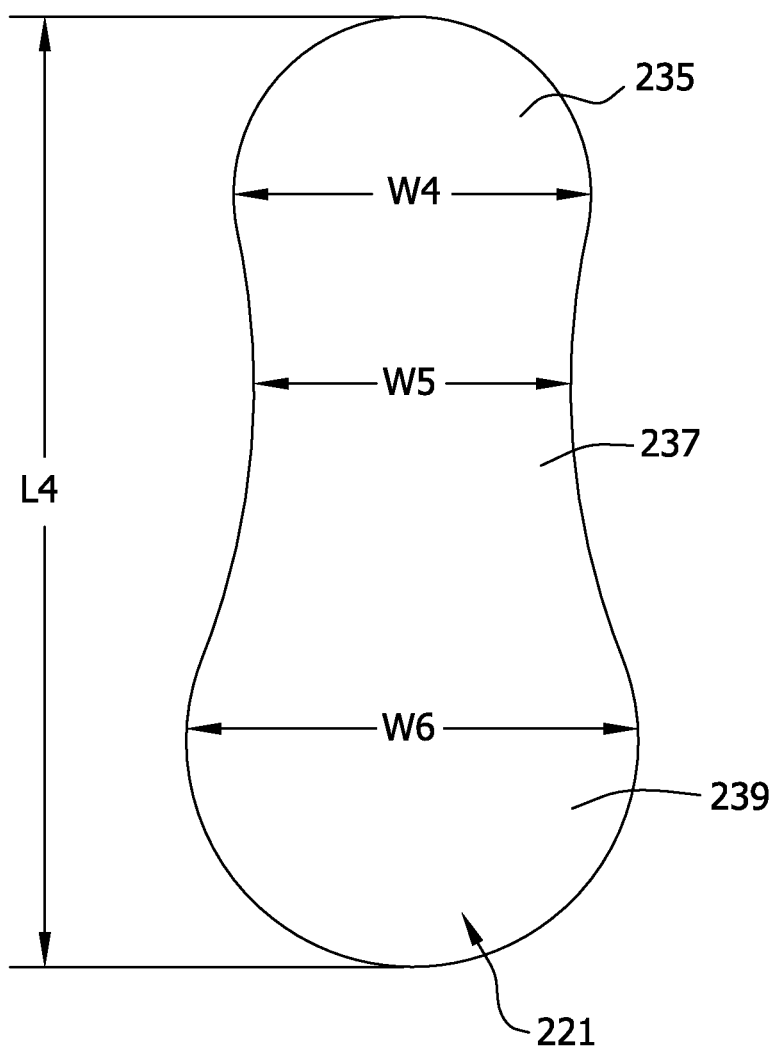
FIG. 18 shows a top view of an absorbent structure of the absorbent article.

With reference now to FIG. 18, the illustrated absorbent structure 221 has an upper portion 235, a middle portion 237, and a lower portion 239. The absorbent structure is generally hourglass shaped, with the upper portion 235 suitably having a width W4 between about 10 mm and about 80 mm, and more suitably about 30 mm to about 60 mm. In the illustrated embodiment, for example, the width W4 of the upper portion 235 is approximately 47 mm. The middle portion 237, which is the narrowest portion of the absorbent structure 221, may have a width W5 between about 10 mm and about 80 mm, and more suitably about 30 mm to about 60 mm. In the illustrated embodiment, the width W5 of the middle portion 237 is approximately 40 mm. The lower portion 239 has a width W6 between about 10 mm and about 120 mm, and more suitably about 40 mm to about 80 mm. In the illustrated embodiment, for example, the width W6 of the lower portion 239 is approximately 63 mm. In another suitable embodiment, the absorbent structure 221 has a longitudinal length L4 in the range of about 80 mm and about 180 mm, and more suitably about 110 mm to about 150 mm. As one example, the longitudinal length L4 of the illustrated absorbent structure 221 is about 145 mm. It is understood, however, that the absorbent structure may sized in width and/or length other than as set forth above without departing from the scope of this invention. It is also understood that the absorbent structure 221 may be any suitable shape other than a generally hourglass shape within the scope of this invention.

With reference back to FIG. 13, the absorbent structure 221 is secured to the first side (i.e., body-facing surface) 215 of the shell 214, such that at least a portion of the absorbent structure covers the opening or ingress 205 in the shell. The absorbent structure 221 may be attached to the shell 214 in a permanent manner, meaning that the absorbent structure is generally intended not to be removable by the wearer of the absorbent article 200. Alternatively, it may be removably and in some embodiments refastenably) attached to the shell 214, such that the absorbent structure 221 may be removed (and in some embodiments reattached) by a wearer.

The shell 214 and absorbent structure 221 are sized relative to each other such that a portion of the shell extends outward beyond the peripheral edge of the absorbent structure along at least a portion of the peripheral edge of the absorbent structure. In this manner, a portion of the shell 214 about the periphery of the absorbent structure 221 is uncovered with the first side (i.e., body-facing surface) 215 of the shell exposed and available for adhesion to the wearer. For example, the shell 214 in one suitable embodiment extends outward beyond the peripheral edge of the absorbent structure 200 at least in the anterior region 264 and central region 265, and more suitably also in a portion of the posterior region 266. In accordance with one embodiment, for example, the shell 214 extends outward of the peripheral edge of the absorbent structure 221a distance D3 in the range of at least about 3 mm, more suitably in the range of about 5 mm to about 15 mm and even more suitably about 8 mm to about 13 mm. In one embodiment, the entire first side 215 of the uncovered portion of the shell 214 has body adhesive 244 thereon for adhering the shell and thereby the absorbent article to the wearer.

As illustrated in FIG. 13, the distance that the shell 214 extends outward beyond the peripheral edge of the absorbent structure 221 is suitably non-uniform about the periphery of the absorbent structure. More particularly, the shell 214 extends transversely outward beyond each of the side edges of the absorbent structure 221 a greater distance in the anterior region 264 than in the central region 265. It is understood, however, that shell 214 may extend a uniform distance outward of the absorbent structure 221, or may extend outward according to a different pattern than illustrated in FIG. 13, and remain within the scope of this invention. In another suitable embodiment, the first side (i.e., body-facing surface) 215 of the shell 214 has a total surface area in the range of about 50,000 mm$^2$ to about 20,000 mm$^2$, and more suitably about 30,000 mm$^2$ to about 40,000 mm$^2$. The absorbent structure 221 has a total body-facing surface area of about 4,500 mm$^2$ to 45,000 mm$^2$ and more suitably about 15,000 mm$^2$ to about 20,000 mm$^2$. Thus, between about 10,000 mm$^2$ and about 45,000 mm$^2$, and more suitably about 18,000 mm$^2$ to about 22,000 mm$^2$ of surface area of the first side 215 of the shell 214 remains uncovered by the absorbent structure 221. Stated another way, about 40 percent to about 95 percent, and more suitably about 40 percent to about 65 percent of the shell 214 is uncovered by the absorbent structure 221.

As one example, in the illustrated embodiment the shell 214 has a total surface area of about 34,000 mm$^2$ of which about 20,000 mm$^2$ is uncovered and available to have body adhesive 244 applied thereto. The illustrated absorbent structure 221 has a total body-facing surface area of about 18,000 mm$^2$ of which about 14,500 mm$^2$ covers or overlies the shell 214. Accordingly, about 60 percent of the illustrated shell 214 has body adhesive 244 and can be used to adhere the absorbent article 200 to the wearer's skin. It is understood, however, that less than the entire exposed area of the shell 214 can have body adhesive 244 thereon. It is also understood that body adhesive can be applied to the absorbent structure 221 to adhere or partially adhere the absorbent structure to the wearer's skin.

Additional embodiments of a body-adhesive absorbent article 10 are illustrated in FIGS. 19A through 29B. As in the previous embodiments, one component of the absorbent article 10 is a shell 14 having a first side 15 and a second side 17. The shell 14 serves to provide the overall contour or silhouette of the absorbent article of the present invention. In addition, the shell 14 also provides a surface for attachment or adhesion of the absorbent article 10 to the body of a user.

Figure 19A:
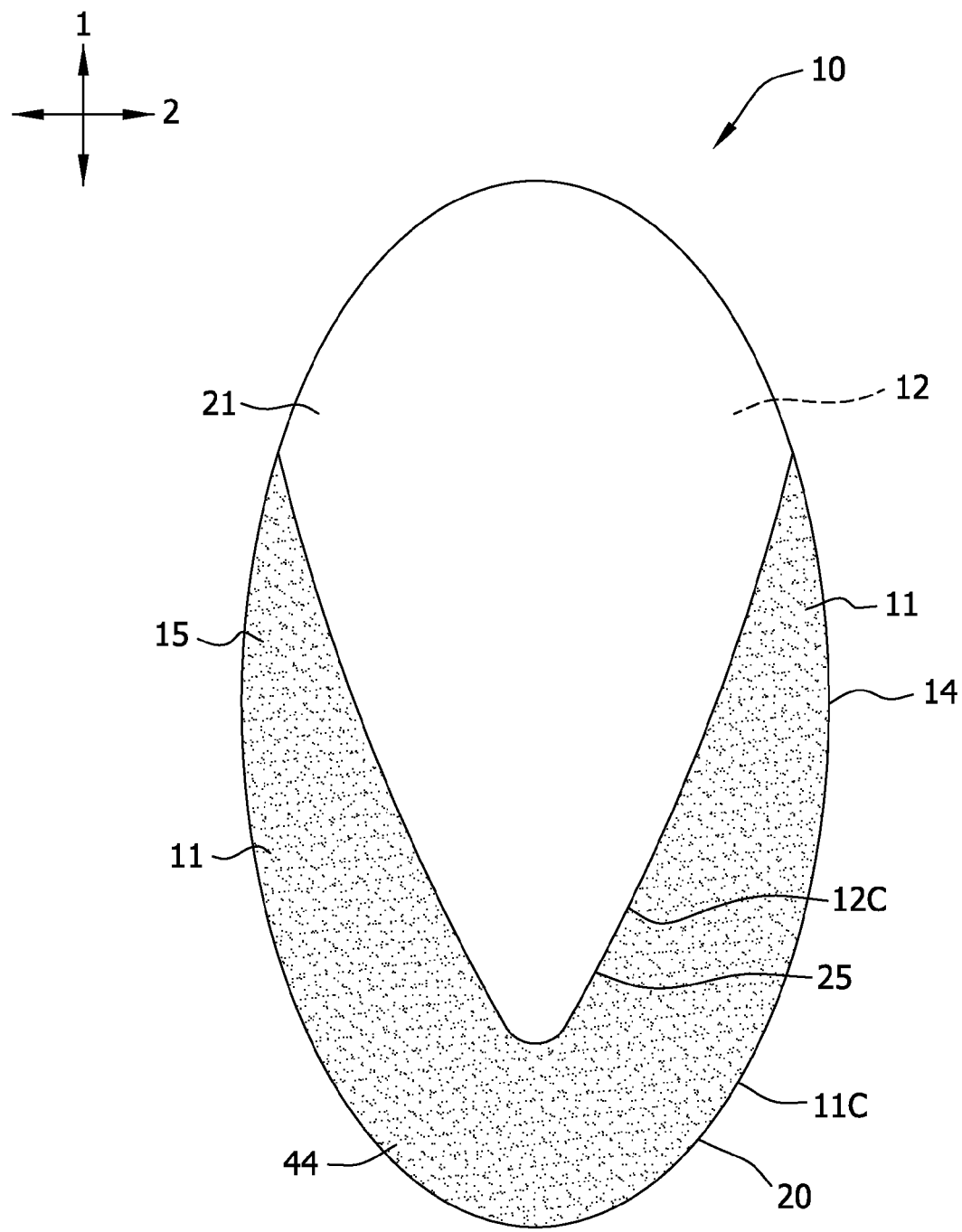
FIGS. 19A and 19B each show a top view of other embodiments of an absorbent article of the present invention.
Figure 19B:
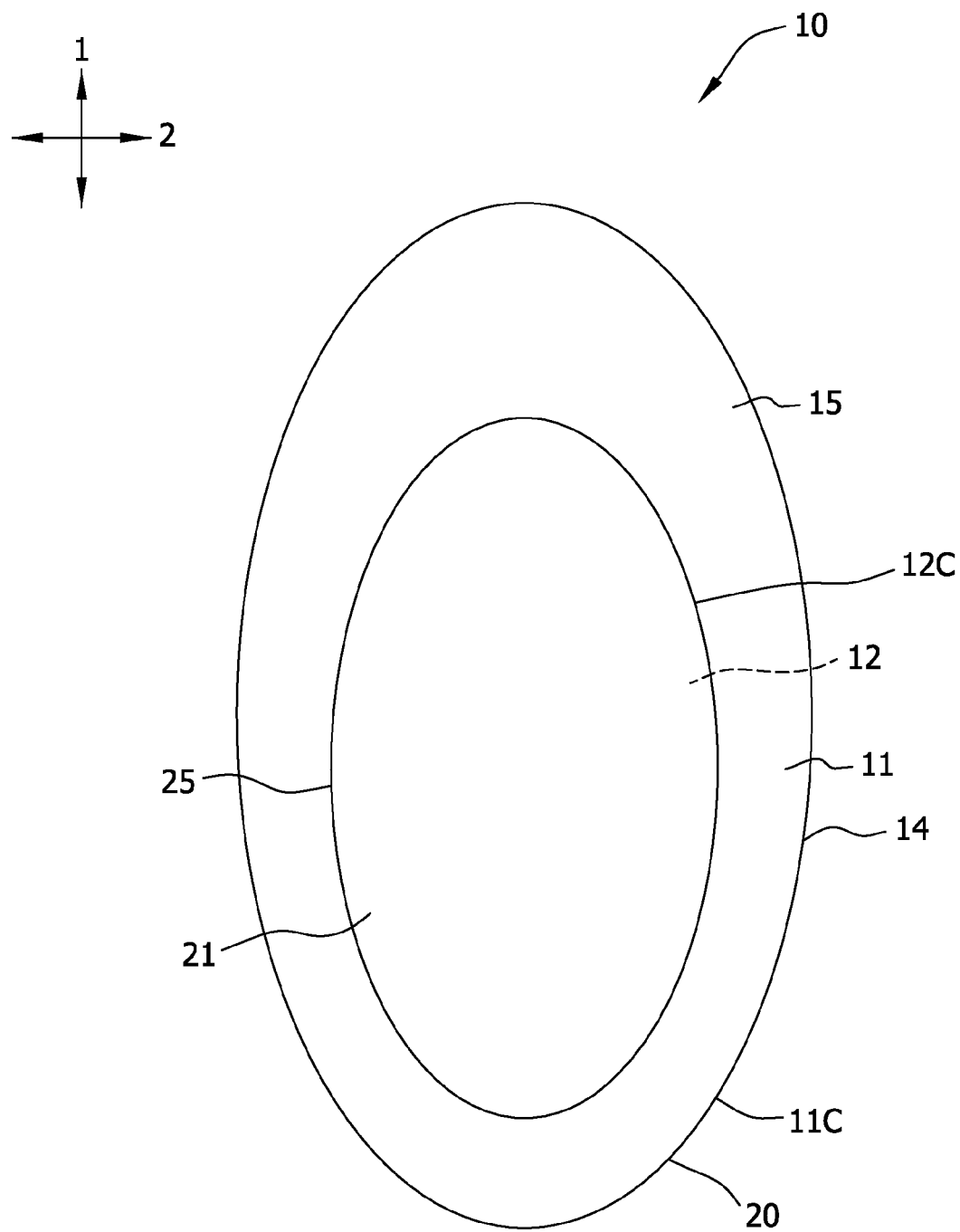

The first side 15 of the shell 14 is the body facing side of the absorbent article 10 and the second side 17 of the shell 14 is the garment facing side of the absorbent article. The first side 15 of the shell 14 has a first area 11 and a second area 12. The first area 11 surrounds or bounds the majority of the second area 12, as is clearly shown in FIG. 19A. By "surrounds or bounds the majority", it is meant that at least 51% of a circumference 12C of the second area 12 contacts the first area 11. Generally, at least 60% of the circumference 12C of the second area 12 contacts the first area 11. In a particular embodiment, at least 75% of the circumference 12C of the second area 12 is in contact with the first area 11. In another particular embodiment, at least 90% of the circumference 12C of the second area 12 is in contact with the first area 11. In a further embodiment, at least 95% of the circumference 12C of the second area 12 is in contact with the first area 11. In still a further embodiment, the first area 11 completely surrounds the second area 12 of the shell 14 as seen in FIG. 19B.

In one embodiment, the first area 11 of the first side of the shell 14 is designed or adapted to contact, attach, or adhere to the wearer's skin. In one particular embodiment, the first area 11 of the shell 14 is designed or adapted to contact a female wearer's skin surrounding the vulva region of the female torso when the absorbent article 10 is applied to the wearer. Generally, the shell 14 is sized and shaped such that the extent of the first area of the shell only contacts and attaches or adheres to the skin surrounding and proximate to the vulva area and possibly the pubic and perinea regions of the wearer. In addition to contacting the skin in the vulva, pubic and perinea regions of the wearer, the first area 11 of the first area of the shell 14 may also contact and attach or adhere to any hair in the vulva area of the user which may be present. The first area 11 is the portion of the first side 15 of the shell 14 which holds the absorbent article in place on the user.

Generally, the second area 12 of the shell 14 is the portion of the shell 14 which provides absorbency to the absorbent product. That is, the second area 12 of the first side to the shell is any area of the first side of the shell which has an absorbent structure attached thereto, or has absorbent properties. In one particular embodiment, the second area 12 of the shell 14 has an absorbent structure 21 contained therein or attached thereto. It is noted that the second area 12 may be a single contiguous area or may be two or more distinct areas. Generally, the second area 12 is a single contiguous area from an ease of manufacturing standpoint. In an alternative embodiment, the second area 12 of the shell may contain an absorbent material integrated into the shell 14, such that the second area 12 of the shell is absorbent without the presence of an additional absorbent structure. The second area 12 shell may have an absorbent material coated or impregnated into the shell material.

The shell 14 of the absorbent article 10 may be prepared from a variety of materials. The shell may include a layer constructed of any material which will function to be operatively liquid impermeable. The shell 14 may, for example, include a polymeric film, a woven fabric, a nonwoven fabric or the like, as well as combinations or composites thereof. For example, the shell 14 may include a polymer film laminated to a woven or nonwoven fabric. A laminate shell 14 structure is shown in FIG. 20A, having an upper layer 141 and a lower layer 142, wherein the upper layer is the body-facing side of the shell 14 and the lower layer 142 is the garment facing side of the shell 14. In a particular feature, the polymer film can be composed of polyethylene, polypropylene, polyester, silicone or the like, as well as combinations thereof. Additionally, the polymer film may be micro-embossed, have a printed design, have a printed message to the consumer, and/or may be at least partially colored. Suitably, the shell 14 can operatively permit a sufficient passage of air and moisture vapor out of the absorbent article 10, particularly out of an absorbent structure 21 while blocking the passage of bodily fluids and odors often associated with bodily fluids. An example of a suitable shell material can include a breathable, microporous film, such as those described in, for example, U.S. Pat. No. 6,045,900 to Haffner et al., the entire disclosure of which is incorporated herein by reference and made a part hereof. Other shell materials that are extensible may be used in the present invention. Examples of extensible backsheet materials are described in U.S. Pat. No. 5,611,790, issued Mar. 18, 1997, to Osborn, III et al., herein incorporated by reference in its entirety.

In one embodiment, the shell 14 may be a laminate of a woven or nonwoven fabric with a silicone polymer, wherein the silicone polymer has adhesive properties. The second side 17 of the shell will be woven or nonwoven fabric and the first side 15 of the shell will be silicone polymer. One commercially available laminate is an Oleeva Fabric® 1 available from Bio Med Sciences, Inc., which have offices at 7584 Morris Court, Suite 218 Allentown, Pa. 18106. The Oleeva Fabric® is a silicone sheeting having adhesive properties laminated to a fabric backing. The silicone sheeting will form the body facing first side 15 of the shell material. Relating this particular structure to the Figures, in FIG. 20A, the silicone polymer is the upper layer 141 of the shell 14 and the nonwoven or woven layer is the lower layer 142 of the shell.

Bicomponent films or other multi-component films can also be used as the shell 14 material. In addition, woven and/or nonwoven fabrics that have been treated to render them operatively liquid-impermeable can also be used as an effective shell 14 material. Another suitable shell material can include a closed-cell polyolefin foam, a polyurethane polymer material, a silicone polymer, or other similar materials. Silicone polymers having naturally occurring adhesive properties, or silicone polymers having a silicone adhesive layer applied thereto are of particular interest for the shell material. Such silicone polymers will allow the first area 11 of the shell 14 to adhere to the body of the user without the need of an additional adhesive. These materials may be laminated to another material such that the second side 17 of the shell 14, which is the garment facing side of the absorbent article 10, so that the adhesive nature of the silicone polymer does not adhere the garment of under garments of the user. In another embodiment, the shell material may be prepared from an interpenetrating polymer network or two or more polymers. Generally, one of the polymer of the interpenetrating polymer network may be a silicone material. Examples of interpenetrating polymer networks are described in U.S. Pat. No. 5,759,560, issued to Dillion, which is hereby incorporated by reference in its entirety.

The shell material should be selected such that the overall properties of the shell allow the shell material to move the skin of the user during normal use and normal movements by the user during use. The shell 14 should not be too rigid, such that the shell detaches from the skin of the user during use and the shell should not be so flexible that the shell tends to twist and bunch during use. The shell 14 should have sufficient flexibility to conform to the skin of the user and become similar to a second skin of the user.

Generally, the shell material should have sufficient thickness to allow the shell 14 to mold to the body of the user, but not too thick that the shell 14 becomes uncomfortable for the user to wear. In addition, the shell 14 should not be so thin that it ineffectively forms a seal with the skin of the user when applied to the user, or becomes detached from the skin of the user during use and normal movement of the user during use or that it does not adequately conform to the shape and skin of the user at the point of attachment to the user. Depending on the material used for the shell, the typical thickness of the shell is between 0.03 mm and about 5.0 mm, more particularly between 0.1 mm and 3.0 mm. In one particular embodiment, the thickness of the shell is between 0.25 mm and about 3.0 mm. Again, the actual thickness used is dependent of several factors including rigidity of the material, the flexibility of the material, and the ability of the material to assume the shape of the skin of the user at the location of use, which is typically the vulva region of a user.

The second side 17 of the shell 14 forms the garment-facing side of the absorbent article when worn by a user. The shell 14 material should be selected such that the second side of the shell will freely move against the undergarment or clothing of a user. One way to achieve this result is to have the second side 17 of the shell 14 to have a fairly low coefficient of friction. This will allow the second side 17 of the shell 14 to freely move against the undergarment or other clothing worn by the user. If the second side 17 of the shell 14 does not freely move against the undergarment or other clothing worn by the user, the absorbent article may catch on the undergarment or clothing, which may result in the absorbent article being prematurely and undesirably removed from the user or may cause the absorbent article to be shifted from its desired placement against the body of a user.

In order to achieve the desired coefficient of friction on the second side 17 of the shell 14, the materials used to prepare the shell could be selected such that the second side 17 of the shell material will inherently have the desired coefficient of friction. Alternatively, the second side 17 of the shell 14 may be treated with a coating composition, such a polytetrafluoroethylene containing coating, a silicone containing coating, or other similar coating having low coefficient of friction properties. Alternatively, the shell 14 could be made from a laminate of two or more materials such that the first side 15 of the shell 14 is prepared from a material that meets the needed properties of the first side 15, while the material selected for the second side 17 of the shell 14 meets the desired coefficient of friction such that the second side 17 will free move against the undergarment or garment being worn by a user.

The shell 14 of the absorbent article 10 may be flat or may have a three-dimensional shape. As seen in FIG. 21, which is a side perspective view of the absorbent article, the shell 14 has a three-dimensional concave shape. Alternatively, as seen in cross-sectional side views of FIGS. 20, 20A and 22, the shell 14 may have a generally flat shape. By providing the absorbent article 10 with a three-dimensional concave shape as seen in FIG. 21, placement of the article may be easier for the user. Generally, the three-dimensional shape could be such that it closely matches the overall general curvature of the vulva region and optionally the pubic and perinea regions of most women, when the absorbent article is used as a pantiliner, sanitary napkin, or a feminine incontinence article. To form the shell 14 with a three-dimensional shape, the shell may be molded in any manner known to those skilled in the art, for example heat molding. The manner in which the three-dimensional shape is imparted to the shell 14 is not critical to the present invention.

Figure 23:
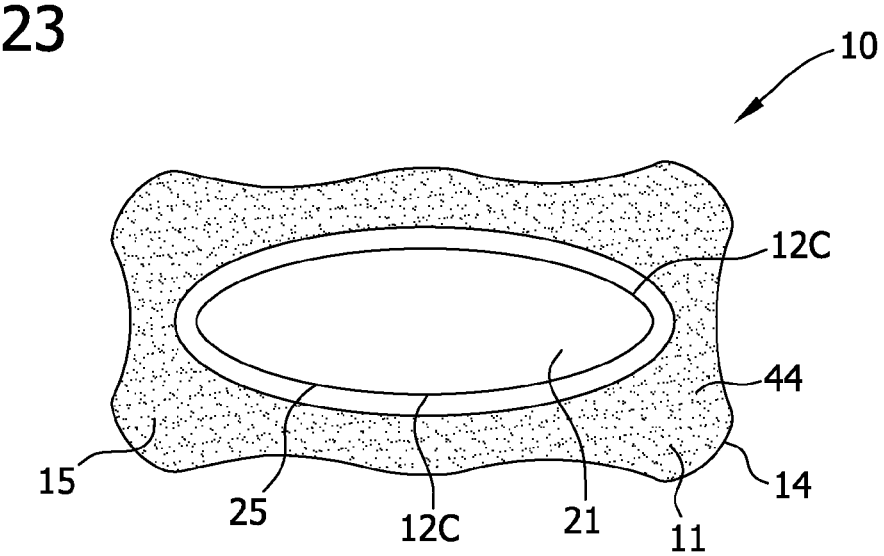
FIGS. 23, 23A, and 23B each show a top view of an embodiment of an absorbent article of the present invention having a different shell shape.
Figure 23A:
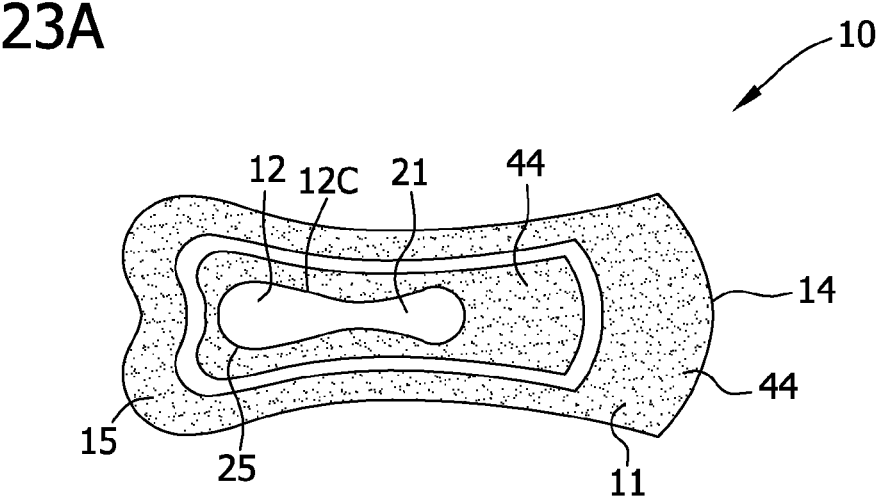
Figure 23B:
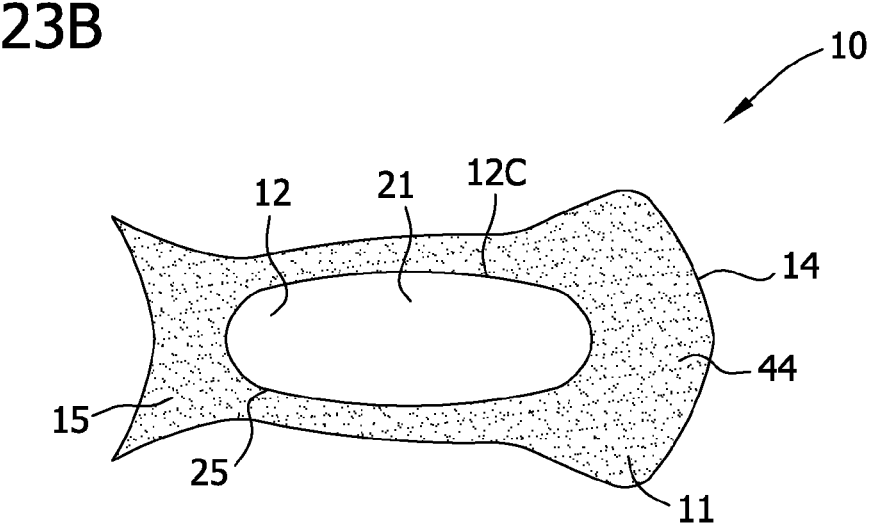

When the shell 14 is a flat shape, meaning that the shell does not have a third dimension other than thickness, the shell 14 should be made to be flexible enough that the shell 14 can conform to the body of the user at the point of attachment. In addition to being flat, the overall shape of the shell 14 may be contoured, as seen in FIGS. 23, 23A and 23B. In one embodiment, the contour shape may be such that the narrowest point of the contour is in the crotch area of the shell 14 nearest the vulva region, as seen in FIG. 23A. The contour shape shown in FIG. 23 is one of many possible shapes the shell 14 and absorbent article may be prepared. Other shapes may be used, without departing from the scope of the present invention. Generally, the shape selected should be such that the shell 14 and absorbent article 10 are comfortable for the user to wear, while providing leakage protection to the user. It is noted that a contour shape may also be used in conjunction with a three-dimensional shell. Further discussion of the overall shape of the absorbent article may be found below.

The shell may be any desired color or may be translucent. In addition, the shell may have a matt finish, satin finish, or a smooth finish. The particular finish color or translucency can be a matter of choice for the manufacturer of the absorbent article of the present invention. However, by providing a shell which is translucent may assist the user in placing the absorbent article 10 prior to use, since the user may be able to see where the article is placed compared to the genitalia of the user.

The illustrated absorbent structure 21 is designed to absorb body exudates, including menstrual fluid, blood, urine, and other bodily fluids, such as sweat and vaginal discharges. The absorbent structure 21 has a longitudinal direction 1 and a lateral direction 2. This absorbent structure 21 may be a single layer or may be multiple layers. Typically, the absorbent structure 21 has an absorbent core 22. This absorbent core 22 may contain one or more layers of absorbent materials. That is, the absorbent core 22 may be a single layer of absorbent materials or may be a multilayer structure. Each of the layers can contain similar materials or different materials. In the illustrated absorbent article 10, the materials that can be used to form the absorbent core 22 include those materials conventionally used in absorbent articles, such as, cellulose, wood pulp fluff, rayon, cotton, and meltblown polymers such as polyester, polypropylene, or coform. Coform is a meltblown air-formed combination of meltblown polymers, such as polypropylene, and absorbent staple fibers, such as cellulose. A desired material is wood pulp fluff, for it is low in cost, relatively easy to form, and has good absorbency.

The absorbent core 22 can also be formed from a composite comprised of a hydrophilic material that may be formed from various natural or synthetic fibers, wood pulp fibers, regenerated cellulose or cotton fibers, or a blend of pulp and other fibers. One particular example of a material that may be used as the absorbent core is an airlaid material. The absorbent core 22 may have other properties including extensibility, which will allow the absorbent core to be extended or fit to a particular user. One example of extensible absorbent cores is described in U.S. Pat. No. 5,611,790, issued Mar. 18, 1997, to Osborn, III et al., herein incorporated by reference in its entirety.

In one embodiment, the absorbent core 22 may also include a superabsorbent material, in addition to or in place of the hydrophilic material, which increases the ability of the absorbent core to absorb a large amount of fluid in relation to its own weight. Generally stated, the superabsorbent material can be a water-swellable, water-insoluble, hydrogel-forming polymeric absorbent material that is capable of absorbing at least about 15 times, suitably about 30 times, and possibly about 60 times or more its weight in physiological saline (e.g. saline with 0.9 wt % NaCl). The superabsorbent materials can be inserted as particles or in sheet form. The superabsorbent material may be biodegradable or bipolar. The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers may be lightly crosslinked to render the material substantially water insoluble. Crosslinking may, for example, be by irradiation or covalent, ionic, Van der Waals, or hydrogen bonding. Hydroxyfunctional polymers have been found to be good superabsorbents for sanitary napkins. Such superabsorbents are commercially available from Dow Chemical, Hoechst-Celanese, and Stockhausen, Incorporated, among others, and are a partially neutralized salt of cross-linked copolymer of polyacrylic acid and polyvinyl alcohol having an absorbency under load value above 25 grams of absorbed liquid per gram of absorbent material (g/g). Other types of superabsorbent materials known to those skilled in the art can also be used.

Figure 20:
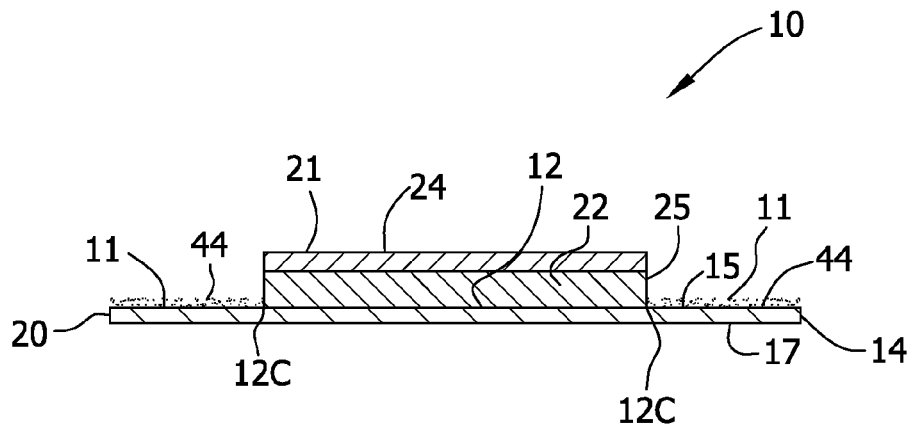
FIGS. 20 and 20A show side cross-sectional views of still other embodiments of absorbent articles of the present invention.
Figure 20A:
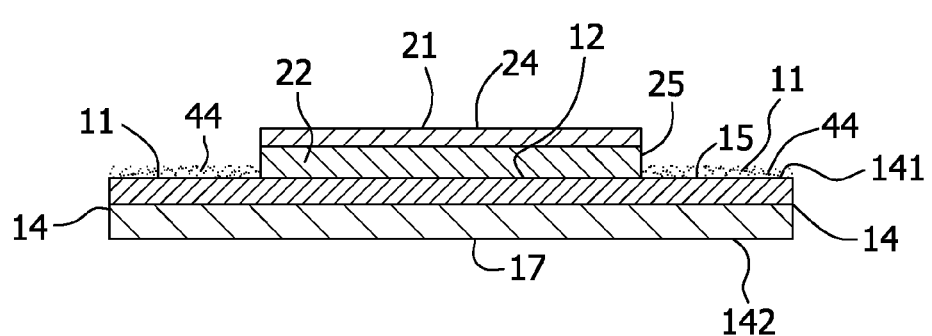
Figure 21:
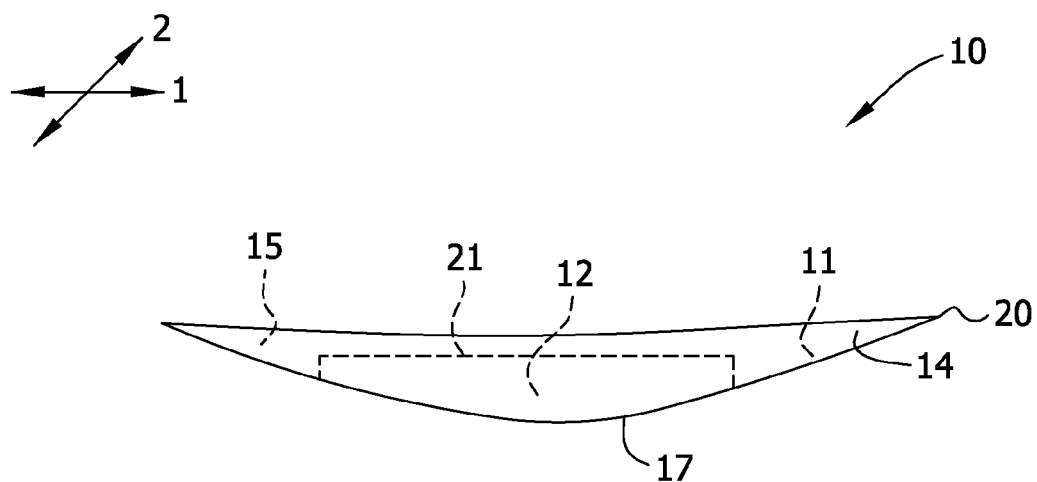
FIG. 21 shows a side view of another embodiment of an absorbent article of the present invention wherein the shell has a concave shape.
Figure 22:
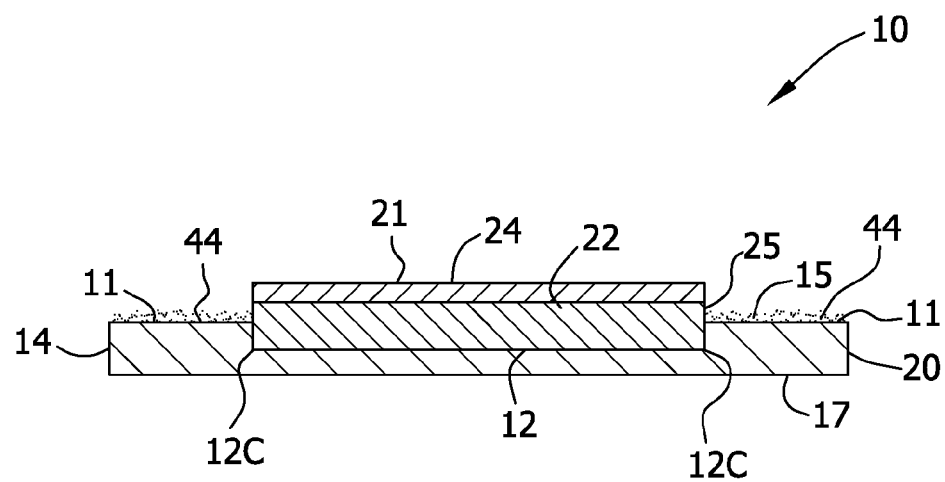
FIG. 22 shows a cross-sectional side view of an absorbent article of the present invention with the absorbent core recessed into the shell.

Generally, the absorbent core 22 will be positioned adjacent the shell 14, as seen in FIGS. 20, 20A and 22. In addition, the absorbent core 22 may be recessed into the shell 14 as seen in FIG. 22.

In addition to the absorbent core 22, the absorbent structure 21 may have other additional layers that aid the absorbent core 22 in capturing and holding the bodily fluid into the absorbent core 22. These other layers, when present and in combination with the absorbent core 22, form the absorbent structure 21 of the absorbent article 10. There may be a single layer or multiple layers in addition to the absorbent core in the absorbent structure 21. Alternatively, the absorbent structure 21 may have a single layer, which is generally the absorbent core 22.

One particular example of an additional layer that may be used in addition to the absorbent core 22 is a body-side liner or top sheet 24, which is generally a liquid permeable material, which allows bodily fluids to pass through the top-sheet into the absorbent core. It is noted that the terms "body-side liner" and "top sheet" may be used interchangeable. The body side liner 24 also may provide a user with a dry feeling by separating the absorbent core 22 from the body of the user. That is, the body-side liner 24 can be placed between the absorbent core 22 and the body of the user such that the absorbent core 22 is located between the body side liner 24 and the shell 14.

Generally, the body side liner 24 will only extend to the edge 25 of the absorbent core, as seen in FIG. 20. However, the body side liner 24 may extend beyond the edge 25 of the absorbent core 22 and may be attached to the first side of the shell. Generally, if the body side liner 24 extends beyond the absorbent core 22, the body side liner will be attached to the first side 15 of the shell 14. Also, if the body side liner 24 extends beyond the absorbent core 22, the body side liner 24 will generally not cover the entire first area 11 of the first side 15 of the shell 14.

Optionally, the body side liner 24 may be formed from one or more materials. The body-side liner or top sheet 24 should be able to manage different body excretions depending on the type of product. In feminine care products, often the body-side liner or top sheet 24 must be able to handle menses and urine. The body-side liner or top sheet 24 may include a layer constructed of any operative material, and may be a composite material. For example, the body-side liner or body-contacting layer can include a woven fabric, a nonwoven fabric, a polymer film, a film-nonwoven fabric laminate or the like, as well as combinations thereof. Examples of a nonwoven fabric useable in the body-side liner or top sheet 24 include, for example, an airlaid nonwoven web, a spunbond nonwoven web, a meltblown nonwoven web, a bonded-carded web, a hydroentangled nonwoven web, a spunlace web or the like, as well as combinations thereof. Other examples of suitable materials for constructing the body-side liner or top sheet 24 can include rayon, bonded-carded webs of polyester, polypropylene, polyethylene, nylon, or other heat-bondable fibers, finely perforated film webs, net-like materials, and the like, as well as combinations thereof. These webs can be prepared from polymeric materials such as, for example, polyolefins, such as polypropylene and polyethylene and copolymers thereof, polyesters in general including aliphatic esters such as polylactic acid, nylon or any other heat-bondable materials. When the body-side liner is a film or a film laminate, the film should be apertured or otherwise be made to allow fluids to flow through the body-side liner to the absorbent core.

Other examples of suitable materials for the body-side liner or top sheet 24 are composite materials of a polymer and a nonwoven fabric material. The composite materials are typically in the form of integral sheets generally formed by the extrusion of a polymer onto a nonwoven web, such as a spunbond material. In a particular arrangement, the body-side liner or top sheet layer 24 can be configured to be operatively liquid-permeable with regard to the liquids that the article is intended to absorb or otherwise handle. The operative liquid-permeability may, for example, be provided by a plurality of pores, perforations, apertures or other openings, as well as combinations thereof, that are present or formed in the liner or body contacting layer. The apertures or other openings can help increase the rate at which bodily liquids can move through the thickness of the liner or body contacting layer and penetrate into the other components of the article (e.g. into the absorbent core 22). The selected arrangement of liquid permeability is desirably present at least on an operative portion of the body-side liner or top sheet 24 that is appointed for placement on the body-side of the article. The body-side liner or top sheet 24 can provide comfort and conformability, and can function to direct bodily exudates away from the body and toward the absorbent core 22. The body-side liner or top sheet 24 can be configured to retain little or no liquid in its structure, and can be configured to provide a relatively comfortable and non-irritating surface next to the body tissues of a wearer. In the present invention, the top sheet or body-facing surface of each absorbent article may be embossed, printed, or otherwise imparted with a pattern.

Additional layers or substrates, such as, a liquid acquisition and distribution layer, also referred to as a surge or transfer layer, and an optional tissue layer can be incorporated into the absorbent structure 21 of the absorbent article 10 between the body-side liner or top sheet 24 and the absorbent core. The distribution layer may be shorter than the absorbent core or have the same length as the absorbent core 22. The distribution layer serves to temporarily hold an insulting fluid to allow the absorbent core sufficient time to absorb the fluid, especially when a superabsorbent material is present.

In another embodiment, the absorbent core, transfer layer, and other components, such as tissue layers, may be free floating (unattached) between the shell 14 and the top sheet 24, and only are secured along only the peripheral edges thereof. Alternatively, the absorbent core 22, transfer layer, if present, and any other layer or component, if present, may be attached to one or both of the shell 14 and top sheet 24 and/or to each other.

The absorbent structure 21, including the absorbent core, is generally attached to the first side 15 of the shell 14 in the second area 12 of the shell. The attachment may be in a permanent manner, meaning that the absorbent structure is generally intended not to be removable by the user of the absorbent article 10. Alternatively, the absorbent structure 21 may be made to be removable by the user, meaning that the absorbent structure 21 may be removed and replaced with another absorbent structure 21 by the user of the absorbent article 10. When the absorbent structure 21 is attached to the shell 14 in a permanent manner, meaning that the absorbent structure is not intended to be removed by the user, a construction adhesive may be used. The construction adhesive may include any adhesive that will effectively hold the absorbent structure 21 in place, so as not to be separated from the shell 14. Commercially available construction adhesives usable in the present invention include, for example include Rextac adhesives available from Huntsman Polymers of Houston, Tex., as well as adhesives available from Bostik Findley, Inc, of Wauwatosa, Wis. Other means may be used to hold the absorbent structure 21 to the shell including other bonding means, including heat bonding, and ultrasonic bonding.

When the absorbent structure 21 is removably attached, the absorbent structure 21 is held in place on the shell 14 by a means that will allow the user to remove the absorbent structure. One such means of holding the absorbent structure is by using a pressure sensitive adhesive. Suitable pressure sensitive adhesives include any commercially available pressure sensitive adhesive. Examples of suitable pressure sensitive adhesives usable to removably hold the absorbent structure 21 in place on the shell 14 include pressure sensitive adhesives available from National Starch and, having offices in, Bridgewater, N.J. 08807. By providing an absorbent structure that is removable, the shell may be reused several times. That is, the shell 14 does not need to be replaced when the absorbent structure 21 is replaced. By having a removable absorbent structure, the absorbent structure can be selected by the user prior to use. This would allow the user to select an appropriate level of protection for a given day or allow the user to select a size or shape of the absorbent that the user finds to be more comfortable.

As is stated above, the absorbent structure 21 is located in the second area 12 of the shell 14 and on the first side 15 of the shell member. This size and shape of the absorbent structure may be varied depending of the intended use of the absorbent article and will be discussed in more detail below.

The absorbent structure 21 may have a relatively flat structure, as shown in FIGS. 20, 20A, 21 and 22. Alternatively, the absorbent structure may have a three-dimensional shape other that a relatively flat shape. The absorbent structure may have an anatomically correct shape such that the absorbent structure fits within the labia of the user. Anatomically correct shapes of absorbent are generally know to those skilled in the art and are generally found in the interlabial art field. The absorbent structure may be designed to be partially or fully interlabial. Alternatively, a three-dimensional shaped absorbent structure may also be used in the absorbent article 10 which is designed not to fit within the labia majora of the user. That is, the absorbent structure 21 is positioned completely outside the labia during use. The size, location and shape of the absorbent structure 21 may also be selected for an intended use. For example, in an overnight use, the absorbent may be located further back on the user towards the perinea region of the user. In an overnight use, the absorbent structure may be larger than in a product intended for daytime use. In a daytime use, the absorbent structure will generally be centrally located of the vulva region.

In another embodiment, the absorbent structure 21 is contained within the shell material. That is, the absorbent structure 21 is an integral part of the shell 14 and a separate absorbent structure is not present. One way to achieve an integral absorbent structure is to have a shell that is prepared from a material which is a laminate of two or more materials. The first side 15 of the shell 14 contains an absorbent material within the body facing side of the laminate. For example, superabsorbent particles or materials may be incorporated into the material making up the body facing layer of the laminate. Another way is to place a very light coating onto the first side 12 of the shell material, wherein the coating contains a superabsorbent particles or materials. Of course other absorbent materials, other than superabsorbent materials may be used in place of or in addition to the superabsorbent materials.

Figure 24A:
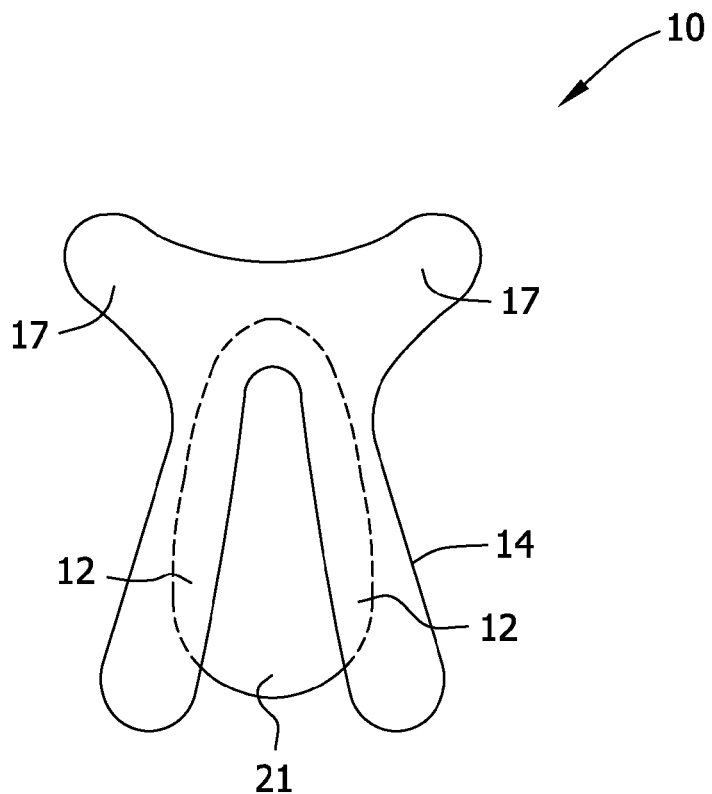
FIG. 24A shows a bottom view of an embodiment of an absorbent article of the present invention where only a portion of the absorbent structure is positioned over shell.
Figure 24B:
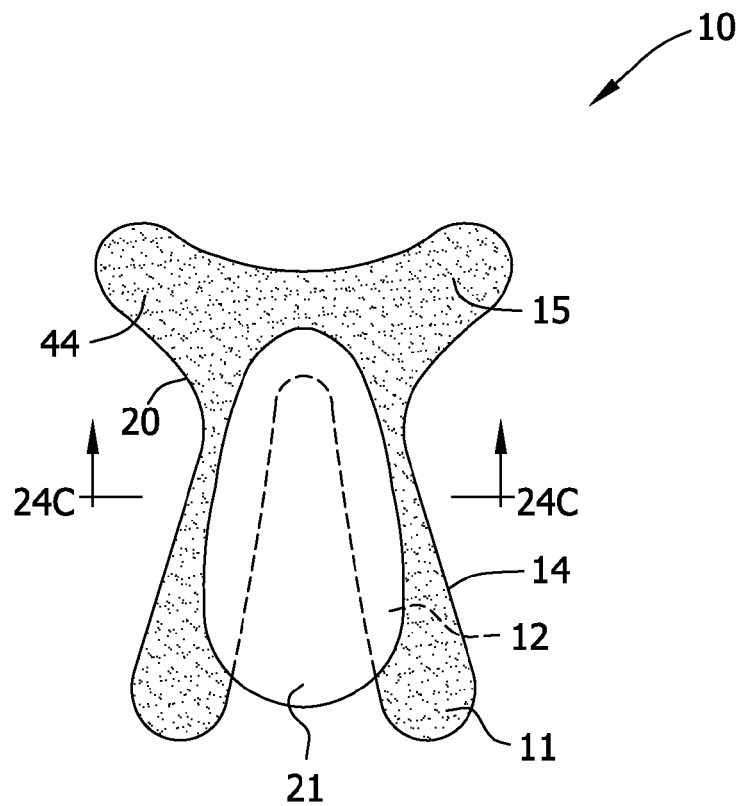
FIG. 24B shows a top view of an embodiment of an absorbent article of the present invention where only a portion of the absorbent structure is positioned over shell.
Figure 24C:
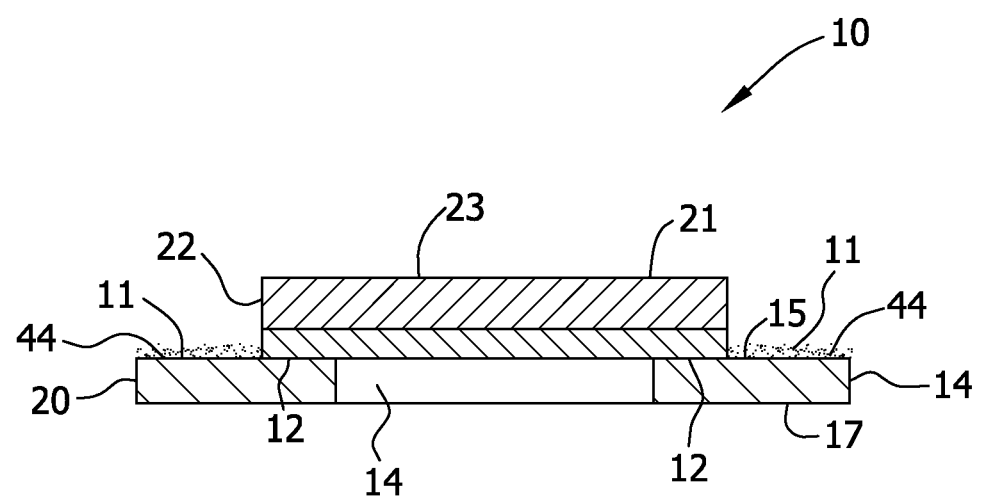
FIG. 24C shows a cross-sectional view taken along sectional line 24C-24C of FIG. 24B.

The absorbent structure 21 may be located entirely over the shell 14, as seen in FIGS. 19A, 19B, 20, 20A, 21, 22, and 23, meaning at the shell 14 material is located beneath the absorbent structure 14. Alternatively, the absorbent structure 21 may be positioned over the shell 14, such that only a portion of the absorbent structure 21 is over the shell 14. This configuration is shown in FIGS. 24A, 24B and 24C. FIG. 24A is a bottom view and FIG. 24B is a top view of the absorbent article 10. As can be seen, only a portion of the absorbent structure 21 is positioned over the shell 14. FIG. 24C shows a cross-sectional view of the absorbent article 10 taken along line 6C-6C in FIG. 24B. The portion of the first side 15 of the shell 14 in which the absorbent structure is attached is the second area 12 of the shell 14. Surrounding the second area 12 is the first area 11 of the shell 14. The second side 17 of the shell 14 is the side of the absorbent article that faces the user during use. By having an absorbent article with the structure shown in FIG. 24C, it is also beneficial for the absorbent structure to have an additional layer 23. This additional layer will serve to provide liquid impermeability to the absorbent structure, such that any fluids entering the absorbent core will not flow through the core to clothing of a user.

This additional layer 23 may be prepared from a variety of materials and is generally, this additional layer constructed of any material which will function to be operatively liquid impermeable. The additional layer, may be a polymeric film, a woven fabric, a nonwoven fabric or the like, as well as combinations or composites thereof. For example, the shell 14 may include a polymer film laminated to a woven or nonwoven fabric. In a particular feature, the polymer film can be composed of polyethylene, polypropylene, polyester, silicone or the like, as well as combinations thereof. Additionally, the polymer film may be micro-embossed, have a printed design, have a printed message to the consumer, and/or may be at least partially colored. Suitably, the additional layer can operatively permit a sufficient passage of air and moisture vapor out of the absorbent article 10, particularly out of an absorbent structure 21 while blocking the passage of bodily fluids and odors often associated with bodily fluids. Examples of suitable materials for the additional layer 23 include a breathable, microporous film, such as those described in, for example, U.S. Pat. No. 6,045,900 to Haffner et al., the entire disclosure of which is incorporated herein by reference and made a part hereof.

As is stated above, the first area 11 of the shell 14 serves either directly or indirectly attaches to the body of a user. Stated another way, the shell is the body attachment member and the first area 11 is the portion of the shell 14 which is attached to the body of the user. Depending on the material selected for the shell, the shell may actively attach to the body of the user using electrostatic means, suction means, or a body adhesive may be placed on the first area 11 of the shell 14 to attach the absorbent article to the body of a user. Electrostatic means that can be used is by selecting the shell material to be a material which has an affinity for the body of a user, such that the shell material "clings" to the body of the user. Examples of such materials include ethylene vinyl acetate, low density polyethylene and other similar materials know to those skilled in the art. Suction means may be achieved by shaping the shell to conform to the body of the user, much like a contact lens fits to the eye. Generally, suction means can be achieved by forming the shell 14 into a three-dimensional shape. The easiest way, however, to achieve body attachment is to place a body adhesive in the first area 11 of the shell 14.

The body adhesive 44 is positioned on the first area 11 of the first side 15 of the shell 14. The body adhesive 44 contacts the skin and hair, if present, in the vulva region and possibly the pubic region and/or the perinea region of the wearer's body, thereby supporting and holding the absorbent article 10 against the body of the wearer during use. The body adhesive 44 can overlie a portion of the first area 11 or can overlie the entire first area 11 of the shell 14. Generally, the body adhesive 44 will be present on a least the outer portion or near the circumference 11C of the first area near the edge 20 of the absorbent article. As seen in FIGS. 19A, 19B, 20, 20A, 22, 23B and 24B and 24C, the adhesive may cover the entire first area 11 of the absorbent article. Alternatively, the body adhesive 44 may be placed on a portion of the first area 11, as seen in FIGS. 23 and 23A. The body adhesive 44 may also be placed in a pattern of the first area 11. The body adhesive 44 can be applied to the first area 11 of the shell 14 of using any known process including, inkjet printing, screen printing, or extruding the body adhesive 44 from one or more nozzles, slot coating, and the like.

Generally, any pressure sensitive adhesive known to those skilled in the art may be used, provided that the pressure sensitive adhesive is not a known irritant to human skin or that the adhesive is so aggressive that it causes pain to the user when the absorbent article is removed from the skin. It is also desirable that the adhesive is selected such that the adhesive does not leave a substantial amount of residue on the skin of the user when the absorbent article 10 is removed. Particularly suitable pressure sensitive adhesive materials are disclosed in the commonly assigned U.S. Pat. No. 6,213,993 to Zacharias et al., U.S. Pat. No. 6,620,143 to Zacharias et al., the entire disclosure of each is incorporated herein by reference and made a part hereof. Other suitable adhesives are disclosed in U.S. Pat. No. 5,618,281 to Batrabet et al., the entire disclosure of which is incorporated herein by reference and made a part hereof. Other known body adhesives, such as those described in U.S. Pat. No. 6,316,524 to Corzani et al. which is hereby incorporated in its entirety, may also be used. Other examples of pressure sensitive adhesives include, Hydrogels, Hydrocolloids, Acrylics based adhesives, rubber based adhesives, such as Kraton based adhesives.

Figure 25:
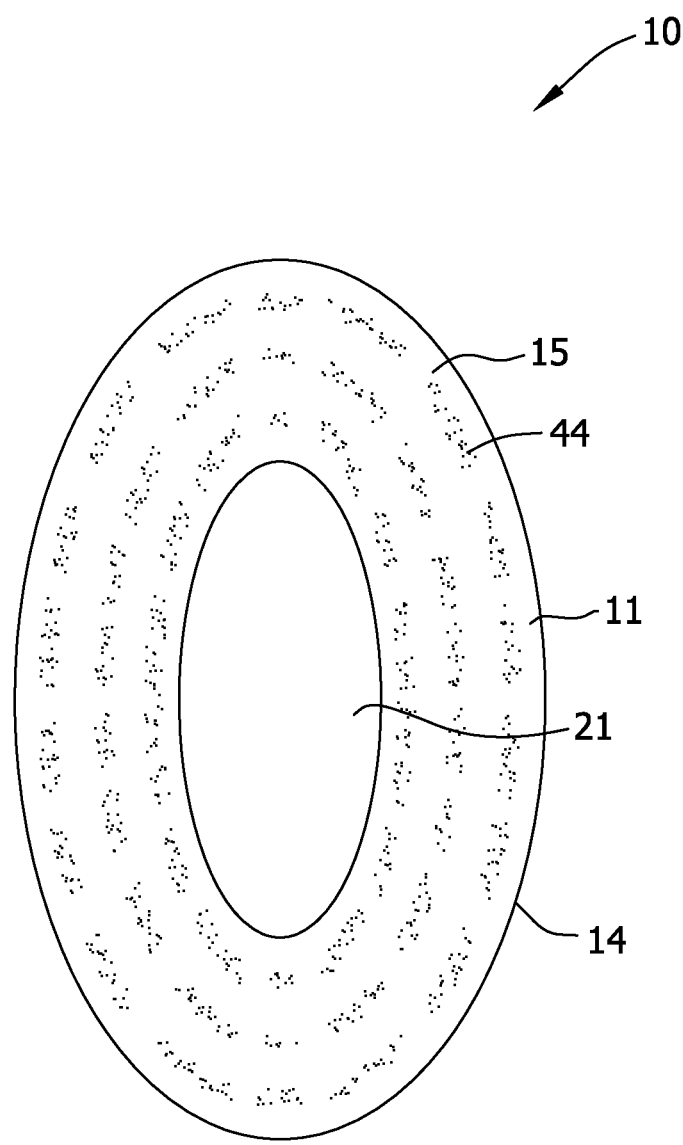
FIG. 25 shows a top view of an embodiment of an absorbent article of the present invention wherein the body adhesive is applied in an open pattern.

The body adhesive 44 may be positioned on the first area 11 of the shell 14 in an open pattern or a closed pattern. By "open pattern" is meant that the adhesive can have an intermittent or discontinuous pattern that does not substantially encircle the entire first area 11. For example, there are breaks in the body adhesive at certain portions of the first area 11. An open pattern of adhesive is shown in FIG. 23. "Closed pattern" means the adhesive 44 would encircle the entire second area 12 of the shell. Preferably, the pattern of the body adhesive 44 will substantially surround the absorbent structure located in or on the second area 12 of the shell 14. As shown in FIGS. 19A, 19B, 20, 20A, 22, 23B, 24B and 24C, the body adhesive 44 is applied in a closed pattern, since the entire body adhesive is applied in a continuous fashion around the first area. An "open" pattern of the adhesive is shown in FIG. 25, which shows the adhesive applied in a discontinuous fashion. Additionally, the adhesive may be applied in portions of the first area 11, as seen in FIGS. 23 and 23A. The closed pattern can be advantageous since the body adhesive 44 may form a seal with the body of the user which will assist in preventing leaks from the absorbent article 10. The body adhesive may form a dam, which may prevent leaks from the entire perimeter of the absorbent article.

In one embodiment, as seen in FIGS. 19A, 19B, 20, 20A, 22, 23B, 24B and 24C, the body adhesive 44 may be placed on the entire first area 11, just outside of the absorbent structure 21. In another embodiment, as seen in FIG. 23, the body adhesive 44 may placed along the outer portions of the first area 11 near the periphery of the shell 14. The body adhesive 44 may also be placed on the absorbent structure 21. Generally, however, the body adhesive 44 is confined to being placed on the first area 11 of the shell 14, since placing the body adhesive on an area of the absorbent article 10 that contacts the female genitalia such as the labia majora may cause discomfort to the wearer of the absorbent product.

The adhesive may be applied in a pattern of small discrete dots so as to leave numerous areas free from adhesive. Alternatively, the adhesive may be applied as a continuous bead, or may be applied as a series of semi-continuous beads. Other suitable adhesive patterns may be selected for applying the body adhesive 44 to the body-contacting first area 11 of the absorbent article 10. For example, adhesive patterns can be oval, swirls, various linear or non-linear arrays of adhesive longitudinally, and/or transversely oriented and reticulated webs having unobstructed interstices between the adhesive fibers or combinations thereof. As stated above, the adhesive patterns may be open or closed. The weights of adhesives are limited to less than about 800 $g/m^2$, and generally less than about 400 $g/m^2$. Generally, the weight of the adhesive is at least 20 $g/m^2$. Typically, the adhesive is applied in an amount of about 100 $g/m^2$ to about 400 $g/m^2$. The limitations on the basis weight of the adhesive are important to provide the correct adhesive characteristics for applying directly to the wearer's vulva region and optionally the pubic and perinea regions of the wearer's body. If the basis weight is too high, the absorbent article will have a sticky feeling or otherwise uncomfortable feeling. If the basis weight of the adhesive is too low, there may be insufficient adhesion to the body of the user.

Generally, the body adhesive 44 is applied in a manner that is symmetrical about the longitudinal axis 1 that bisects the absorbent article 10 and divides the absorbent article 10 into substantially equal portions. This symmetrical pattern provides the wearer a balanced feel when wearing the absorbent article 10. The symmetrical pattern also reduces the perception of any associated discomfort when the absorbent article 10 is removed from the body.

Figure 26A:
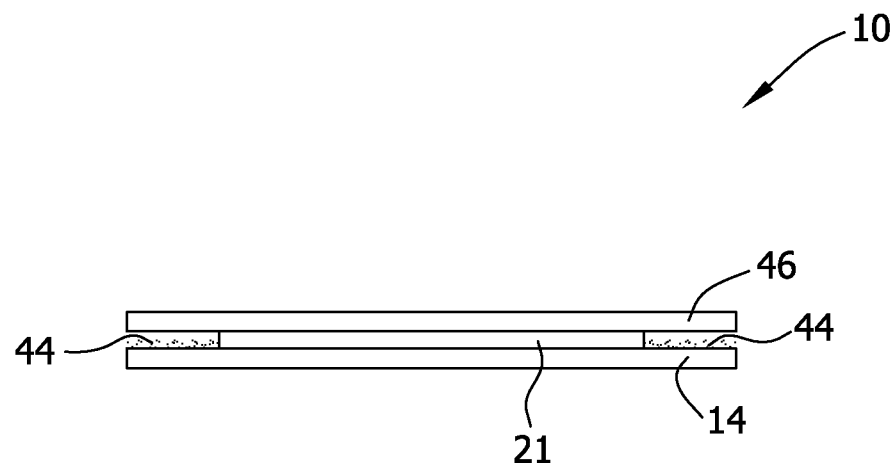
FIGS. 26A, 26B, and 26C each show an absorbent article of the present invention having a release sheet applied thereto.
Figure 26B:
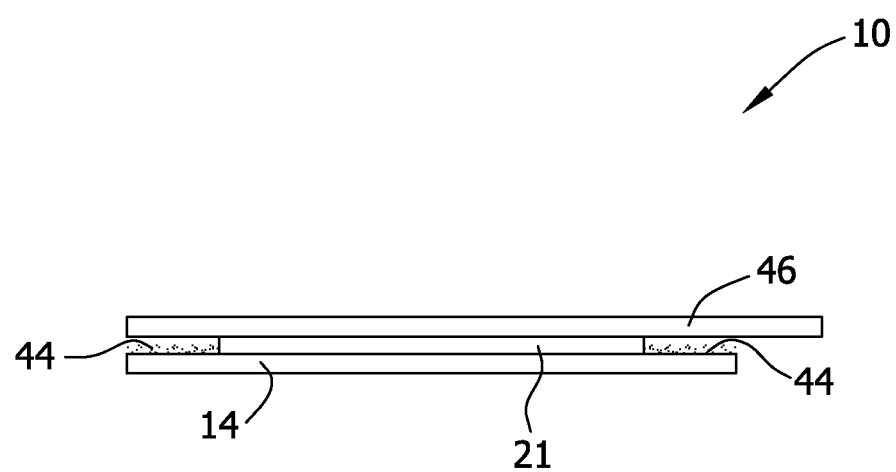
Figure 26C:
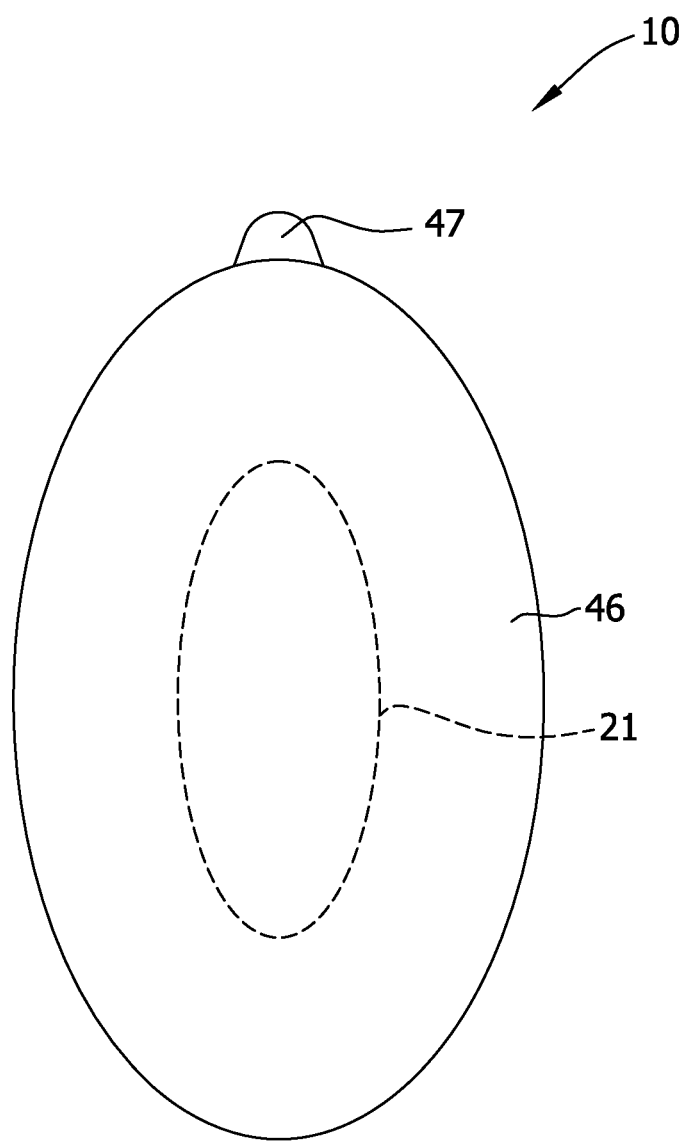

As seen in FIGS. 26A and 26B, to protect the body adhesive 44, a peel sheet or release sheet 46 may be used to prevent the body adhesive 44 from becoming contaminated, thus loosing its ability to stick to the body of a user and/or prematurely adhering to an unintended surface. Suitable materials for use as the release strip 46 are well known in the art and are commercially available. Examples of suitable release sheets 46 include, a silicone coated Kraft paper, a silicone coated film or the like. Other release coatings includes coatings containing polytetrafluoroethylene. The release sheet 46 may extend beyond one or both of the ends and/or sides of the shell, as shown in FIG. 26B. Alternatively, the release sheet 46 may be sized to only cover the body adhesive on the first area 11 of the shell 14, as seen in FIG. 26A. In yet another embodiment, the release sheet 46 may extend beyond the adhesive at one or more locations, such as one of the ends or one of the sides of the shell as seen in FIG. 26C by providing the release sheet 46 with a tab 47 for the user to grasp to remove the release sheet 46 from the absorbent article 10 and the body adhesive 44 on the absorbent article. When the release sheet 46 extends beyond the adhesive, it is generally easier for the user to remove the release sheet to place the absorbent article 10 for use.

Alternatively, the release sheet 46 may be provided with a pressure sensitive adhesive to hold the release sheet 46 in place when the absorbent article is devoid of an adhesive for body attachment. In this configuration, the release sheet 46 serves to protect the absorbent structure and first side of the shell from dirt and damage prior to use.

In another embodiment, the release sheet 46 may not be necessary. For example, the absorbent article may be rolled, folded onto itself or stacked upon each other. In these configurations, the release sheet 46 is not needed. If rolled, the body adhesive 44 will generally contact the second side 17 of the shell 14. The body adhesive 44 should releasably stick to one second side of the shell by readily releasing when unrolled by the user or wearer. In addition, the body adhesive 44 should not leave a residue on the second side 17 of the shell. This should similarly occur when the absorbent articles 10 are stacked upon each other such that the body adhesive 44 of one article will attach the second side of the shell of a second article. In another possible configuration, the absorbent article 10 may be folded along the longitudinal axis 1 of the lateral axis such that the body adhesive 44 in one area comes into contact with body adhesive in another area. In the folded configuration, the body adhesive should be selected such that the body adhesive will release from itself when manipulated by a user.

The dimensions and shape of the shell 14 should be such that it is appropriately sized for its intended use. The same is true for the size and shape of the absorbent structure. Generally, the size and shape of the absorbent structure 21 will dictate the size of the shell 14. The shape of the shell 14 is selected so that the absorbent article will have a comfortable feeling for the user, which providing protection against leaks and preventing the absorbent article from becoming dislodged from the body of the user during use. Generally, the shell will be curved to fit the body of a user. The shell 14 also generally gives the absorbent article 10 its overall size and shape in the longitudinal 1 and lateral 2 directions.

When the absorbent article is intended for use as a pantiliner, a sanitary napkin, or a feminine incontinence article, the shell 14 should be wider and longer than the absorbent structure 21 attached to the second area 12 of the shell 14. The absorbent structure should be at least as wide and as long as the labia majora of the user. As a result, to fit most women, the absorbent structure is longer in the longitudinal direction than it is wide in the lateral direction of the absorbent structure. Generally, for most women, the labia majora are generally between about 40 mm and about 70 mm in width and between about 80 mm and 150 mm in length. Ideally, the absorbent structure should be wider than the labia majora and slightly longer than the labia minora and slightly longer than or equal to the labia majora. Generally, the absorbent should be between about 40 mm and 90 mm in width in the lateral direction and between about 95 mm and about 150 mm in length the longitudinal direction. The shape of the absorbent structure 21 will generally tend to be oblong and may be an oval, a rectangle, tear drop shaped, hourglass shaped, or racetrack shaped. As can be seen in FIGS. 19A, 23, 23B, 24B, 25 and 27, the absorbent structure 21 has a generally elliptical or oval shape to match the size and shape of the vaginal area of most women. An example of a teardrop shaped absorbent is shown in FIG. 19A.

Generally, the shape of the shell 14 may vary from a generally oval shape, as shown in FIGS. 19A and 19B to a shape that is generally hourglass-like, as shown in FIG. 23A. By generally hourglass-like, it is meant a shape in which the sides 19 of the shell 14 converge towards one another at a point away along the longitudinal axis 1 of the shell 14 to form a narrowest portion 33 of the absorbent article. Generally, the hourglass-like shape provides a cut-out for the user's legs. By having an hourglass-like shape, the shell 14 will not be attached to the legs of a user during use. This will provide more comfort for the user of the absorbent article 10. The shape of the shell 14 should be selected such that the absorbent article 10 will be comfortable to wear, while providing very effective leakage protection to the user. The shell 14 and the absorbent structure 21 should be able to adapt to the curvature of a users body during use. Other possible shapes for the shell 14 are also shown in FIGS. 23, 23A, 23B, and 24A. Other shapes not specifically shown may be used, provided that the shape will provide comfort to the user of the absorbent article.

To obtain an effective attachment of the absorbent article to the user, when the absorbent article is used as a sanitary napkin or an incontinence article, generally the width of the of the shell should be at least 10 mm on either side of the labia majora. Generally, the shell 14 of the absorbent article 10 will have a width, in the lateral direction 2, between about 50 mm up to 200 mm or more. Typically, the shell will be between about 60 and 120 mm at its narrowest point. This will allow the shell 14 to have a first area 11 that can be effectively attached to the skin of a user on either side of the labia majora.

Figure 27:
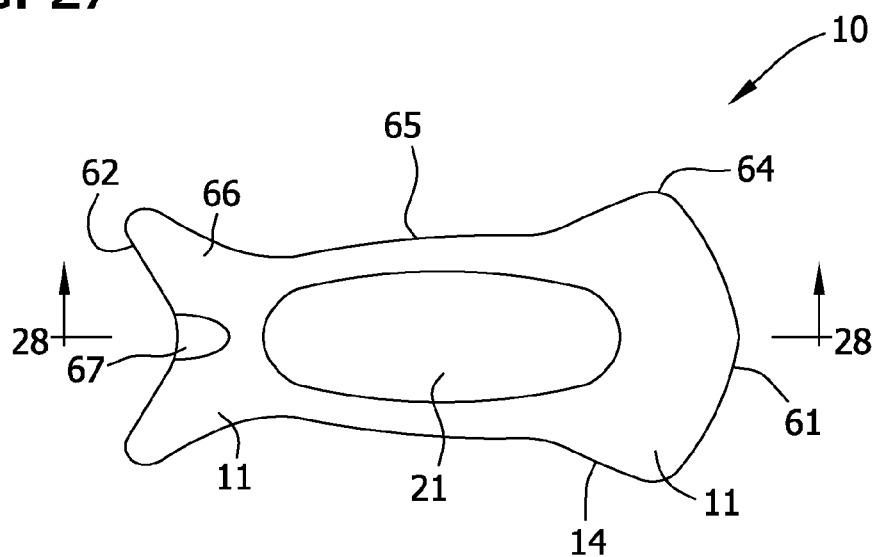
FIG. 27 shows a top view of another absorbent article of the present invention having a design for attachment to specific area of the body.

In addition, the absorbent article 10 may also be configured to have an anterior region 64, a central region 65, and a posterior region 66, as seen in FIG. 27. A particular embodiment is shown in FIG. 26 of an absorbent article having a configuration designed to fit specific areas of the vulva region of a user. By providing specific portions for attachment to specific areas of the body of the user, the absorbent article may be configured to better fit the body of the user. The anterior region 64 of the absorbent article will be the portion of the absorbent article between the absorbent structure 21 and the first end 61 of the absorbent article 10. The posterior region 66 of the absorbent article 10 will be the portion of the absorbent article between the absorbent structure 21 and the second end 62 of the absorbent article 10. Generally, the posterior region 66 will be designed to be placed between the vagina area and the anal area of the user. The anterior region 64 is designed to be placed on the mons Veneris region of a female user. The central region 65 of the absorbent article 10 is designed to cover the vagina area of the user and the skin area surround the lateral sides of the labia majora, when the absorbent article is used as a pantiliner, sanitary napkin, or an incontinence article. In an alternative use, the absorbent article of the present invention may also be used as an underwear replacement, or a guard for a swimming suit.

Figure 28:
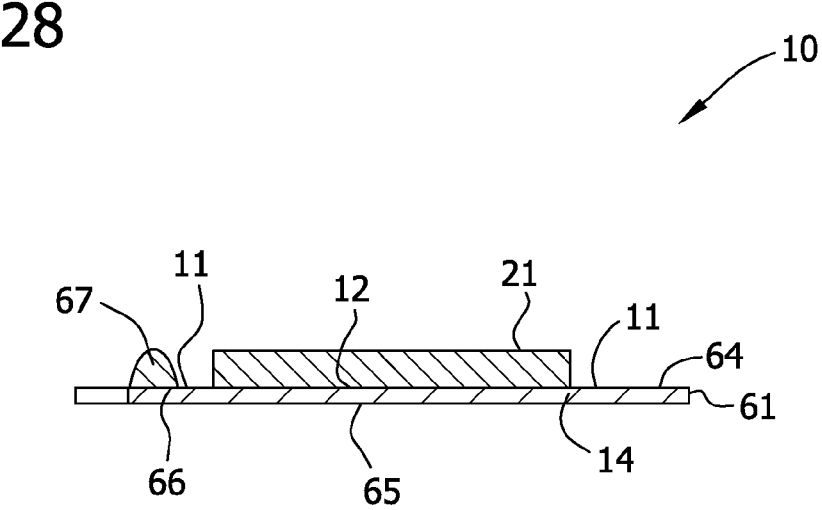
FIG. 28 shows a cross-section view taken along sectional line 28-28 of FIG. 27.

To obtain an effective attachment to the body of the user, the shell 14 can be configured to be anatomically correct for a user. As seen in FIGS. 27 and 28, the shape of the absorbent article 10 is such that it will correctly and securely fit in the vulva region of a user. The general shape of the absorbent article shown in FIG. 28 has been found to effectively attach to the vulva region of female users of the absorbent article. Additional features may be included to ensure an anatomically correct shape. For example, in the posterior region of the absorbent article 10, more particularly, the posterior region of the shell on the first side 15, the shell 14 may be imparted with a three-dimensional protrusion 67, as shown in FIGS. 27 and 28. The protrusion 67 acts to fit comfortably in the perineum region of the user. The protrusion 67 may be formed from the shell material or from the body adhesive 44. By providing the three-dimensional protrusion 67, the absorbent article can effectively fit to the typical body shape of the female user, thereby preventing leaks from the posterior region of the absorbent article. The protrusion 67 may also serve as a guide to the user in placement of the absorbent article 10 on the body prior to use.

Figure 29A:
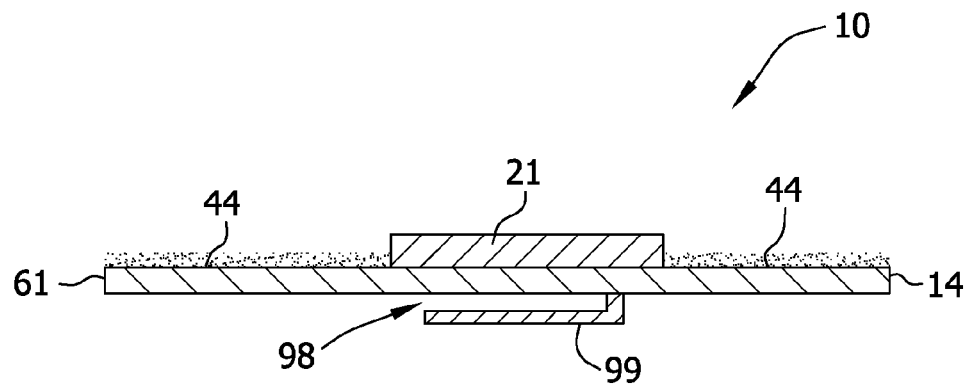
FIGS. 29A and 29B show embodiments of the present invention with placement guides.
Figure 29B:
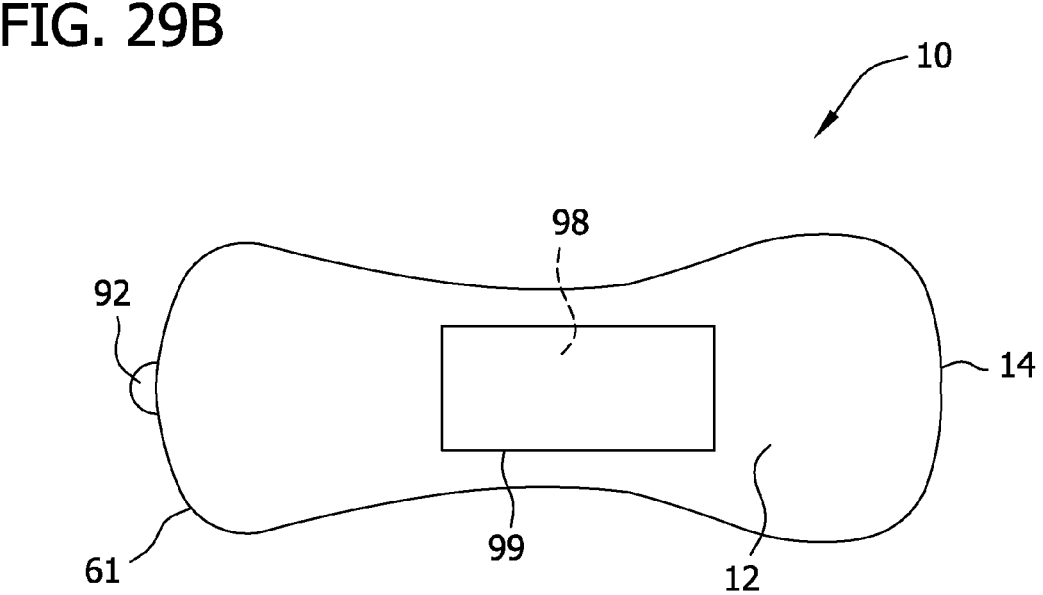
Figure 30:
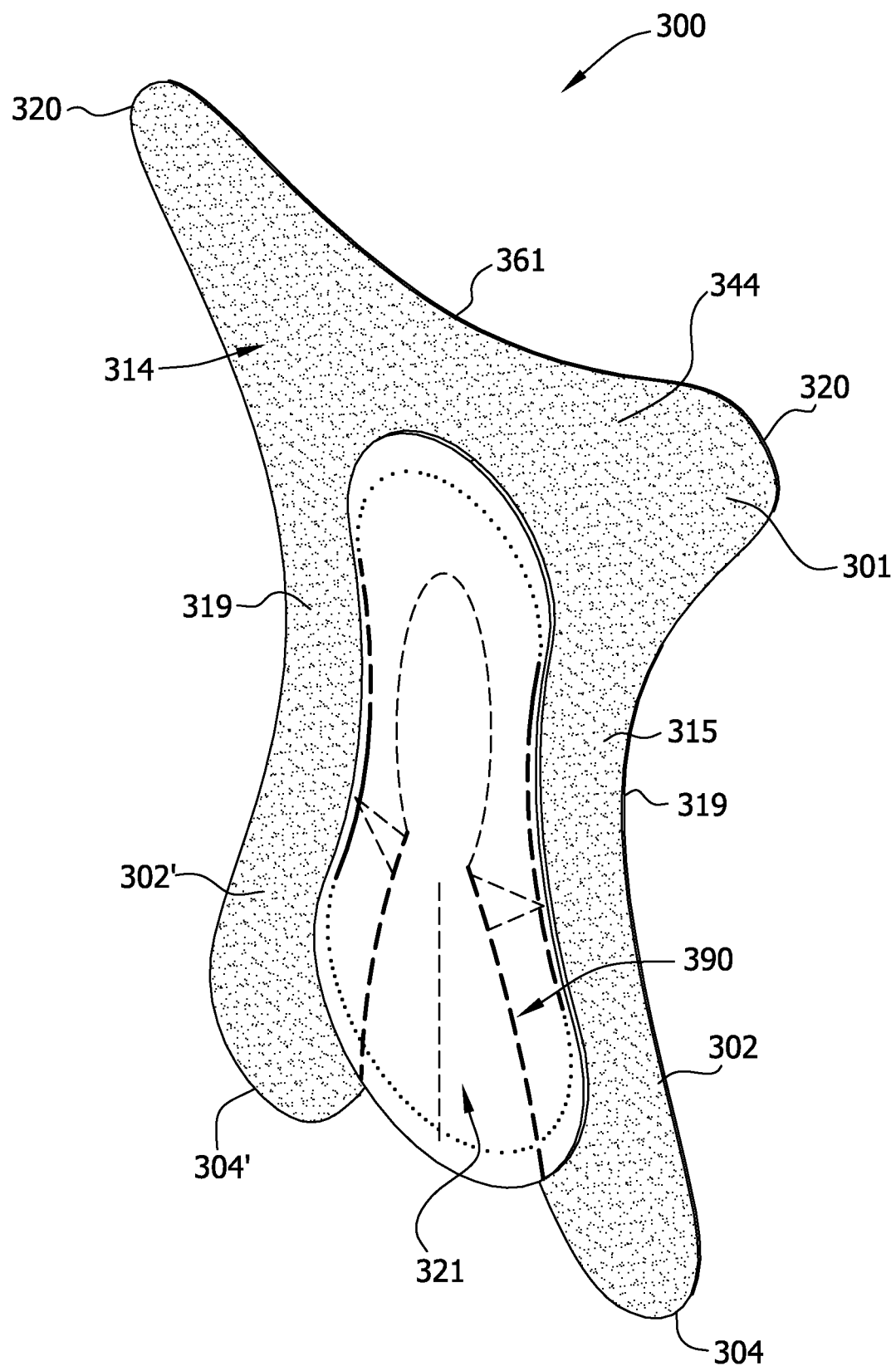
FIG. 30 shows a perspective view of another embodiment of an absorbent article of the present invention.

The absorbent article 10 may have other features that aid the user in placing and removing the absorbent article from the body. As seen in FIGS. 29A and 29B, the second side 12 of the shell 14 may be provided with positioning aids, such as a finger pocket 99, or finger grooves in the shell material. The finger pocket 99 has an opening 98 toward the anterior region 64 or first end 61 of the absorbent article 10. The pocket 99 gives the user a location to place her fingers during placement of the absorbent article 10 onto the user's body. The pocket 99 may be an opening wide enough for the user to place at least two fingers in the pocket. Alternatively, there may be two or more openings which allows the user to place only one finger in each opening. Other similar positioning aids may be used to help guide a user to properly place the absorbent article for use. For example, grooves may be placed in the second side 12 of the shell 14 opposite the absorbent structure. This may allow the user to feel the location of the absorbent structure relative to the vulva region during application of the absorbent article 10 to the vulva region of the body. The pocket 99 may also assist the user in removing the absorbent article from their body.

The absorbent article 10 may also be provided with a removal aid that provides the user with an easy way to grasp and remove the absorbent article applied to the body. One particular removal aid is shown in FIG. 29B including a tab 92 located on the first end 61 of the shell that is not adhered to the body or is devoid of adhesive. Alternatively, other removal aids, such as having an area of the first end 61 being devoid of the body attaching adhesive 44. Other types of removal aid that may be present include loops, and pull strings. The removal aid allows the user to effectively begin the process of gentling removing the absorbent article from the body of the user, without the need of having to find a portion of the shell that may not be completely attached.

Other features or additives may be incorporated into the absorbent article. For example, the absorbent article may contain an odor control agent, or a fragrance, skin wellness agents, and other similar additives currently used in currently available absorbent articles. Any odor control agent or, fragrance known to those skilled in the art may be used in the absorbent article. The odor control agent or fragrance may be added in various components of the absorbent article, including the shell 14, the absorbent structure 21 of the body adhesive 44. Skin wellness additives may be added onto the absorbent structure, any portion of the first area 15 of the shell not attached to the user or in the body adhesive 44.

Generally, to apply the absorbent article 10 to the body of a user, the release sheet 46 protecting the absorbent structure and adhesive, if present, is removed from first surface of the shell. Next, the user positions the absorbent structure on the portion of the body in which absorbency is needed. If positioning pockets or other positioning aids are present on the absorbent structure, the user may optionally use these positioning aids to properly place the absorbent article for use. In the case of sanitary napkins and incontinence absorbent articles for females, the absorbent is positioned over the vagina area such that the absorbent structure will absorb body fluids. The user then checks to ensure that the first area 11 of the shell or the adhesive 44, if present, is contacting the skin around the vagina area.

If the absorbent article is intended to have a front and a back portion, the user first identifies the anterior region 64 and/or the posterior region 66 of the absorbent article. To aid in identification of the anterior and posterior regions, indicia located on the release sheet, shell, or absorbent structure to indicate the anterior region and/or posterior region of the absorbent article may be present. Indicia can be simply lettering or a picture to indicate the front or back of the absorbent article. Once anterior region and posterior region are identified by the user, the user places the absorbent article in the same manner described above.

In each case, the absorbent structure, which is designed to cover the labia majora of the user, may be positioned with the aid of the absorbent structure. More specifically, the absorbent structure, when sized and shaped to the approximate size of the labia majora, can serve to guide the placement of the absorbent structure over the labia majora. Once properly placed, pressure is applied by the user to the second surface of the shell which will allow the first surface of the shell to contact the skin of the user, or to allow any adhesive applied to the first surface to be applied to the skin of the user.

By having the absorbent article 10 attached to the body of a user, the absorbent article 10 will tend to move with the skin of the user. This results in a comfortable to wear absorbent article that will be less likely to leak than conventional absorbent articles. The absorbent article has a very close fit to the body, which may provide improved discretion for the user.

Other benefits of the absorbent article 10 may also be provided. For example, when the first side of the shell has an adhesive applied thereto, upon removal of the absorbent article after user, the user may fold the first side of the shell onto itself to dispose of the used absorbent article. An effective seal may be formed around the perimeter of the shell, thereby effectively encapsulating the absorbent structure within a closure. As a result, any odors associated with the absorbed fluids will be contained within the shell material.

Figure 31:
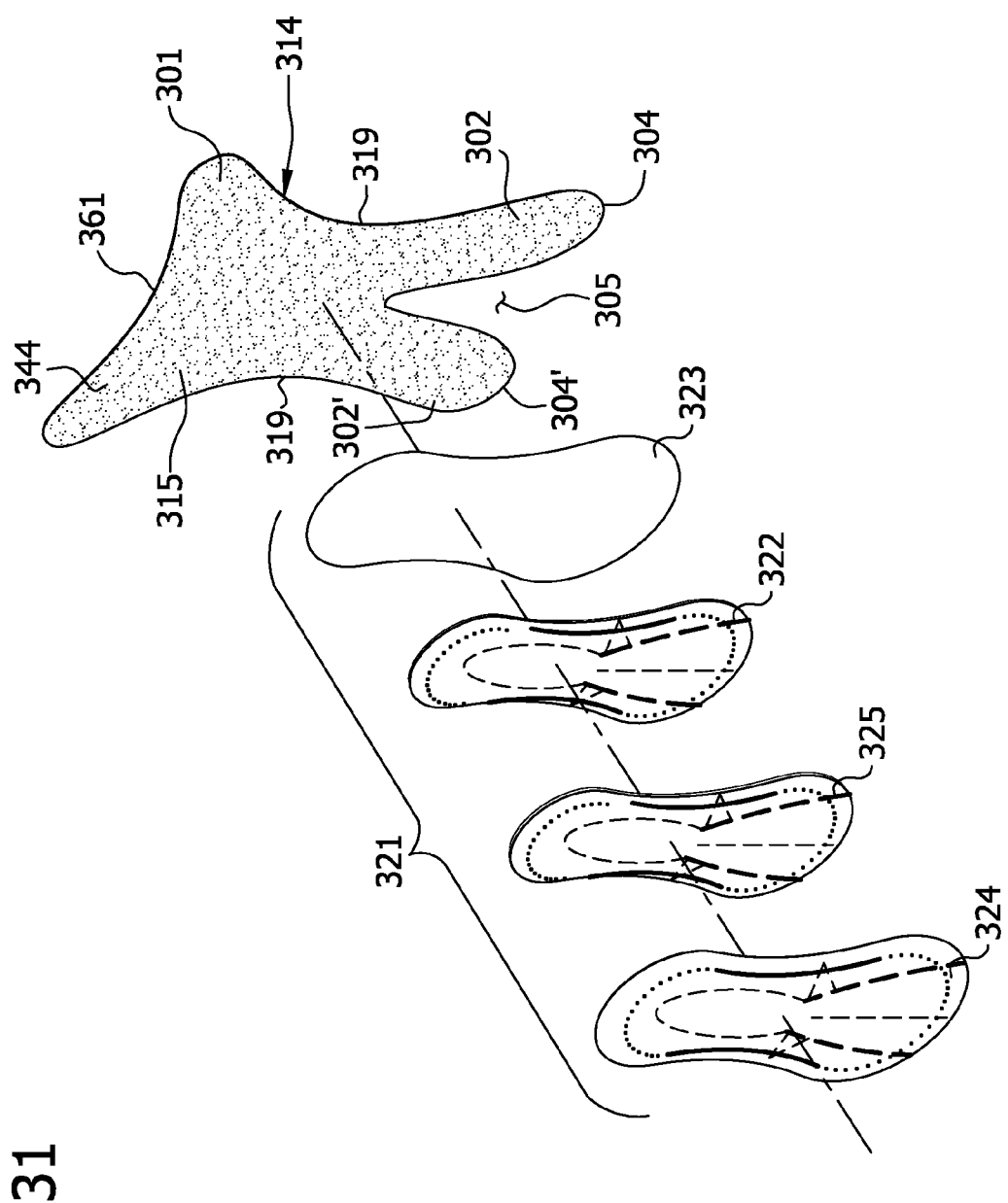
FIG. 31 shows an exploded perspective of the absorbent article of FIG. 30.
Figure 32:
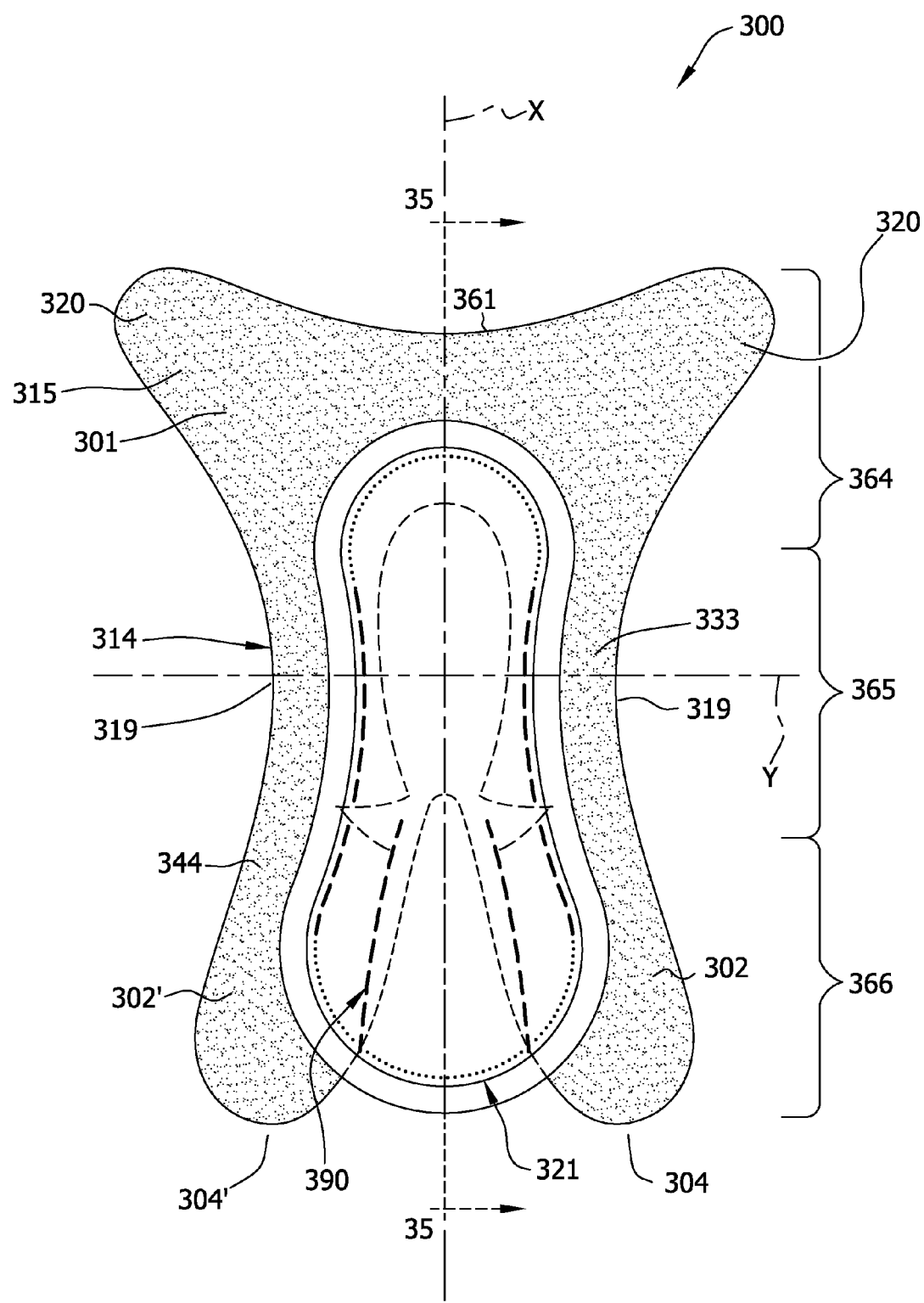
FIG. 32 shows a top view of the absorbent article.
Figure 33:
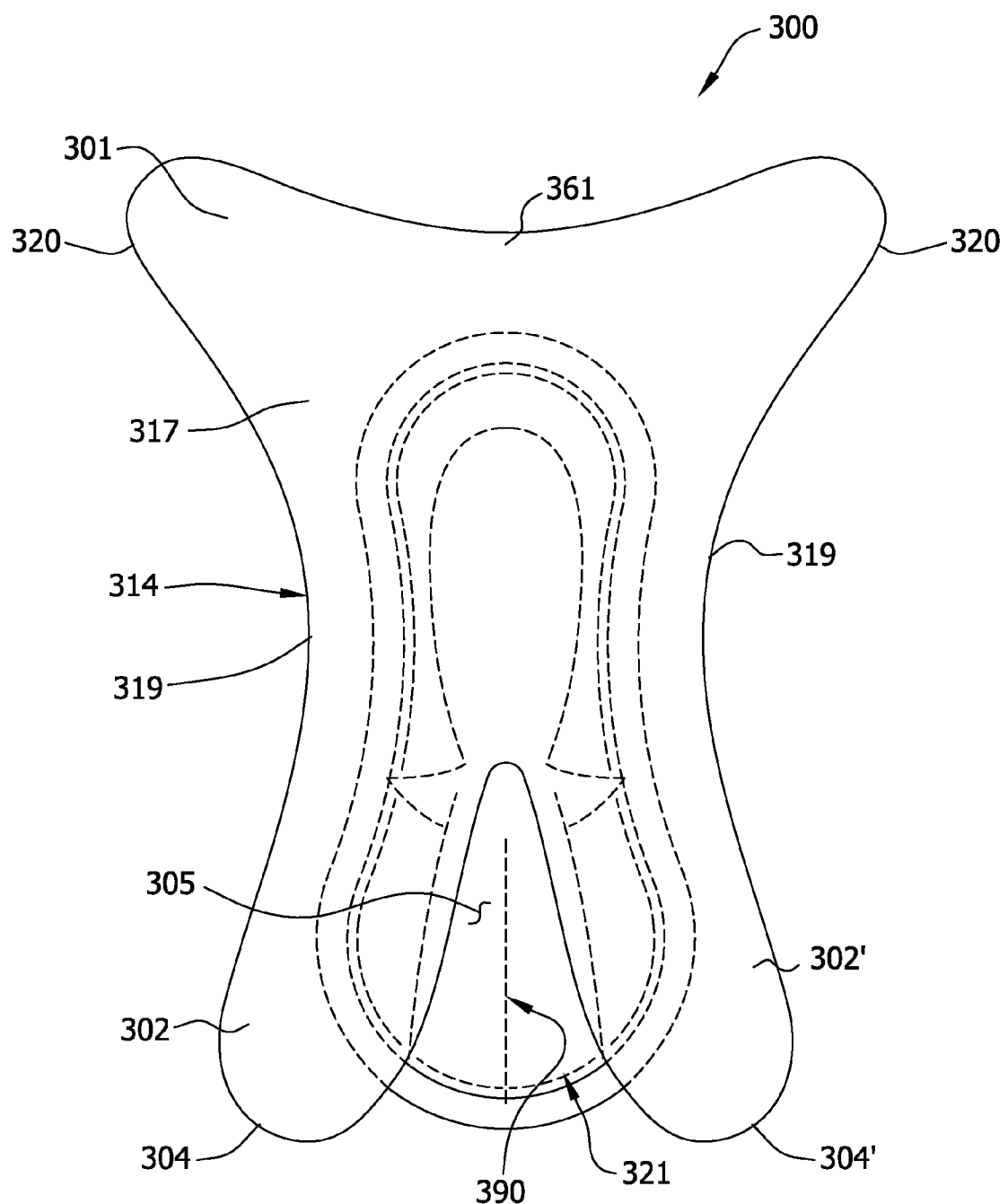
FIG. 33 shows a bottom view of the absorbent article.
Figure 34:
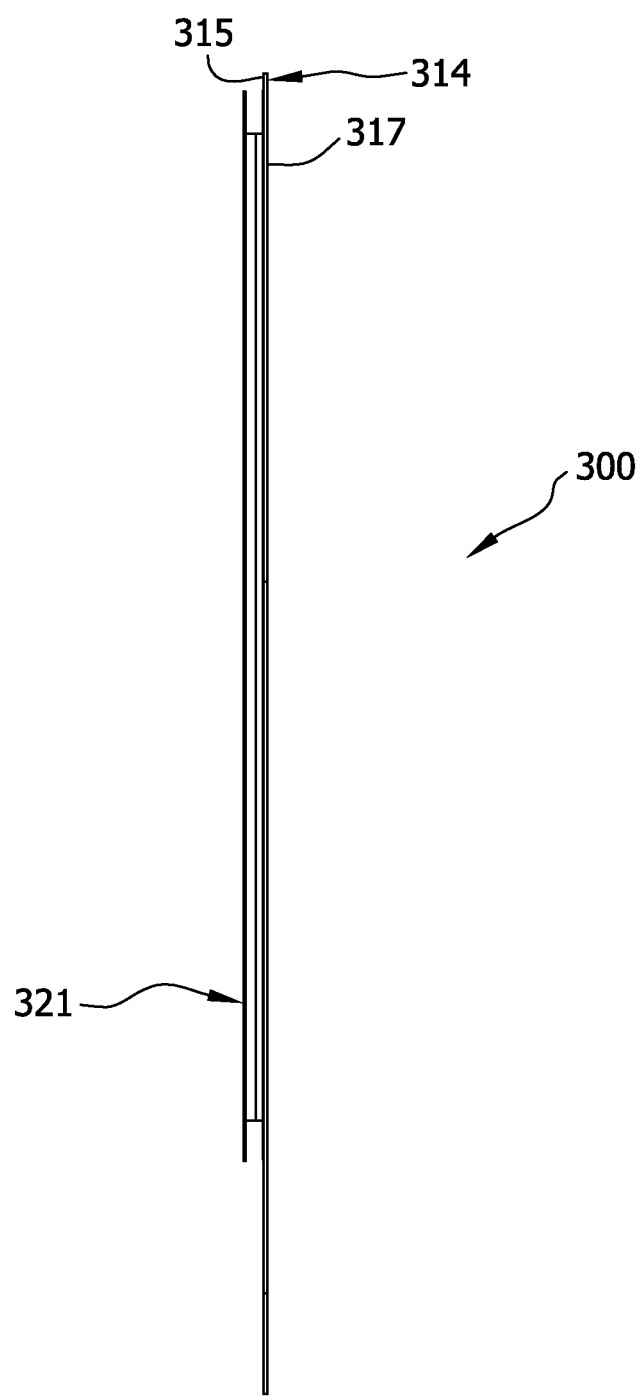
FIG. 34 shows a side view of the absorbent article.
Figure 35:
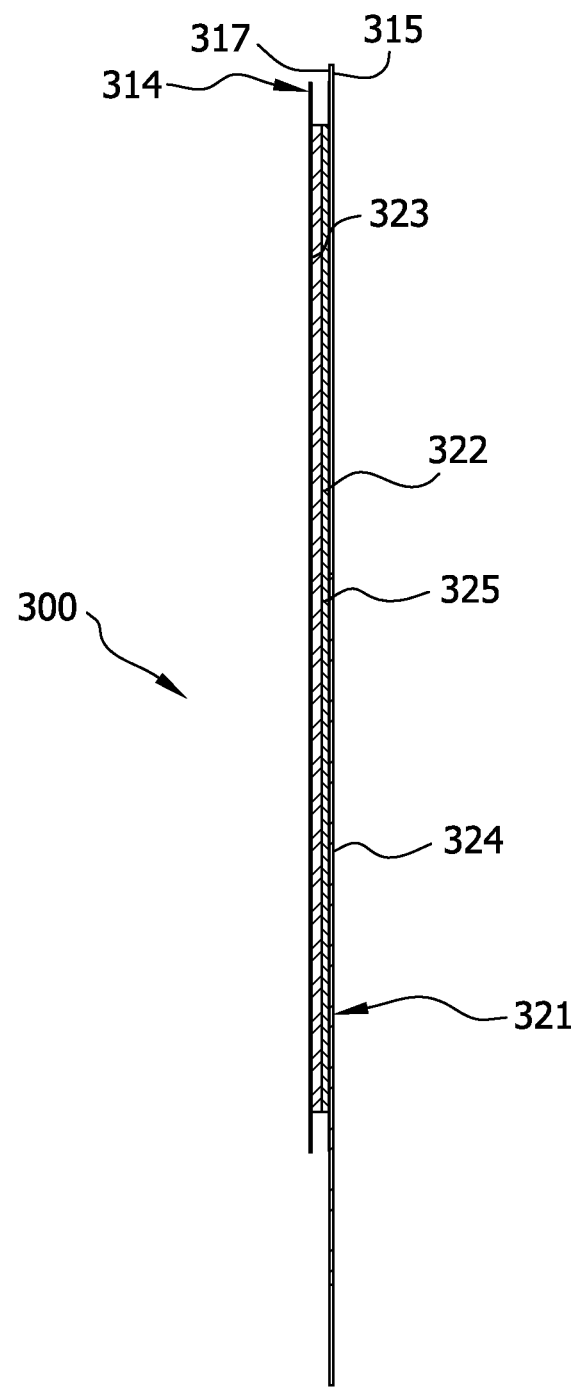
FIG. 35 shows a side cut-away view of the absorbent article taken along line 35-35 of FIG. 32.

In another embodiment, a body adhesive absorbent article 300, which is illustrated in FIGS. 30-38, comprises a shell 314 and an absorbent structure 321 and has a longitudinal axis X and a transverse axis Y. The shell 314 of this embodiment is substantially the same as the shell 314 illustrated in FIGS. 11-17. Thus, the shell 314 has a first region 301, a pair of lateral side regions 302, 302' extending from the first region, and an opening 305 (FIG. 32) extending longitudinally at least in part between the side regions. The shell 314 also has a first side 315, which defines a body-facing surface (FIG. 32), and a second side 317, which defines a garment-facing surface (FIG. 33). In the illustrated embodiment, the first side 315 of the shell 314 has a body adhesive 344 on at least a portion thereof for adhering the absorbent article 300 directly to the wearer's skin, and particularly, to a female wearer's skin surrounding her vulva region. The body adhesive 344 contacts the skin and hair, if present, in the vulva region and possibly the pubic region and/or the perinea region of the wearer's body, thereby supporting and holding the shell 314 and an absorbent structure 321 against the body of the wearer during use. A peel sheet or release sheet (not shown) may be used to prevent the body adhesive 344 from becoming contaminated, thus losing its ability to stick to the body of the wearer and/or prematurely adhering to an unintended surface.

With reference to FIG. 32, the absorbent article 300 (and hence the shell 314) can be suitably divided into three general longitudinal regions: an anterior region 364, a posterior region 366, and a central region 365 extending longitudinally between and interconnecting the anterior and posterior regions. Each of these regions 364, 365, 366 is sized and shaped for alignment with different body regions of a wearer of the absorbent article. Specifically, the anterior region 364 of the article 300 is adapted to be disposed adjacent the wearer's lower abdomen region. The central region 365 is adapted to be disposed between the upper thigh region of the wearer to cover the wearer's perineum region and vaginal region. The posterior region 366 of the article 300 is adapted to be disposed in the gluteal region of the wearer. In the illustrated embodiment, the anterior region 364, the central region 365, and the posterior region 366 of the absorbent article 300 are of roughly equal length, with each region corresponding generally to about ⅓ of a total length of the absorbent article 300. It is contemplated that two or all three of the article regions 364, 365, 366 may instead be of unequal lengths depending on the desired fit and the intended body placement of the article without departing from the scope of this invention.

The absorbent structure 321 is suitably adhered to or otherwise bonded to the first side (i.e., the body-facing surface) 315 of the shell 314 and is sized and located relative to the shell such that the shell extends both longitudinally and transversely outward beyond the periphery of the absorbent structure in at least the anterior region 364 and the central region 365, and more suitably in at least a portion of the posterior region 366 as well. The absorbent structure 321 is offset longitudinally, i.e., not centered lengthwise on the transverse or lateral axis of the absorbent article, such that the shell 314 extends longitudinally outward beyond the absorbent structure a greater distance in the anterior region 364 of the article 300 than in the posterior region. It is understood, though, that the absorbent structure 321 may be longitudinally centered so that the shell 314 extends equally longitudinally outward beyond the absorbent structure, or may be offset longitudinally toward the anterior region 364 so that the outward longitudinal extension of the shell beyond the absorbent structure is greater in the posterior region 365 than in the anterior region without departing from the scope of this invention.

As illustrated in FIG. 32, the anterior region 364 of the absorbent article 300 comprises the first region 301 of the shell 314 and includes a portion of the absorbent structure 321. Since much of the first side (i.e., the body-facing surface) 315 of the shell 314 is exposed (i.e., not covered by the absorbent structure 321) in the anterior region 364 of the absorbent article 300, a relatively large surface area of the first side of the shell has body adhesive 344 applied thereto for adhering the shell, and hence the absorbent article, to the wearer.

A first end 361 of the absorbent article 300, and more particularly a longitudinal edge of the anterior region 364 defining this first end of the absorbent article 300, is suitably contoured along the width of the shell at this first end to accommodate the lower abdomen region of the wearer. In the illustrated embodiment, for example, the longitudinal extent (e.g., length) of the shell 314 relative to the transverse axis of the article is non-uniform across the width of the shell at the first end 361 of the article, and more suitably increases as the shell extends transversely outward from the longitudinal axis of the article to transversely, or laterally opposite sides 319 of the article and more particularly laterally opposite side edges of the shell. Accordingly, a greatest longitudinal extent of the shell 314 is generally adjacent the intersection of the longitudinal end 361 with the respective sides 319 of the article (i.e., the shell in the embodiment of FIG. 32). More suitably, the longitudinal edge of the shell 314 (i.e., at first end 361 of article 300 in the illustrated embodiment) is generally arcuate as it extends across the width of the shell at its longitudinal edge. It is understood, however, that the contour of the longitudinal edge of the shell 314 in the anterior region 364 of the article may be V-shaped, U-shaped, or other suitable shape without departing from the scope of this invention. The contoured longitudinal edge of the shell 214 (i.e., first end 361 of the article 300 in the illustrated embodiment) thus broadly defines a recess in the anterior region 264 of the article (and thus of the shell in this instance).

The sides 319 of the illustrated article 300 are suitably defined by transversely opposite side edges of the shell 314. These side edges of the shell 314 are contoured so that the overall width of the article 300 (i.e., the distance between the transversely opposite sides 219 thereof), and more particularly the width of the shell in the illustrated embodiment, is non-uniform along the length of the article to define leg cutouts for accommodating the upper thighs of the wearer. In one suitable embodiment, the width of the article 300 and hence the shell 314 increases from a narrowest width in the central region 365 of the article toward each of the longitudinally opposite ends (361 and 304, 304') of the article. Still more suitably, the width of the article 300 and more suitably the shell 314 is also greater in the anterior region 364 of the article than in the posterior region 366. In the illustrated embodiment, for example, a greatest width of the article 300 is defined by the transverse side edges of the shell 314 adjacent the longitudinal edge of the shell (e.g., first end 361 of the article 300) in the anterior region 364 of the article.

In the embodiment illustrated in FIG. 32, the sides 319 of the article 300 and more particularly the transverse side edges of the shell 314 are generally arcuate along substantially the entire length of the article. Alternatively, the sides 319 may be arcuate along only a portion of the length of the article. It is also understood that the sides 319 defining the leg cutouts may be V-shaped, U-shaped or other suitably shape, or it they may be uniform (e.g., straight or longitudinal) along substantially the entire length of the article 200. It is also understood that the sides 319 of the article may be contoured to define article 300 widths other than those set forth above without departing from the scope of this invention. It is further understood that the greatest width of the article 300 may be other than in the anterior region 364, and/or the narrowest width may be other than in the central region 365 of the article and remain within the scope of this invention.

Still referring to FIG. 32, the contoured longitudinal edge of the shell 314 (e.g., first end 361 of the article 300) at the anterior region 364, together with the contoured transverse side edges of the shell (e.g., article sides 319) where these side edges generally intersect the longitudinal edge of the shell, define a pair of transversely spaced tabs 320 in the anterior region. Each tab 320 has a central axis extending in part transversely outward of the shell 314 and in part longitudinally outward of the shell. Each of the tabs 320 suitably has body adhesive 344 on the body-facing surface (e.g., first side 315) for adhering the tabs directly to the wearer and more suitably to the abdomen region of the wearer. In one particularly suitable embodiment, the tabs 320 are sized to extend to a region of the wearer that has little or no pubic hair to facilitate better adherence to the wearer's skin.

Figure 36:
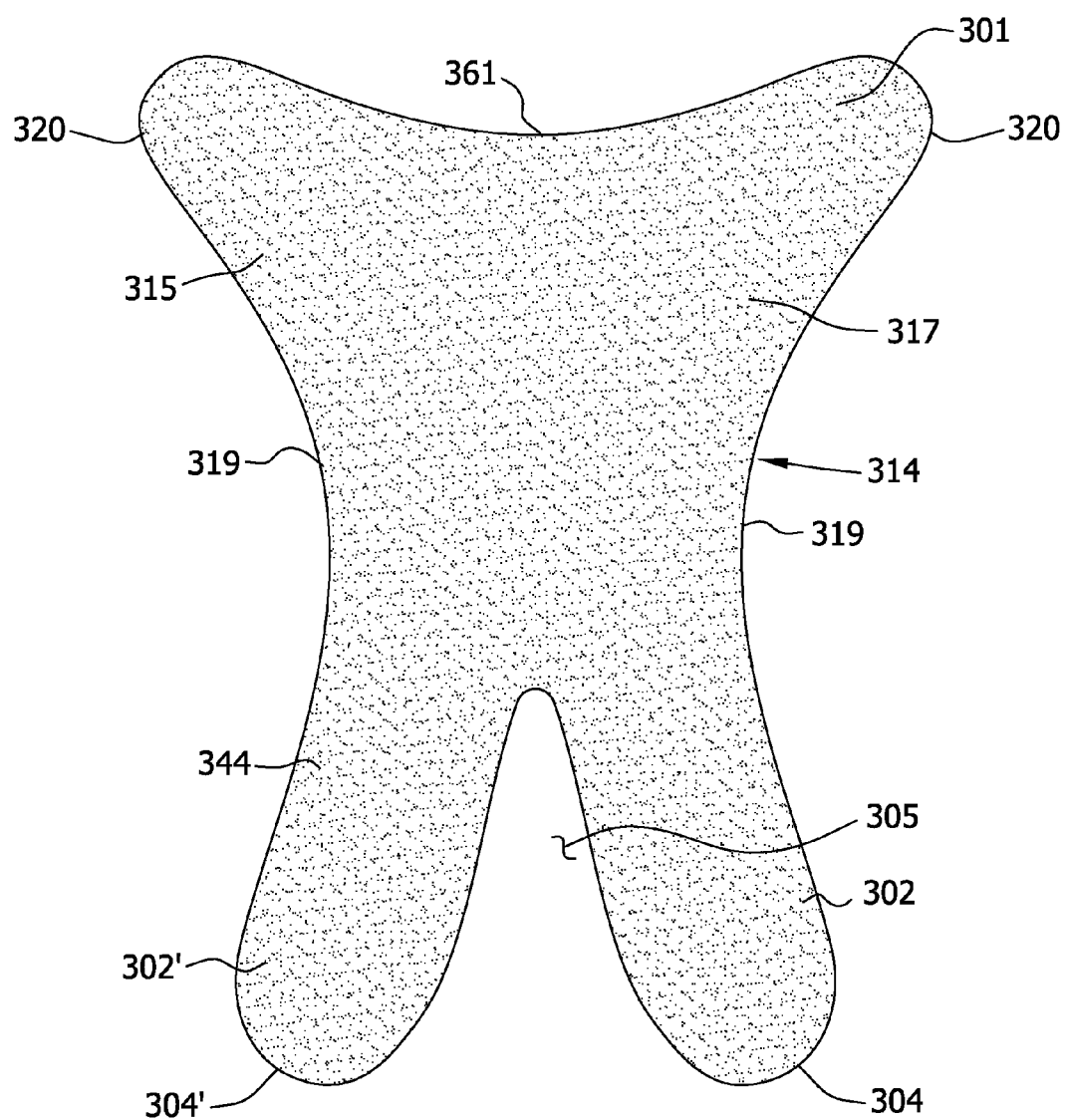
FIG. 36 shows a top view of a shell of the absorbent article.

With reference now to FIG. 36, the posterior region 366 of the absorbent article 300 includes the opening 305 in the shell 314 with portions of the lateral side regions 302, 302' broadly defining a pair of transversely spaced tabs disposed on opposite sides of the opening. The posterior region 366 disposition of these tabs is such that the tabs are aligned generally with the buttocks of the wearer rearward of the perineal region. In the illustrated embodiment, the opening 305 is in the form of a generally V-shaped ingress extending longitudinally on the longitudinal axis of the article 300 such that the tabs are free to flex relative to the central region 365 of the article and generally independent of each other to accommodate normal movement of the wearer's thighs and buttocks. It is understood, however, that the opening 305 can be larger or smaller than illustrated in FIG. 36 without departing from some aspects of this invention.

Figure 37:
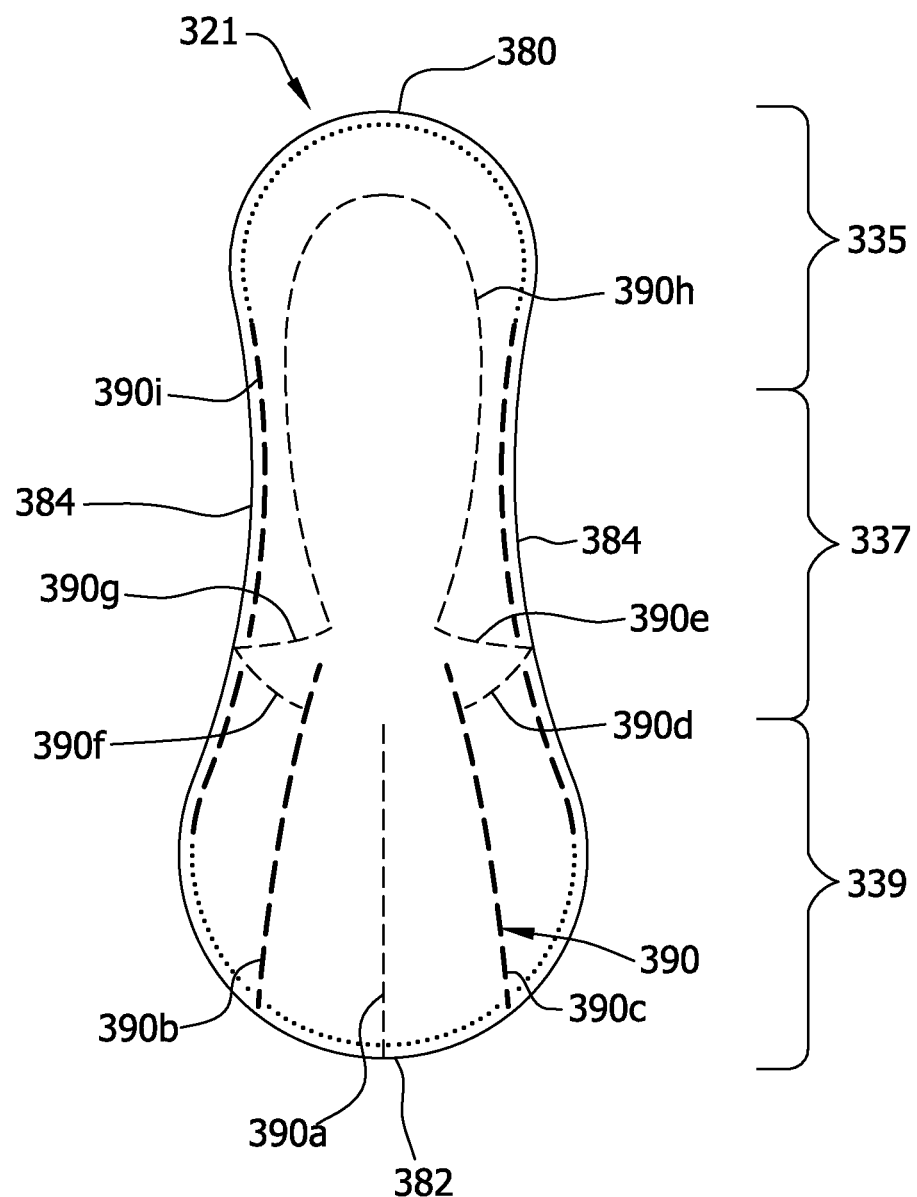
FIG. 37 shows a top view of an absorbent structure of the absorbent article.

Turning now to FIG. 31, the absorbent structure 321 can comprise a single layer structure (not shown) or a multiple layer structure. The illustrated absorbent structure 321, for example, is a multiple layer structure comprising an absorbent core 322, an intake layer 325, a top sheet 324, and a liquid impermeable backsheet 323. As seen in FIG. 37, the illustrated absorbent structure is generally hourglass shaped but it is also understood that the absorbent structure 321 may be formed in any suitable shape without departing from the scope of this invention. As a result of its generally hourglass shape, the illustrated absorbent structure 321 has an upper portion 335 (broadly, an "end portion"), a narrower middle portion 337, and a wider lower portion 339 (broadly, another "end portion"). The absorbent structure 321 has a semi-circular upper edge 380, a semi-circular lower edge 382, and opposite, concave side edges 384 extending between the upper and lower edges. The upper edge 380, the lower edge 382, and the side edges 384 collectively define a periphery of the absorbent structure 321.

With reference to FIG. 37, the absorbent structure 321 includes lines of weakness, indicated generally at 390, to facilitate folding of the absorbent structure in the middle and lower portions 337, 339 while inhibiting folding of the absorbent structure in the upper portion 335 during wear. In particular, the lower portion 339 includes a first line of weakness 390a extending generally along the longitudinal axis of the absorbent structure and two second lines of weakness 390b, 390c spaced from and flanking the first line of weakness. The first line of weakness 390a extends longitudinally from about the lower edge 382 of the absorbent structure 321 to about the transition from the lower portion 339 to the middle portion 337 of the absorbent structure. The second lines of weakness 390b, 390c converge slightly transversely inward as they extend longitudinally away from the lower edge 382 of the absorbent structure 321 to the middle portion 337 of the absorbent structure.

The middle portion 337 of the absorbent structure 321 includes a third line of weakness 390d, a fourth line of weakness 390e, a fifth line of weakness 390f, and a sixth line of weakness 390g. The third and fourth lines of weakness 390d, 390e extend from approximately the same location adjacent the right side edge 384 (as viewed in FIG. 37) of the absorbent structure 321 and diverge as they extend transversely inward toward the longitudinal axis of the absorbent structure. As a result, the third and fourth lines of weakness 390d, 390e cooperatively form a generally V-shape. The fifth and sixth lines of weakness 390f, 390g extend inward toward the longitudinal axis of the absorbent structure in the same manner as the third and fourth lines of weakness 390d, 390e but extend inward from the left side edge 384 (as viewed in FIG. 37) of the absorbent structure. The third and fifth lines of weakness 390d, 390f terminate adjacent and more suitably intersect respective ones of the second lines of weakness 390b, 390c.

The upper portion 335 of the absorbent structure 321 includes a seventh line of weakness 390h that has a generally inverted U-shape. The seventh line of weakness 390h extends into the middle portion 337 of the absorbent structure 321 and has ends that terminate adjacent the fourth and sixth lines of weakness 390e, 390g. As seen in FIG. 37, the seventh line of weakness 390h is spaced inward from the periphery of the absorbent structure. An eighth line of weakness 390i extends adjacent to the entire periphery (i.e., along the edge margin at the upper edge 380, the lower edge 382, and side edges 384) of the absorbent structure 321.

In the illustrated embodiment, the lines of weakness 390 are formed by embossing dashed or dotted lines in the absorbent core 322, the intake layer 325, and the top sheet 324 (FIG. 31). As seen in FIG. 37, the size (i.e., length and width) of the individual dashes and dots (broadly, "embossing elements") that define the lines of weakness 390 can be varied to alter the characteristics (i.e., resistance to folding) and appearance of the line of weakness. The spacing between the individual dashes and dots can also be varied for the same reasons. The characteristics of the lines of weakness 390 can be altered be varying the size and/or spacing of the dashes/dots along the length of a single line of weakness or by having multiple lines of weakness with different sized or spaced dashes/dots defining the lines of weakness. It is understood that the lines of weakness 390 can be formed in other ways besides embossing, including cutting, perforating, bonding, mechanical thinning, or other processes as are known in the art. In the illustrated embodiment, the backsheet 323 is free from the lines of weakness 390. It is understood, however, that all or fewer layers of the absorbent structure 321 may contain the lines of weakness 390.

In one suitable embodiment, the lines of weakness 390 are formed by embossing dashed or dotted lines in the top sheet 324 and intake layer 325 and by cutting (e.g., slitting, perforating) the absorbent core 322. In one particularly suitable embodiment, the embossed lines of weakness 390 formed in the top sheet 324 and intake layer 325 are aligned with the cut lines of weakness formed in the absorbent core 322. It is understood that the various layers (i.e., the absorbent core 322, the intake layer 325, the top sheet 324, and the backsheet 323) of the absorbent structure 321 can have lines of weaknesses 390 formed in the same way or in different ways. It is also understood that one or more of the layers of the absorbent structure 321 can be free from lines of weakness 390.

With reference again to FIG. 32, the absorbent structure 321 is secured to the first side (i.e., body-facing surface) 315 of the shell 314, such that at least a portion of the absorbent structure covers the opening 305 in the shell. The absorbent structure 321 may be attached to the shell 314 in a permanent manner, meaning that the absorbent structure is generally intended not to be removable by the wearer of the absorbent article 300. Alternatively, the absorbent structure 321 can be removably and, in some embodiments, refastenably attached to the shell 314 such that the absorbent structure can be removed (and in some embodiments reattached) by the wearer.

The shell 314 and absorbent structure 321 are sized relative to each other such that a portion of the shell extends outward beyond the peripheral edge of the absorbent structure along at least a portion of the peripheral edge of the absorbent structure. In this manner, a portion of the shell 314 about the periphery of the absorbent structure 321 is uncovered with the first side (i.e., body-facing surface) 315 of the shell exposed and available for adhering to the wearer. For example, the shell 314 in one suitable embodiment extends outward beyond the peripheral edge of the absorbent structure 321 at least in the anterior region 364 and central region 365, and more suitably also in a portion of the posterior region 366. In one suitable embodiment, the entire first side 315 of the uncovered portion of the shell 314 has body adhesive 344 thereon for adhering the shell and thereby the absorbent article 300 to the wearer.

As illustrated in FIG. 32, the distance that the shell 314 extends outward beyond the peripheral edge of the absorbent structure 321 is suitably non-uniform about the periphery of the absorbent structure. More particularly, the shell 314 extends transversely outward beyond each of the side edges 384 of the absorbent structure 321*a* greater distance in the anterior region 364 of the article 300 than in the central region 365. It is understood that shell 314 may extend a uniform distance outward of the absorbent structure 321, or may extend outward according to a different pattern than illustrated in FIG. 32, and remain within the scope of this invention. It is also understood that less than the entire exposed area of the shell 314 can have body adhesive 344 thereon. It is further understood that body adhesive can be applied to the absorbent structure 321 to adhere or partially adhere the absorbent structure to the wearer's skin.

Figure 38:
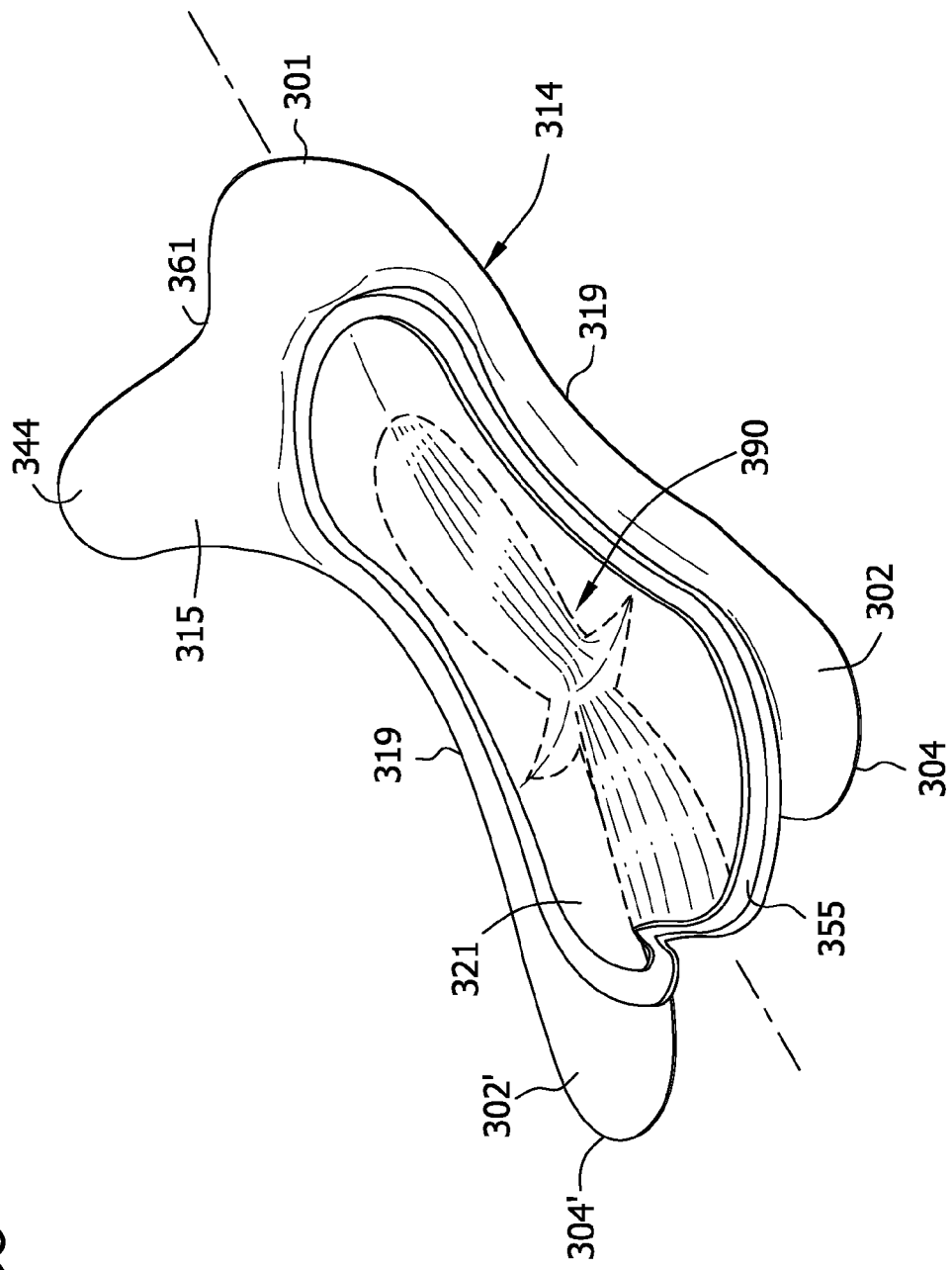
FIG. 38 shows a perspective view of the absorbent article of FIG. 31 in a wear configuration.

A wear configuration of the absorbent article 300 is illustrated in FIG. 38. In use, the portions of the shell 314 having body adhesive 344 thereon and extending transversely outward beyond the periphery of the absorbent structure 321 are adhered directly to the body (e.g., skin, pubic hair) of the wearer. In one suitable embodiment, the first region 301 of the shell 314 is adhered to the lower abdomen region of the wearer, the portion of the shell in the central region 365 of the article 300 is adhered to the vaginal region of the wearer (i.e., between the wearer's upper thighs), and the lateral side regions 302, 302' of the shell are adhered to the gluteal region of the wearer. More specifically, the lateral side regions 302, 302' are adhered in spaced relationship with each other to the wearer's buttocks. The opening 305 in the shell 314 generally aligns with the wearer's gluteal cleft.

The shell 314 supports the absorbent structure 321 in close proximity to the wearer's body. More specifically, the upper portion 335 and most of the middle portion 337 of the absorbent structure 321 is supported by the shell 314 in close proximity to the vaginal and perineum regions of the wearer. The seventh, generally U-shaped, line of weakness 390*h* inhibits the upper portion 335 of the absorbent structure from folding, bending, or otherwise deforming longitudinally to thereby inhibit the absorbent structure from entering a cleft, fold, cavity, or opening in the vaginal region of the wearer. That is, the seventh line of weakness 390*h* of the illustrated embodiment maintains the absorbent article 300 exterior of the vaginal region of the female wearer.

The first and second lines of weakness 390*a*-390*c* allow the absorbent structure 321 to conform to the gluteal cleft of the wearer. In particular, the first line of weakness 390*a* in the lower portion 339 of the absorbent structure 321 defines a peak (FIG. 38) that can be positioned within the wearer's gluteal cleft. The portions of the absorbent structure 321 between the first line of weakness 390*a* and each of the second lines of weakness 390*b*, 390*c* form sloping sidewalls that contact the portions of the buttocks of the wearer that define the gluteal cleft. The portion of the absorbent structure 321 transversely outward from the second lines of weakness 390*b*, 390*c* define flanking portions adapted to contact the buttocks of the wearer remote from the gluteal cleft. As a result, the absorbent structure 321 rests at least partially within the gluteal cleft of the wearer and thereby blocks the flow of body exudates along this potential leakage pathway.

The third through sixth lines of weakness 390*d*-390*g* cooperatively define a relief that inhibits the folding of the absorbent structure 321 within the lower portion 339 thereof from extending within the middle portion 337 to the region of the absorbent structure that directly aligns with the vaginal region of the wearer. In the illustrated embodiment, the third through sixth lines of weakness 390*d*-390*g* facilitate folding of the absorbent article 300 about an axis that is generally parallel to the transverse axis of the article, which inhibits the folding of the absorbent article caused by the first and second lines of weakness from extending beyond the transverse fold facilitated by the third through sixth lines of weakness. When worn, the third through sixth lines of weakness 390*d*-390*g* facilitate the absorbent structure 321 folding transversely of the absorbent structure 321 in the perineum region of the wearer thereby inhibiting the longitudinally extending folds facilitated by the first and second lines of weakness 390*a*-390*c* from extending beyond the gluteal region and into the vaginal region of the wearer. Thus, the absorbent article 300 disclosed herein is contoured to conform to the complex shape of a women's perineum and gluteal regions during use to inhibit leakage and provide a more comfortable article for the wearer while inhibiting portions of the article from penetrating any portion of the wearer's vaginal region.

Figure 39:
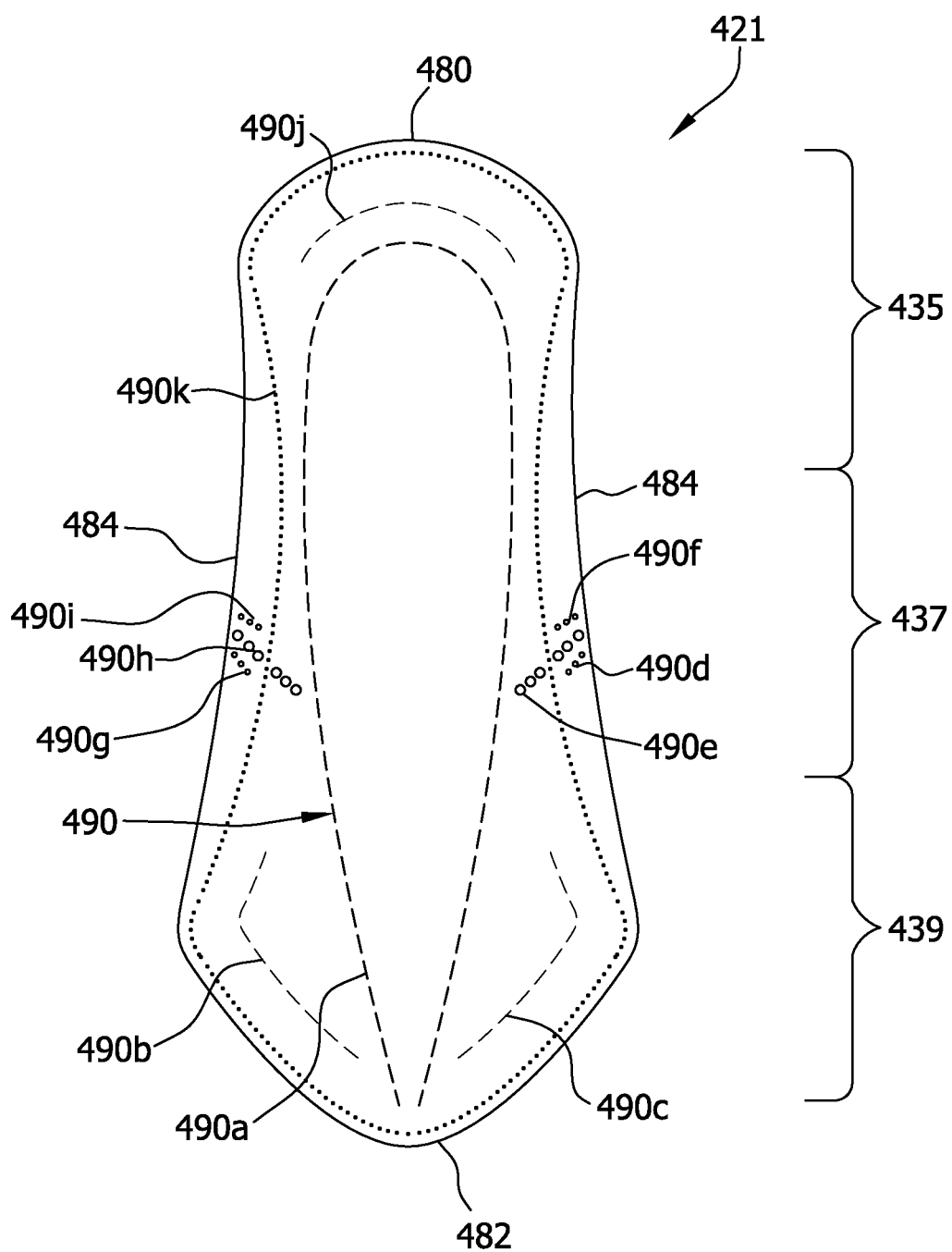
FIGS. 39-47 show top views of embodiments of different absorbent structures.

FIG. 39 illustrates another embodiment of an absorbent structure 421 for use with the shell 314 of FIGS. 30-37 having an upper portion 435, a narrower middle portion 437, and a wider lower portion 439. In this embodiment, the absorbent structure 421 includes lines of weakness, indicated generally at 490, to facilitate folding of the absorbent structure in the middle and lower portions 437, 439 while inhibiting folding of the absorbent structure in the upper portion 435 during wear. In particular, the absorbent structure includes a first line of weakness 490*a* having a generally teardrop-shape. The first line of weakness 490*a* extends through all three portions 435, 437, 439 of the absorbent structure 421. Second lines of weakness 490*b*, 490*c* flank the first line of weakness 490*a* in the lower portion 439 of the absorbent structure 421. The middle portion 437 of the absorbent structure 421 includes three lines of weakness (i.e., a third line of weakness 490*d*, a fourth line of weakness 490*e*, and a fifth line of weakness 490*f*) adjacent a right side edge 484 of the absorbent structure 421, and three lines of weakness (i.e., a sixth line of weakness 490*g*, a seventh line of weakness 490*h*, a eighth line of weakness 490*i*) adjacent a left side edge 484 of the absorbent structure 421 as viewed in FIG. 39. The third through the eighth lines of weakness 490*d*-490*i* extend inward from respective side edge 484 and are angled toward the lower portion 439 of the absorbent structure 421. An arcuate ninth line of weakness 490*j* is located in the upper portion 435 of the absorbent structure and disposed between an upper edge 480 of the absorbent structure and the first line of weakness 490. A tenth line of weakness 490*k* extends along the edge margin about the entire periphery of the absorbent structure 421. In this embodiment, the distance between the tenth line of weakness 490*k* and the peripheral edges (i.e., the side edges 484, the upper edge 480, and a lower edge 482) differs along the length of the tenth line of weakness. In one suitable embodiment, the tenth line of weakness 490*k* is closer to the upper and lower edges 480, 482 than it is to the side edges 484. That is, the distance between the tenth line of weakness 490*k* and the peripheral edge is greater adjacent the side edges 484 as compared to the upper and lower edges 480, 482.

The first and second lines of weakness 490*a*-490*c* allow the absorbent structure 421 to fold generally longitudinally to thereby conform to the gluteal cleft of the wearer. In particular, the first line of weakness 490*a* in the lower portion 439 of the absorbent structure 421 defines a peak that can be positioned within the wearer's gluteal cleft. In this embodiment, the peak is in the form of a plateau that widens as it extends from adjacent the lower edge 482 towards the middle portion 437 of the absorbent structure 421 as a result of portions of the first line of weakness 490a in the lower portion 439 of the absorbent structure 421 diverging as they extend toward to the middle portion. As a result, the absorbent structure 421 rests at least partially within the gluteal cleft of the wearer during use and thereby blocks the flow of body exudates along this potential leakage pathway.

The third through eighth lines of weakness 490d-490i cooperatively define a relief that inhibits the folding of the absorbent structure 421 within the lower portion 439 thereof from extending into its middle portion 437. In the illustrated embodiment, the third through eighth lines of weakness 490d-490i facilitate folding of the absorbent article 400 about an axis that is generally parallel to the transverse axis of the article, which inhibits the folding of the absorbent article caused by the first and second lines of weakness 490d-490i from extending beyond the transverse fold caused by the third through eighth lines of weakness. When worn, the third through eighth lines of weakness 490d-490i facilitate the absorbent structure 421 folding transverse to the absorbent structure 421 in the perineum region of the wearer thereby inhibiting the longitudinally extending folds created by the first and second lines of weakness 490a-490c from extending beyond the gluteal region and into the vaginal region of the wearer. Thus, the absorbent article 400 disclosed herein is contoured to conform to the complex shape of a women's perineum and gluteal regions during use to prevent leakage and provide a more comfortable article for the wearer while inhibiting portions of the article from penetrating any portion of the wearer's vaginal region.

Figure 40:
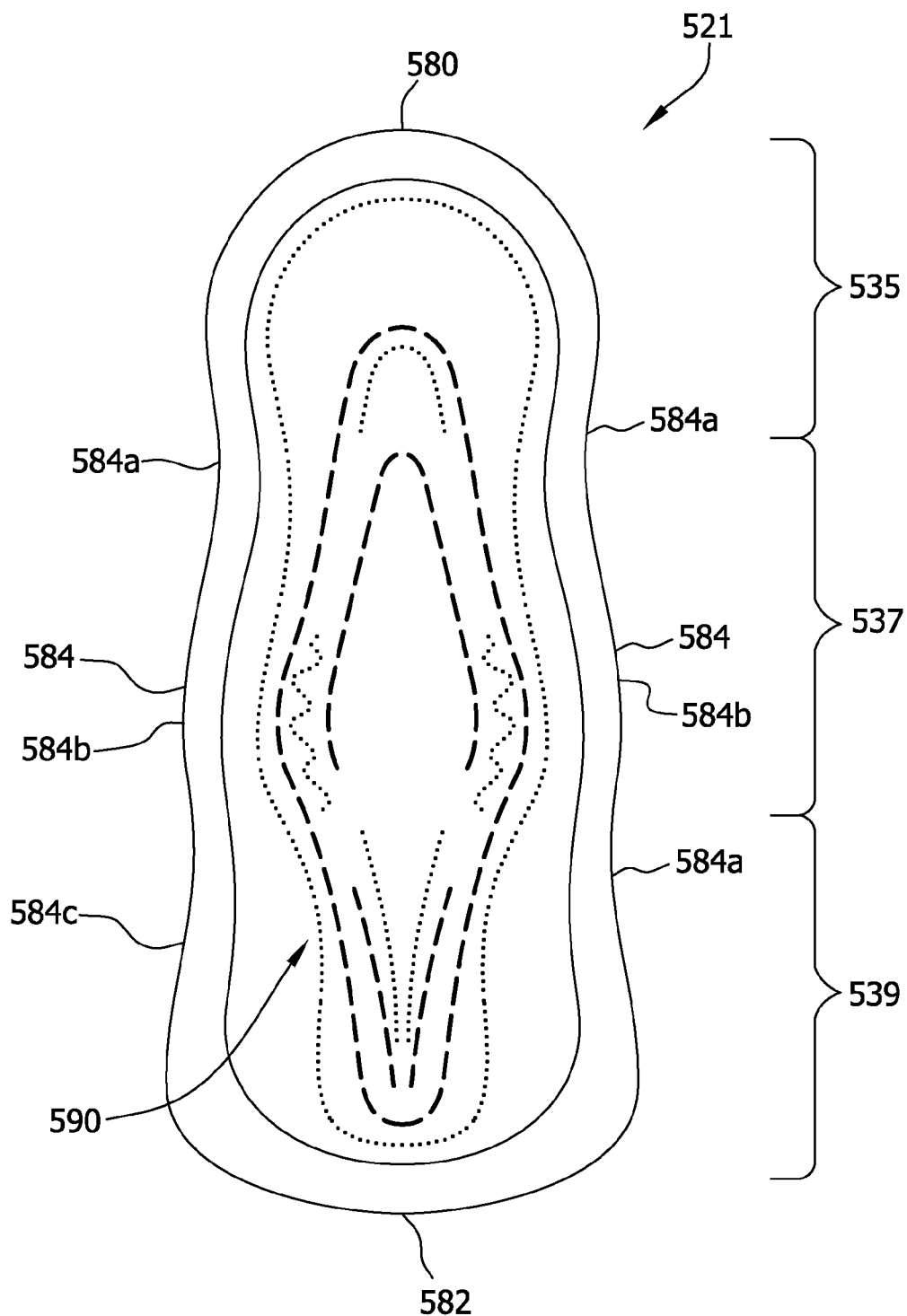

FIG. 40 illustrates another embodiment of an absorbent structure 521 having an upper portion 535, a middle portion 537, and a lower portion 539. The absorbent structure 521 also includes an upper edge 580, a lower edge 582, and side edges 584 extending between and connecting the upper and lower edges. The upper edge 580 of the illustrated absorbent structure 521 is generally semi-circular while the lower edge 582 is generally arcuate. The side edges 584 of this embodiment are wavy along their length having concave portions 584a and convex portions 584b. It is understood that the absorbent structure 521 can have different shapes and configurations without departing from the scope of this invention.

The absorbent structure 521 has lines of weakness, indicated generally at 590, to facilitate folding of the absorbent structure in the middle and lower portions 537, 539 while inhibiting folding of the absorbent structure in the upper portion 535 during wear. The lines of weakness 590 allow the absorbent structure 521 to fold generally longitudinally to thereby conform to the gluteal cleft of the wearer. In particular, the lines of weakness 590 located in the lower portion 539 of the absorbent structure 521 defines a peak that can be positioned within the wearer's gluteal cleft. In this embodiment, the peak is in the form of a plateau that widens as it extends from adjacent the lower edge 582 towards the middle portion 537 of the absorbent structure 521 as a result of the lines of weakness 590 in the lower portion 539 of the absorbent structure 521 diverging as they extend toward to the middle portion. As a result, the absorbent structure 521 rests at least partially within the gluteal cleft of the wearer during use and thereby blocks the flow of body exudates along this potential leakage pathway.

The lines of weakness 590 define a relief that inhibits the folding of the absorbent structure 521 within the lower portion 539 thereof from extending into its middle portion 537. In the illustrated embodiment, the relief is created by some of the lines of weakness 590 located in the lower portion of the absorbent structure 521 terminating before they reach the middle portion 537 and by some of the lines of weakness 590 located in the middle portion 537 have a wave pattern. The relief inhibits the longitudinal folding of the absorbent structure in its lower portion 539 from extending into the middle portion 537. When worn, the lines of weakness 590 facilitates the absorbent structure 521 folding transverse to the absorbent structure 521 in the perineum region of the wearer thereby inhibiting the longitudinally extending folds created by the lines of weakness 590 in the lower portion 539 from extending beyond the gluteal region and into the vaginal region of the wearer. Thus, the absorbent structure 521 disclosed herein is contoured to conform to the complex shape of a women's perineum and gluteal regions during use to prevent leakage and provide a more comfortable article for the wearer while inhibiting portions of the structure from penetrating any portion of the wearer's vaginal region.

Figure 41:
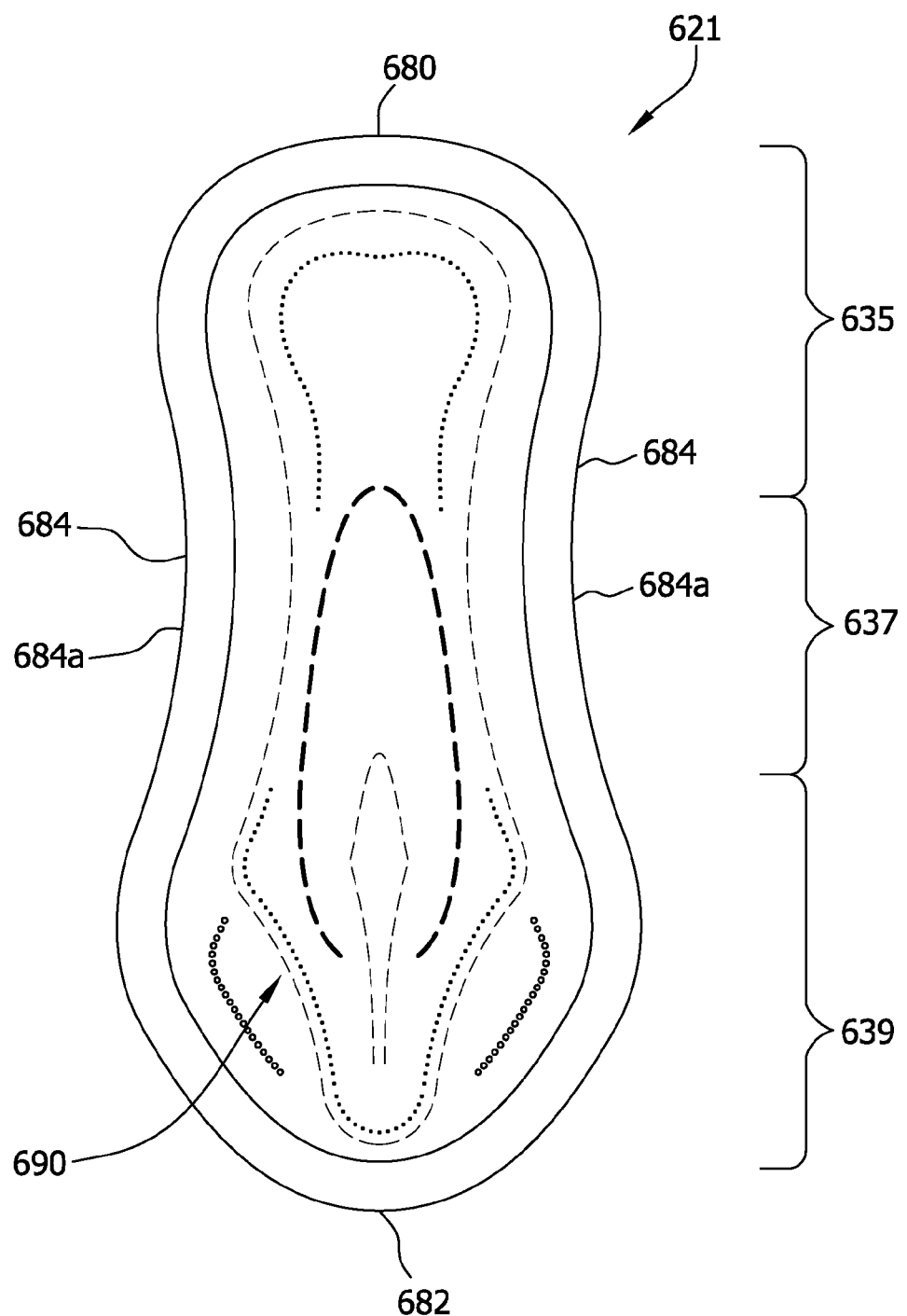

FIG. 41 illustrates another embodiment of an absorbent structure 621 having an upper portion 635, a narrower middle portion 637, and a wider lower portion 639. The absorbent structure 621 also includes an upper edge 680, a lower edge 682, and side edges 684 extending between and connecting the upper and lower edges. The upper edge 680 of the illustrated absorbent structure 621 is generally arcuate while the lower edge 682 is generally semi-circular. The side edges 684 of this embodiment have concave central portions 684a for placement between the respective upper thighs of the wearer. It is understood that the absorbent structure 621 can have different shapes and configurations without departing from the scope of this invention.

The absorbent structure 621 has lines of weakness, indicated generally at 690, to facilitate folding of the absorbent structure in the middle and lower portions 637, 639 while inhibiting folding of the absorbent structure in the upper portion 635 during wear. The lines of weakness 690 allow the absorbent structure 621 to fold generally longitudinally to thereby conform to the gluteal cleft of the wearer. In particular, the lines of weakness 690 located in the lower portion 639 of the absorbent structure 621 defines a peak that can be positioned within the wearer's gluteal cleft. That is, the absorbent structure 621 rests at least partially within the gluteal cleft of the wearer during use and thereby blocks the flow of body exudates along this potential leakage pathway.

The lines of weakness 690 define a relief that inhibits the longitudinal folding of the absorbent article 621 within the lower portion 639 thereof from extending into its middle portion 637. In the illustrated embodiment, the relief is created by some of the lines of weakness 690 located in the lower portion of the absorbent structure 621 terminating before they reach the middle portion 637 and by some of the lines of weakness 690 located in the lower portion 637 being crooked. More particularly, some of the lines of weakness 690 have arcuate portions that a generally aligned with each other to define a generally transverse axis about with the absorbent structure 621 can fold. The relief inhibits the longitudinal folding of the absorbent structure 621 in its lower portion 639 from extending into the middle portion 637. When worn, the lines of weakness 690 facilitates the absorbent structure 621 folding transverse to the absorbent structure 621 in the perineum region of the wearer thereby inhibiting the longitudinally extending folds created by the lines of weakness 690 in the lower portion 639 from extending beyond the gluteal region and into the vaginal region of the wearer. Thus, the absorbent structure 621 disclosed herein is contoured to conform to the complex shape of a women's perineum and gluteal regions during use to prevent leakage and provide a more comfortable article for the wearer while inhibiting portions of the structure from penetrating any portion of the wearer's vaginal region.

Figure 42:
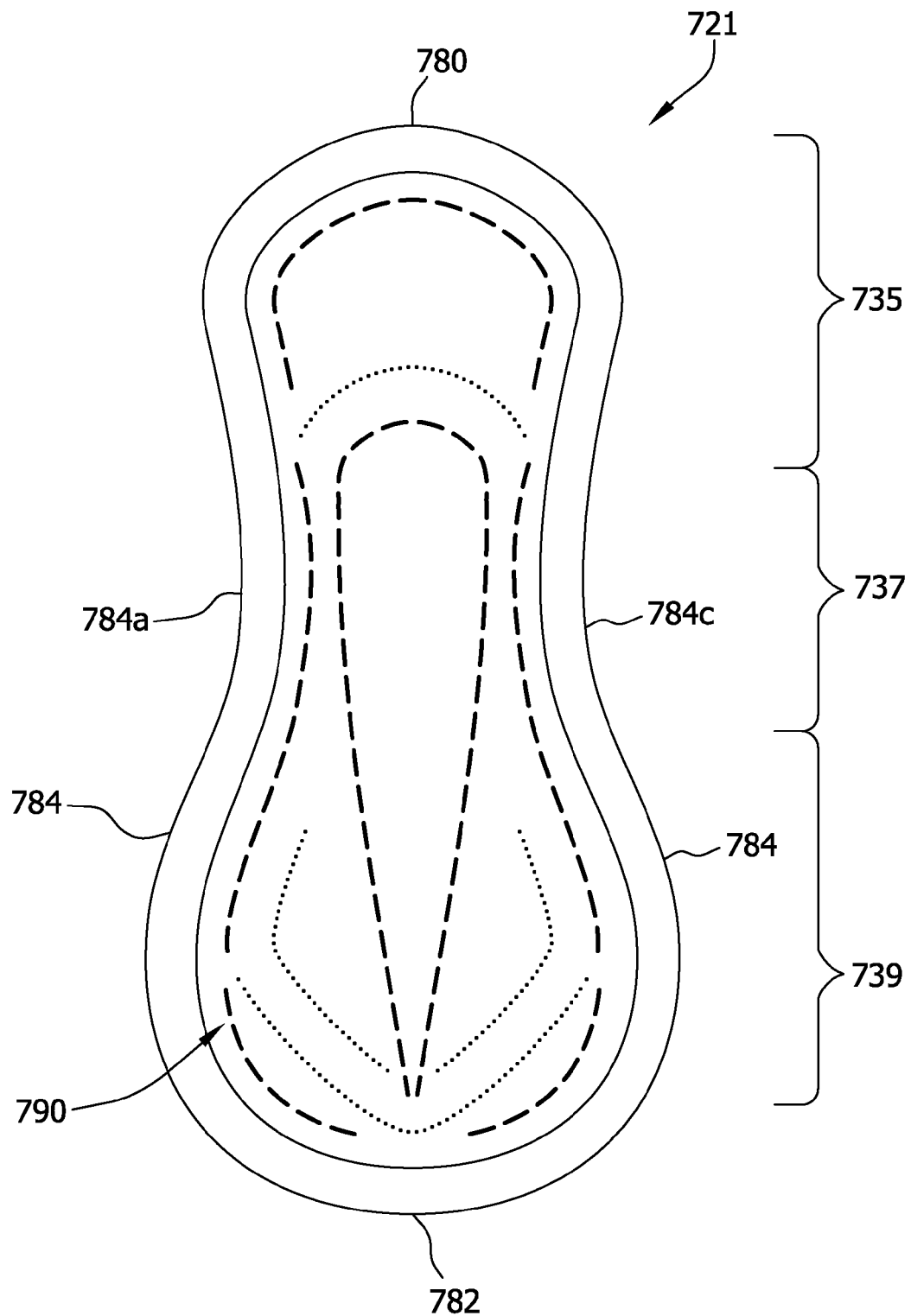

FIG. 42 illustrates another embodiment of an absorbent structure 721 having an upper portion 735, a narrower middle portion 737, and a wider lower portion 739. The absorbent structure 721 also includes an upper edge 780, a lower edge 782, and side edges 784 extending between and connecting the upper and lower edges. The upper and lower edges 780, 782 of the illustrated absorbent structure 721 are generally semi-circular. The side edges 784 of this embodiment have concave central portions 784*a* for receiving the respective upper thighs of the wearer. It is understood that the absorbent structure 721 can have different shapes and configurations without departing from the scope of this invention.

The absorbent structure 721 has lines of weakness, indicated generally at 790, to facilitate folding of the absorbent structure in the middle and lower portions 737, 739 while inhibiting folding of the absorbent structure in the upper portion 735 during wear. The lines of weakness 790 allow the absorbent structure 721 to fold generally longitudinally to thereby conform to the gluteal cleft of the wearer. In particular, the lines of weakness 790 located in the lower portion 739 of the absorbent structure 721 defines a peak that can be positioned within the wearer's gluteal cleft. In this embodiment, the peak is in the form of a plateau that widens as it extends from adjacent the lower edge 782 towards the middle portion 737 of the absorbent structure 721 as a result of the lines of weakness 790 in the lower portion 739 of the absorbent structure 721 diverging as they extend toward to the middle portion. As a result, the absorbent structure 721 rests at least partially within the gluteal cleft of the wearer during use and thereby blocks the flow of body exudates along this potential leakage pathway.

The lines of weakness 790 define a relief that inhibits the folding of the absorbent article 721 within the lower portion 739 thereof from extending into its middle portion 737. In the illustrated embodiment, the relief is created by some of the lines of weakness 790 located in the lower portion of the absorbent structure 721 terminating before they reach the middle portion 737 and by some of the lines of weakness 790 located in the middle portion 537 have aligned accurate portions. The relief inhibits the longitudinal folding of the absorbent structure in its lower portion 739 from extending into the middle portion 737. When worn, the lines of weakness 790 facilitates the absorbent structure 721 folding transverse to the absorbent structure 721 in the perineum region of the wearer thereby inhibiting the longitudinally extending folds created by the lines of weakness 790 in the lower portion 739 from extending beyond the gluteal region and into the vaginal region of the wearer. Thus, the absorbent structure 721 disclosed herein is contoured to conform to the complex shape of a women's perineum and gluteal regions during use to prevent leakage and provide a more comfortable article for the wearer while inhibiting portions of the structure from penetrating any portion of the wearer's vaginal region.

Figure 43:
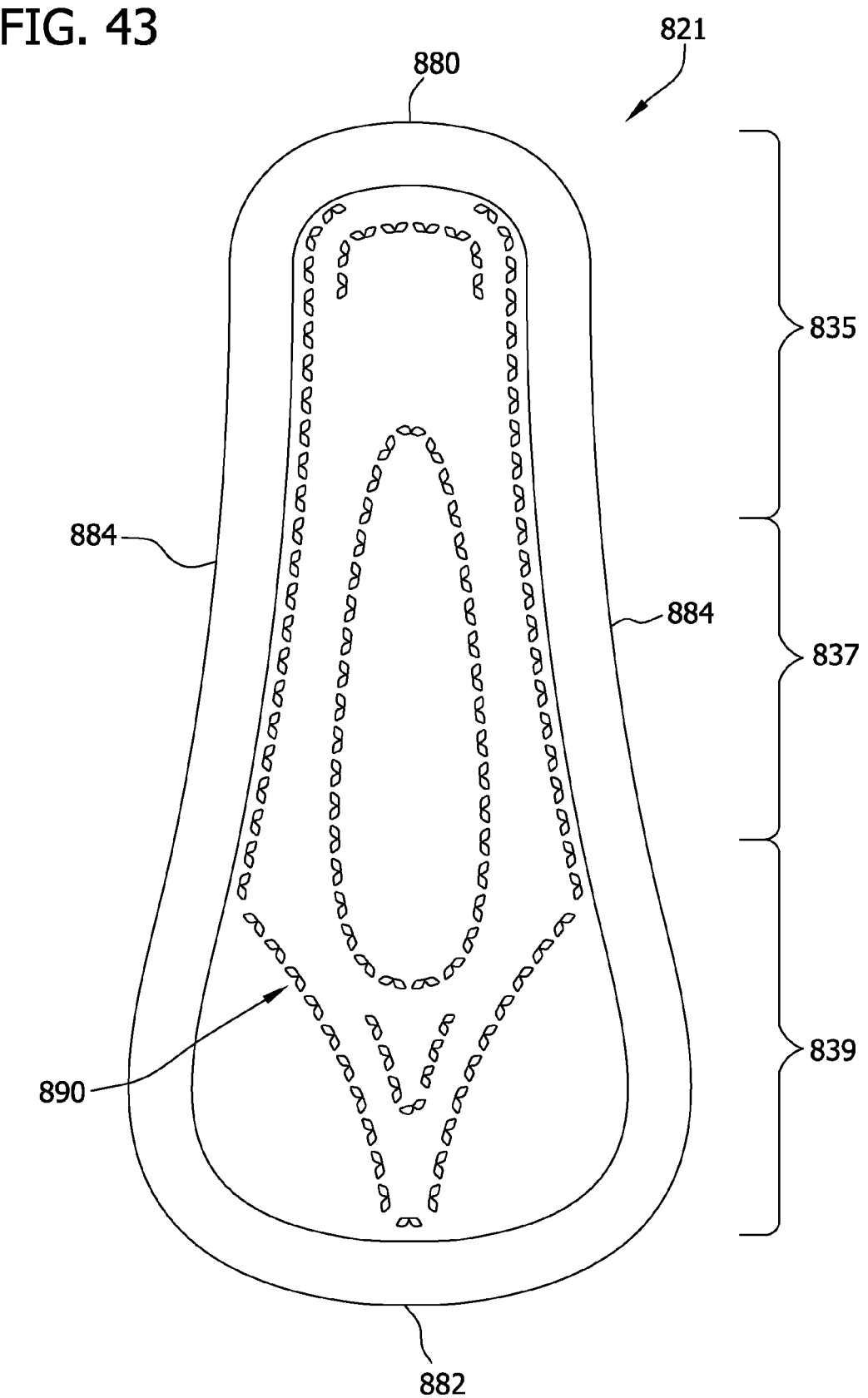

FIG. 43 illustrates another embodiment of an absorbent structure 821 having an upper portion 835, a tapered middle portion 837, and a wider lower portion 839. The absorbent structure 821 also includes an upper edge 880, a lower edge 882, and side edges 884 extending between and connecting the upper and lower edges. The upper and lower edges 880, 882 of the illustrated absorbent structure 821 are generally arcuate. The side edges 884 of this embodiment are generally straight and slope inward toward each other as they extend from the lower portion 839 toward the upper portion 835. As a result, the side edges 884 are closer together in the upper portion 835 than they are in the lower portion 839. It is understood that the absorbent structure 821 can have different shapes and configurations without departing from the scope of this invention. The absorbent structure 821 has lines of weakness, indicated generally at 890, to facilitate longitudinal folding of the absorbent structure in its lower portions 837 while inhibiting folding of the absorbent structure in the upper portion 835 during wear by forming a relief in or near the middle portion of the absorbent article. The relief inhibits the longitudinal folding of the absorbent structure 821 from extending beyond its lower portion 839. In this embodiment, each of the lines of weakness 890 comprises a plurality of leafs. In other words, the dashes forming the lines of weakness are in the form of leafs, which are embossed (or otherwise created) on the absorbent structure 821. It is understood that the dashes can be formed in other suitable patterns besides leafs without departing from the scope of this invention.

Figure 44:
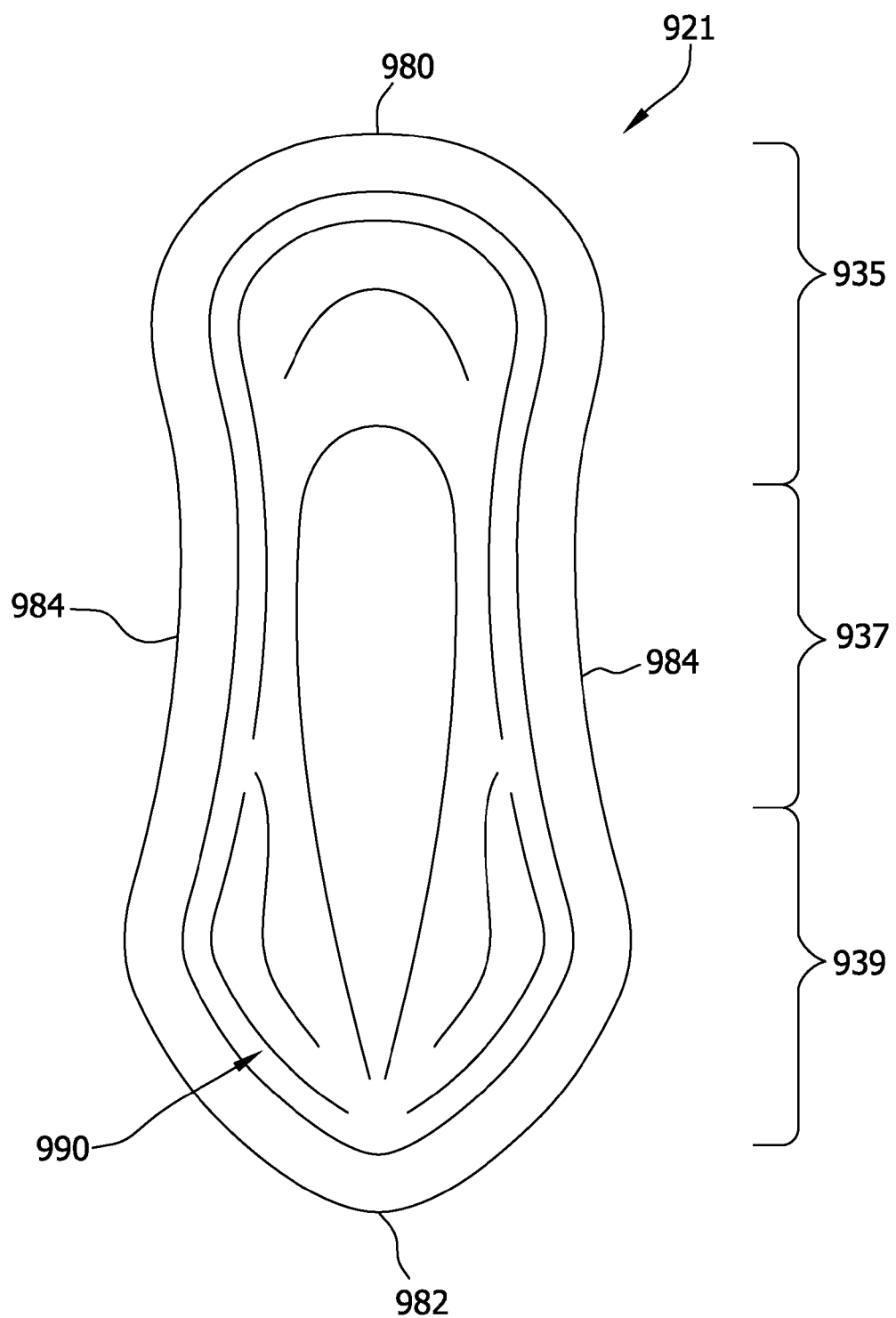

FIG. 44 illustrates another embodiment of an absorbent structure 921 having an upper portion 935, a middle portion 937, and a lower portion 939. The absorbent structure 921 also includes an upper edge 980, a lower edge 982, and side edges 984 extending between and connecting the upper and lower edges. The upper edge 980 of the illustrated absorbent structure 921 is generally arcuate and the lower edge 982 is generally V-shaped. The side edges 984 of this embodiment are slightly concaved along their lengths for placement between the upper thighs of the wearer. It is understood that the absorbent structure 921 can have different shapes and configurations without departing from the scope of this invention. The absorbent structure 921 has lines of weakness, indicated generally at 990, to facilitate longitudinal folding of the absorbent structure 921 in its lower portion 937 while inhibiting folding of the absorbent structure in its upper portion 935 during wear by creating a relief. The relief is formed by some of the lines of weakness 990 terminating in the middle portion 937 adjacent the lower portion 939 and by some of the lines of weakness 990 being formed with aligned arcuate portions that define a transverse axis about which the absorbent article can fold. In this embodiment, each of the lines of weakness 890 comprises a solid embossed (or otherwise formed) line.

Figure 45:
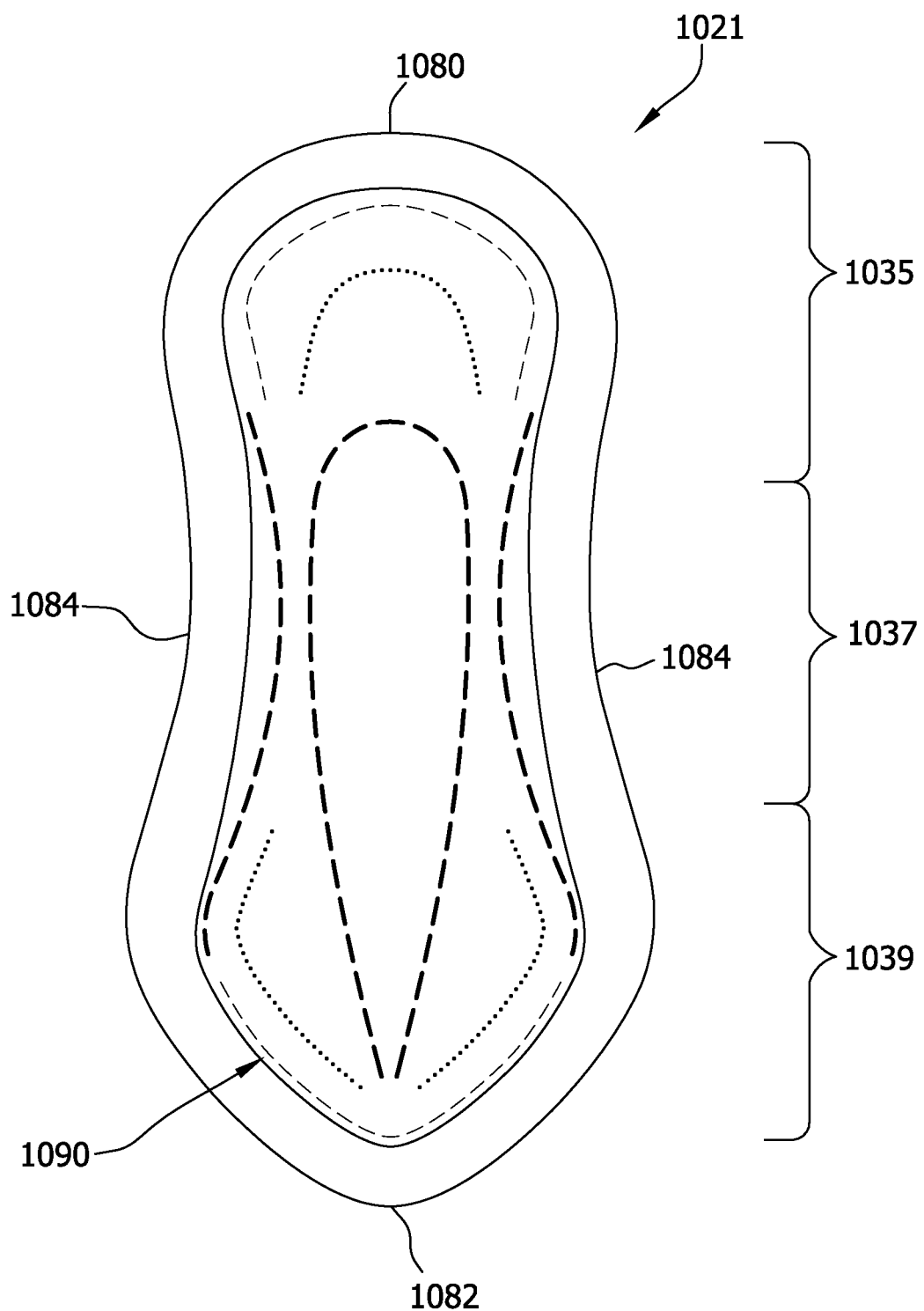

FIG. 45 illustrates another embodiment of an absorbent structure 1021 having an upper portion 1035, a middle portion 1037, and a lower portion 1039. The absorbent structure 1021 also includes an upper edge 1080, a lower edge 1082, and side edges 1084 extending between and connecting the upper and lower edges. The upper edge 1080 of the illustrated absorbent structure 1021 is generally arcuate and the lower edge 1082 is generally V-shaped. The side edges 1084 of this embodiment are slightly concaved along their lengths for receiving the upper thighs of the wearer. It is understood that the absorbent structure 1021 can have different shapes and configurations without departing from the scope of this invention. The absorbent structure 1021 has lines of weakness, indicated generally at 1090, to facilitate longitudinal folding of the absorbent structure in its lower portions 1037 and to define a relief for inhibiting longitudinal folding of the absorbent structure beyond the lower portion during wear.

Figure 46:
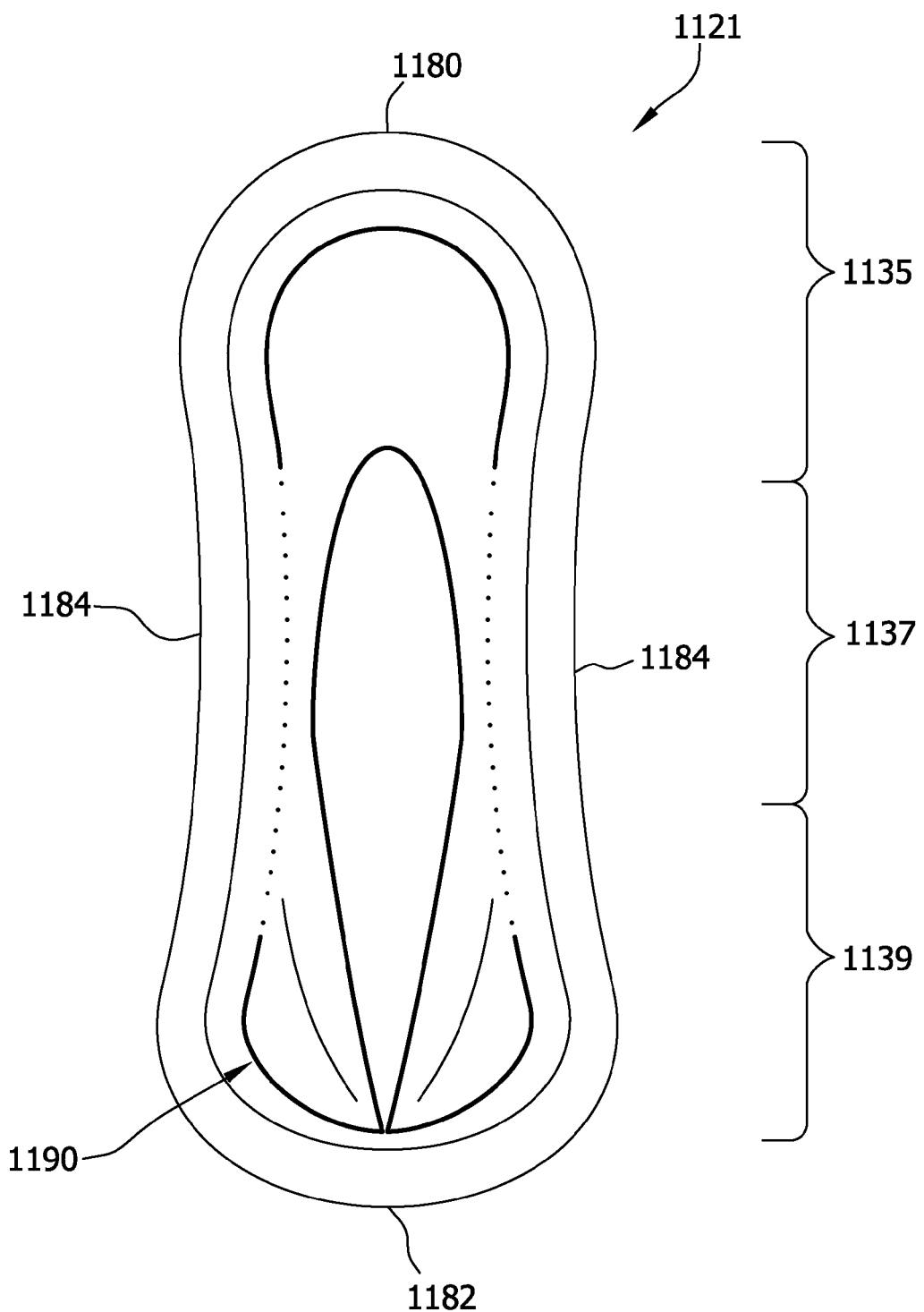

FIG. 46 illustrates another embodiment of an absorbent structure 1121 having an upper portion 1135, a middle portion 1137, and a lower portion 1139. The absorbent structure 1121 also includes an upper edge 1180, a lower edge 1182, and side edges 1184 extending between and connecting the upper and lower edges. The upper and lower edges 1180, 1182 of the illustrated absorbent structure 1121 are generally arcuate. The side edges 1184 of this embodiment are slightly concaved along their lengths for receiving the upper thighs of the wearer. It is understood that the absorbent structure 1121 can have different shapes and configurations without departing from the scope of this invention. The absorbent structure 1121 has lines of weakness, indicated generally at 1190, to facilitate longitudinal folding of the absorbent structure in its lower portions 1137 and to define a relief for inhibiting longitudinal folding of the absorbent structure beyond the lower portion during wear. In this embodiment, the lines of weakness 1190 comprises a combination of solid embossed (or otherwise formed) line and doted lines.

Figure 47:
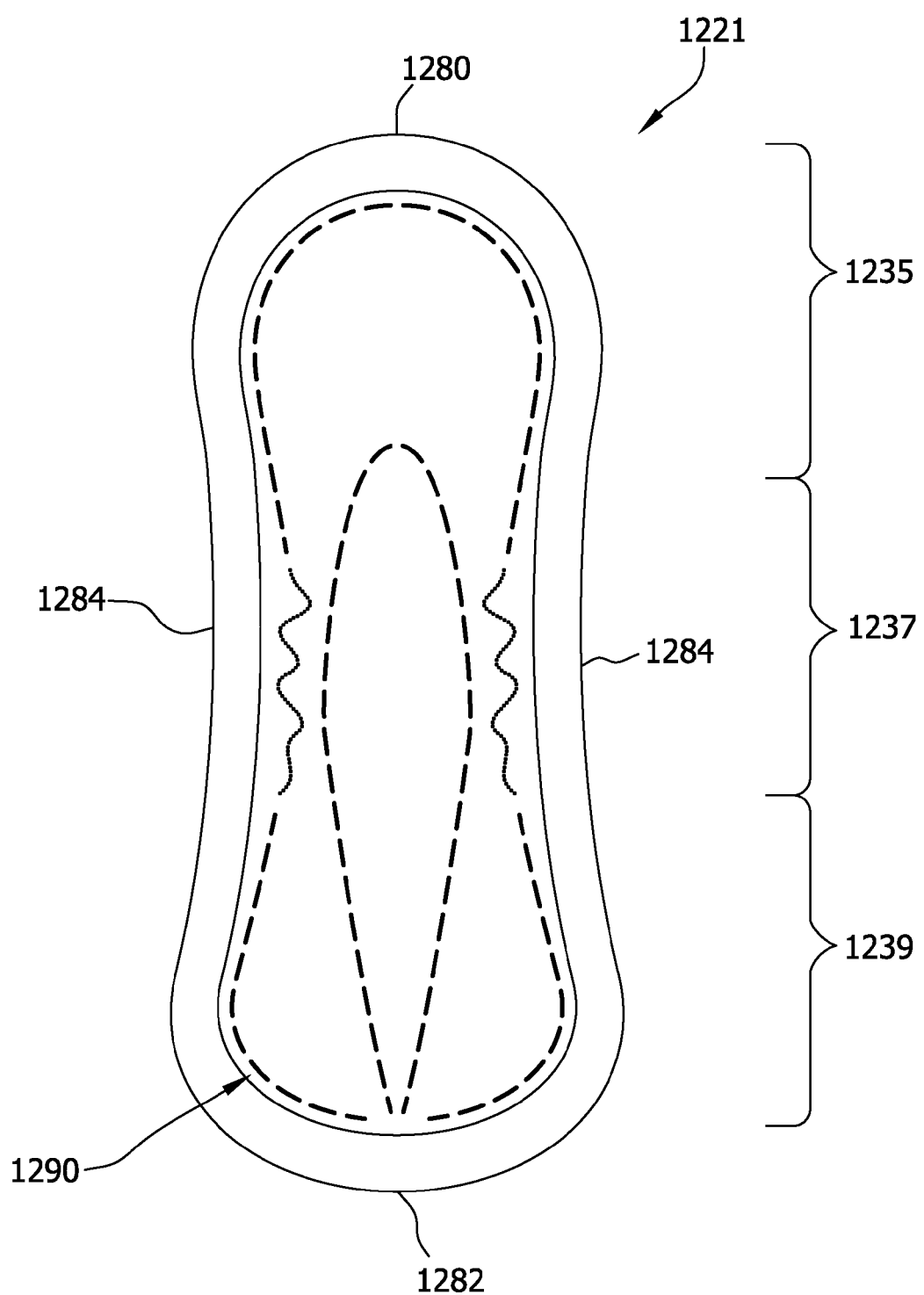
Figure 48:
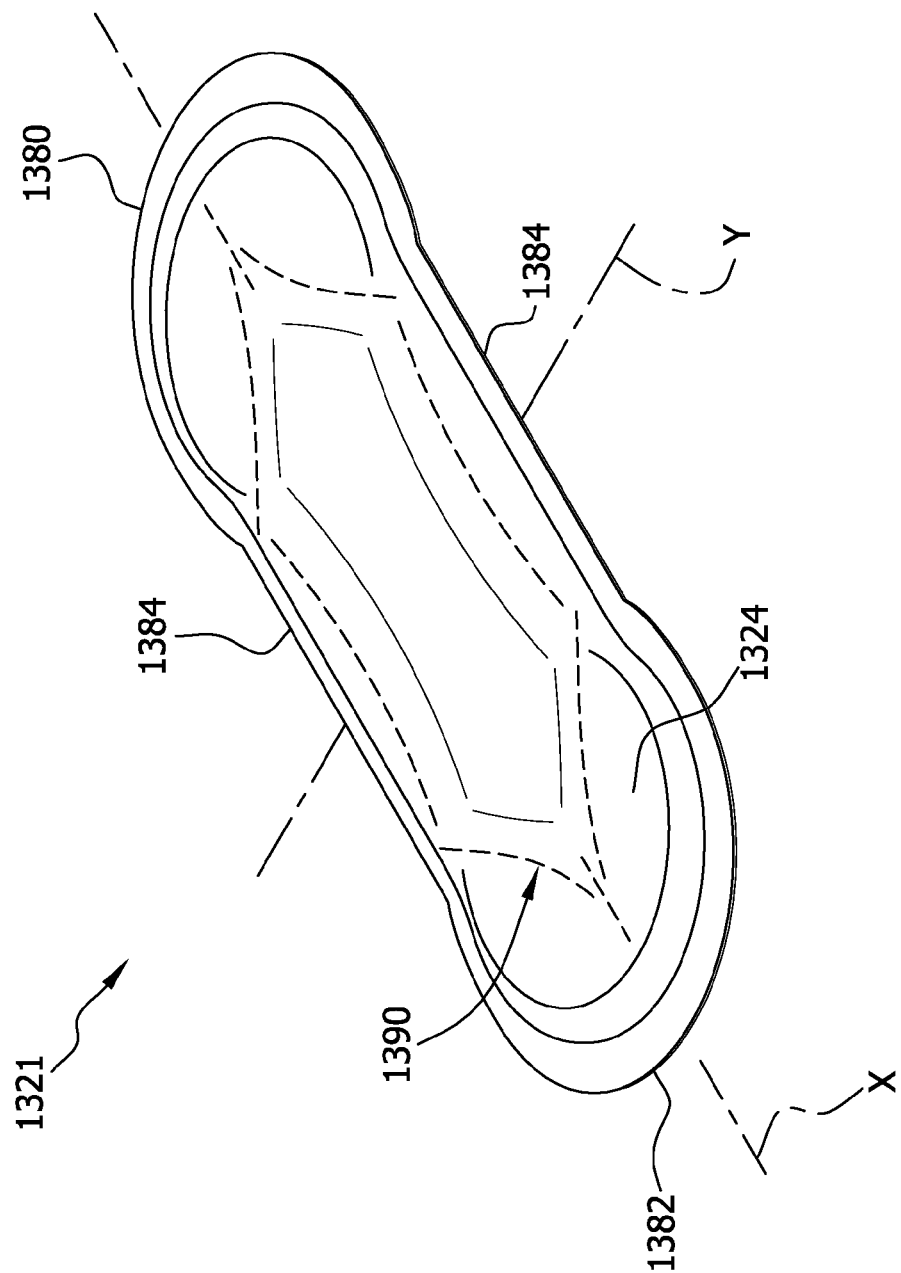
FIG. 48 shows a perspective view of another embodiment of an absorbent structure.

FIG. 47 illustrates another embodiment of an absorbent structure 1221 having an upper portion 1235, a middle portion 1237, and a lower portion 1239. The absorbent structure 1221 also includes an upper edge 1280, a lower edge 1282, and side edges 1284 extending between and connecting the upper and lower edges. The upper and lower edges 1280, 1282 of the illustrated absorbent structure 1221 are generally arcuate. The side edges 1284 of this embodiment are slightly concaved along their lengths for placement between the upper thighs of the wearer. It is understood that the absorbent structure 1221 can have different shapes and configurations without departing from the scope of this invention. The absorbent structure 1221 has lines of weakness, indicated generally at 1290, to facilitate longitudinal folding of the absorbent structure in its lower portions 1237 and to define a relief for inhibiting longitudinal folding of the absorbent structure beyond the lower portion during wear.

Each of the absorbent structures shown in FIGS. 37 and 39-47 is configured to be used in combination with a shell, such as the shell 314 of FIG. 36. It is understood, however, that the absorbent structures can be used independent of the shell without departing from some aspects of this invention.

Figure 49:
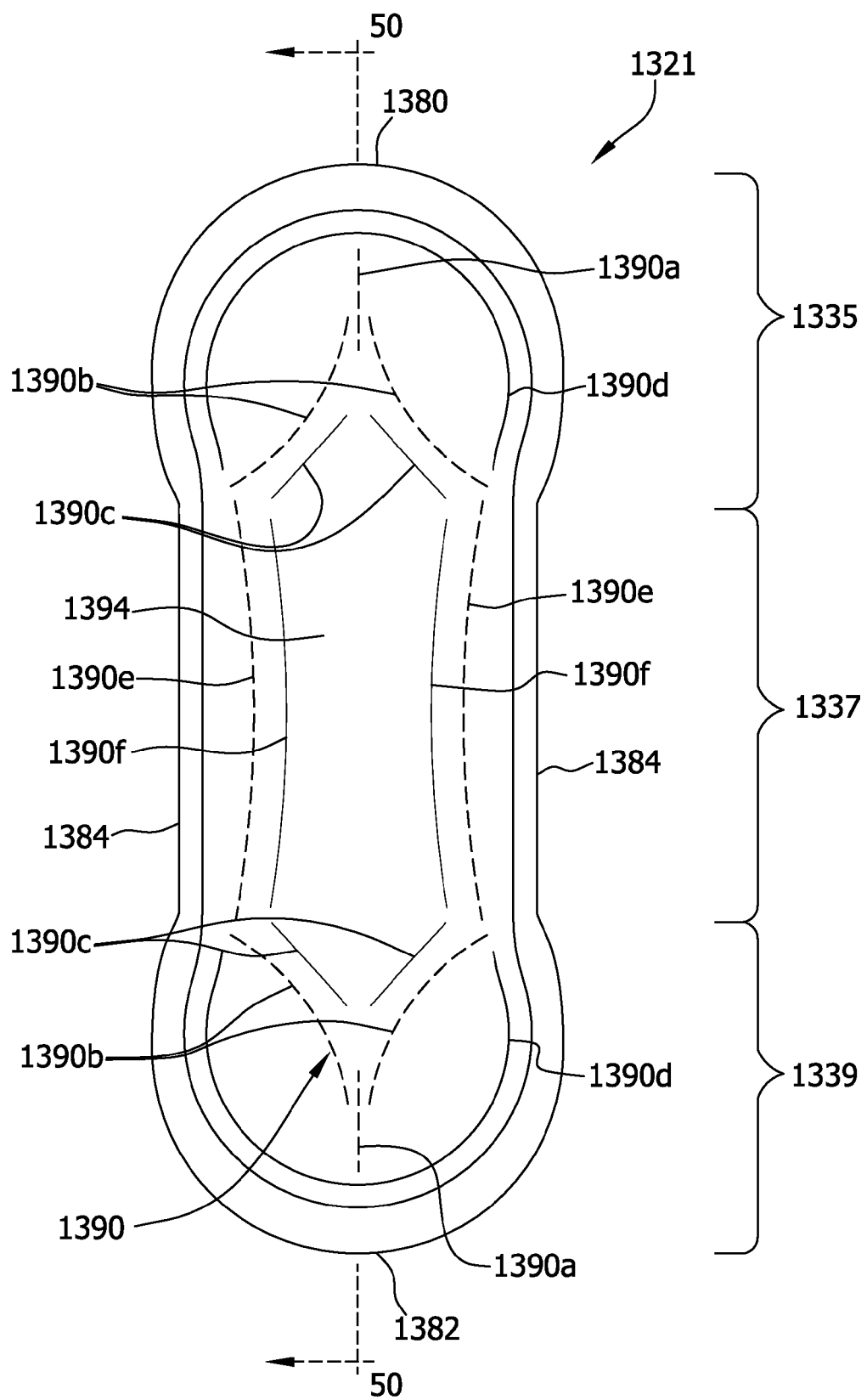
FIG. 49 shows a top view of the absorbent structure.
Figure 50:
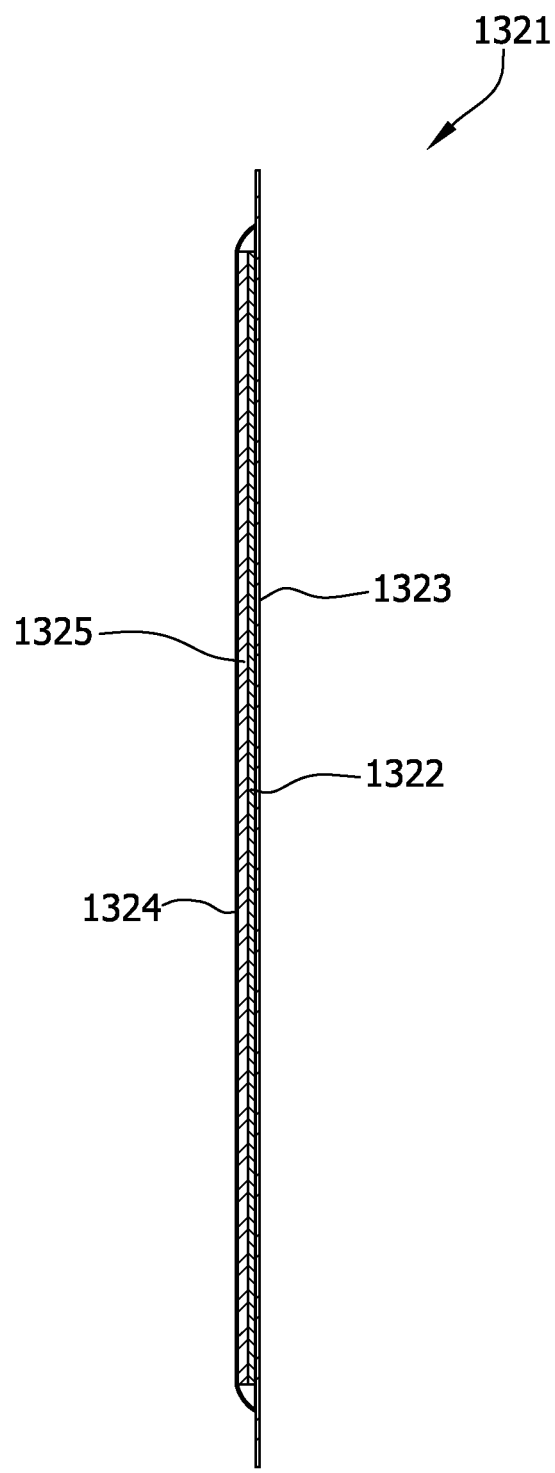
FIG. 50 shows a side cut-away view of the absorbent structure taken along line 50-50 of FIG. 49.

FIGS. 48-51 illustrate an embodiment of an absorbent structure 1321 to be used independently (i.e., without a shell). The absorbent structure 1321 has a longitudinal axis X and a transverse axis Y and can comprise a single layer structure (not shown) or a multiple layer structure. The illustrated absorbent structure 1321, for example, is a multiple layer structure comprising an absorbent core 1322, an intake layer 1325, a top sheet 1324, and a liquid impermeable backsheet 1323 (FIG. 50). As seen in FIG. 49, the illustrated absorbent structure 1321 has an upper portion 1335, a narrower middle portion 1337, and a lower portion 1339. The absorbent structure 1321 has generally semi-circular upper and lower edges 1380, 1382, and opposite, generally straight side edges 1384 extending between the upper and lower edges. The upper edge 1380, the lower edge 1382, and the side edges 1384 collectively define a periphery of the absorbent structure 1321.

With reference still to FIG. 49, the absorbent structure 1321 includes lines of weakness, indicated generally at 1390, to facilitate folding of the absorbent structure in the upper and lower portions 1335, 1339. In the illustrated embodiment, the lines of weakness 1390 are generally symmetric about the transverse axis Y of the absorbent structure 1321. As a result, the absorbent structure 1321 is adapted for use in the same manner regardless of the longitudinal orientation thereof during use. That is, either the upper or lower edge 1380, 1382 can be placed adjacent the wearer's gluteal region during use. More specifically, the lines of weakness 1390 are adapted to facilitate folding of the absorbent structure 1321 during use such that a portion of the absorbent structure is received in the gluteal cleft of the wearer. The gluteal cleft has been found to provide a passageway for liquid exudates to leak. Placement of a portion of the absorbent structure 1321 within the gluteal cleft blocks this potential passageway and thereby inhibits leakage of body exudates.

In particular, each of the upper and lower portions 1335, 1339 of the absorbent structure 1321 includes a first line of weakness 1390a positioned generally along the longitudinal axis of the absorbent structure and two second lines of weakness 1390b spaced from and flanking the first line of weakness. The second lines of weakness 1390b in each of the upper and lower portions 1335, 1339 diverge as they extend away from the respective first line of weakness 1390a. Third lines of weakness 1390c extend generally adjacent to and are spaced inward (i.e., toward the central region 1394) from each of the second lines of weakness. Fourth, semi-circular lines of weakness 1390d are located generally adjacent the upper and lower edges 1380, 1382 of the absorbent structure 1321.

The middle portion 1337 of the absorbent structure 1321 includes a pair of fifth lines of weakness 1390e and a pair of sixth lines of weakness 1390f extending longitudinally along the absorbent structure. One of the fifth lines of weakness 1390e and one of the sixth lines of weakness 1390f flank each side of the central region 1394 of the absorbent structure 1321.

In the illustrated embodiment, some of the lines of weakness 1390 are formed by embossing dashed lines (1390a, 1390b, 1390e) or solid lines (1390c, 1390d, 1390f) in the absorbent core 1322, the intake layer 1325, and the top sheet 1324. The size and shape of the individual dashes that define the lines of weakness 1390 can be varied to alter the characteristics (i.e., resistance to folding) and appearance of the line of weakness. The spacing between the individual dashes can also be varied for the same reasons. It is understood that the lines of weakness 1390 can be formed in other ways, such as, cutting, perforating, bonding, mechanical thinning, or other processes as are known in the art one or more layer of the absorbent structure.

Figure 51:
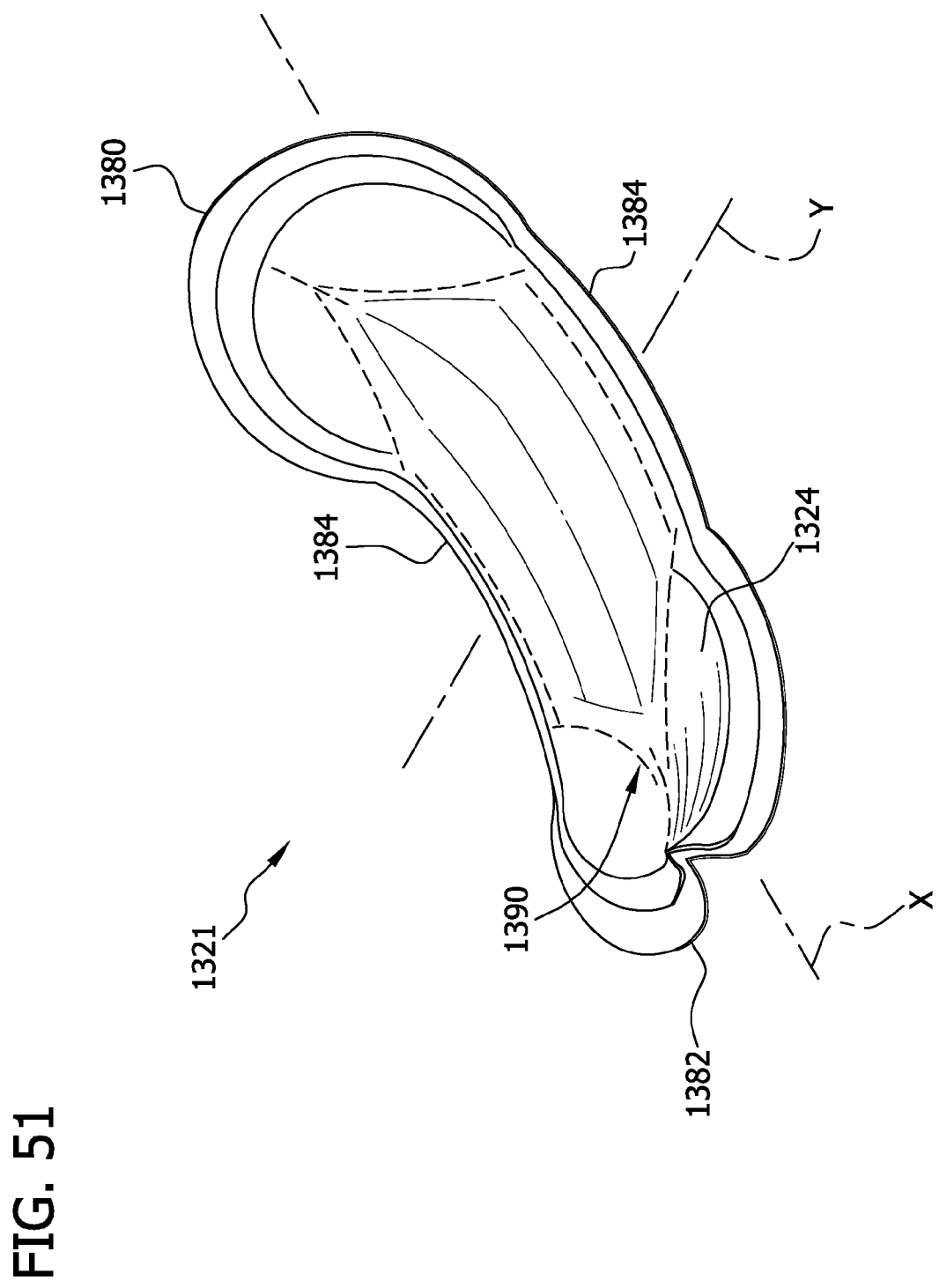
FIG. 51 shows a perspective view of the absorbent structure of FIG. 48 in a wear configuration.

A wear configuration of the absorbent structure 1321 is illustrated in FIG. 51. As mentioned previously, the illustrated absorbent structure 1321 is generally symmetric so that either the upper portion 1335 or the lower portion 1339 can be disposed adjacent the gluteal region of the wearer. For purposes of this description, it is assumed that the lower portion 1339 of the absorbent structure 1321 is placed adjacent the gluteal region of the wearer but it is understood that the upper portion 1335 can be placed adjacent the gluteal region.

In use, the upper portion 1335 and the middle portion 1337 of the absorbent structure 1321 are supported in close proximity to the vaginal region and perineum region of the wearer by the wearer's underwear or undergarment (not shown). Suitable garment adhesive (not shown) may be applied to the backsheet 1323 for adhering the absorbent structure to the wearer's undergarment. The fifth and sixth lines of weakness 1390e, 1390f allow the absorbent structure 1321 to compress between the upper thighs of the wearer while inhibiting the central region 1394 from folding, bending, or otherwise deforming and entering any cleft, fold, cavity, or opening in the vaginal region of the wearer. That is, the fifth and sixth lines of weakness 1390e, 1390f facilitate maintaining the absorbent article 300 exterior the vaginal region of the female wearer.

The termination of the fifth and sixth lines of weakness 1390f, 1390e adjacent the termination of the second and third lines of weakness 1390b, 1390c respectively enables the absorbent article 1321 to fold about a transverse axis that is generally parallel to the transverse axis Y of the structure. This facilitates folding of the absorbent structure 1321 between the perineum region and the gluteal region of the wearer. The first through fourth lines of weakness 1390a-1390d allow the absorbent structure to conform to the gluteal cleft of the wearer. In particular, the first line of weakness 1390a in the lower portion 1339 of the absorbent structure 1321 defines a peak that can be positioned within the gluteal cleft. The portions of the absorbent structure adjacent the first line of weakness 1390a define sloping sidewalls that contact the portions of the buttocks that define and are adjacent to the gluteal cleft. The absorbent structure 1321 seats within the gluteal cleft of the wearer and thereby blocks the flow of body exudates along this potential leakage pathway.

The second through sixth lines of weakness 1390b-1390f have respective ends that terminate generally adjacent the transition between the lower and middle portions 1339, 1337 of the absorbent structure 1321. The terminated ends of each of these lines of weakness 1390b-1390f collectively define a relief that inhibits longitudinal folding of the absorbent article 1321 beyond the lower portion 1339 of the absorbent structure. In the illustrated embodiment, the second through sixth lines of weakness 1390b-1390f facilitate folding of the absorbent structure 1321 about an axis that is generally parallel to the transverse axis of the article, which inhibits the folding of the absorbent article caused by the first line of weakness 1390a from extending beyond the transverse fold caused by the second through sixth lines of weakness. When worn, the second through sixth lines of weakness 1390b-1390f facilitates the absorbent structure 1321 folding transversely in the perineum region of the wearer thereby inhibiting the longitudinally extending folds created by the first line of weakness 1390a from extending beyond the gluteal region and into the perineum or vaginal region of the wearer. Thus, the absorbent structure 1321 is constructed to conform to the complex shape of a woman's perineum and gluteal regions during use to prevent leakage and provide a more comfortable article for the wearer while inhibiting the absorbent structure 1321 from riding up into portions of the wearer's vaginal region.

Figure 52:
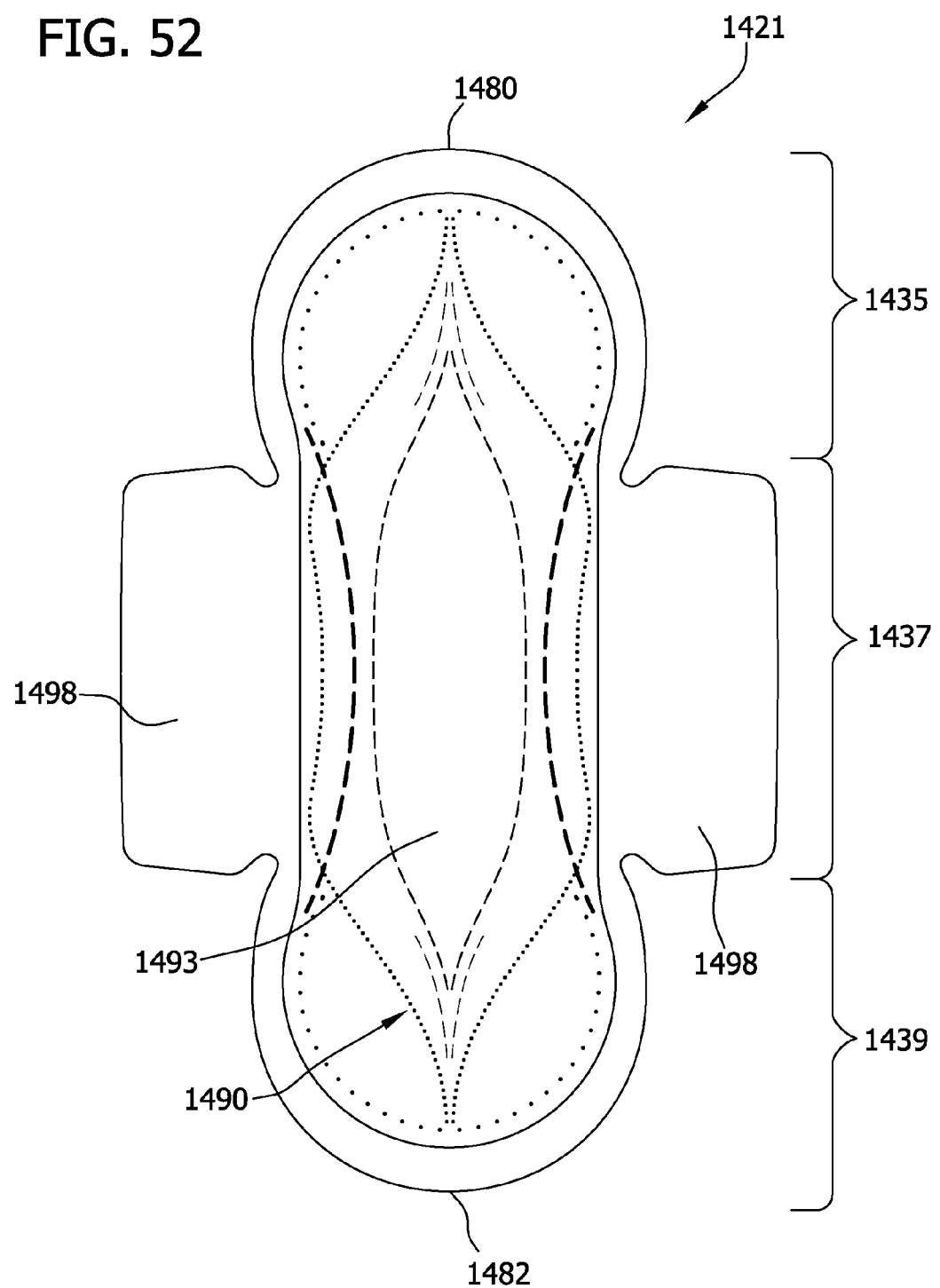
FIG. 52 shows a top view of an embodiment of an absorbent structure having wings.

FIG. 52 illustrates another embodiment of an absorbent structure 1421 having an upper portion 1435, a middle portion 1437, and a lower portion 1439. The absorbent structure 1421 also includes generally semi-circular upper and lower edges 1480, 1482. The middle portion 1437 of the absorbent structure 1421 includes a pair of opposed wings 1498 extending outward from the structure and that can be wrapped and secured around the undergarment of the wearer to help hold the structure in place. The wings 1498 can include a garment adhesive for adhering the wings to the wearer's undergarment. The absorbent structure 1421 has lines of weakness, indicated generally at 1490, to facilitate folding of the absorbent structure in one of the lower or upper portions 1437, 1439 and to define a relief for inhibiting folding of the absorbent structure in at least a central region 1493 of the middle portion 1437 during wear.

Figure 53:
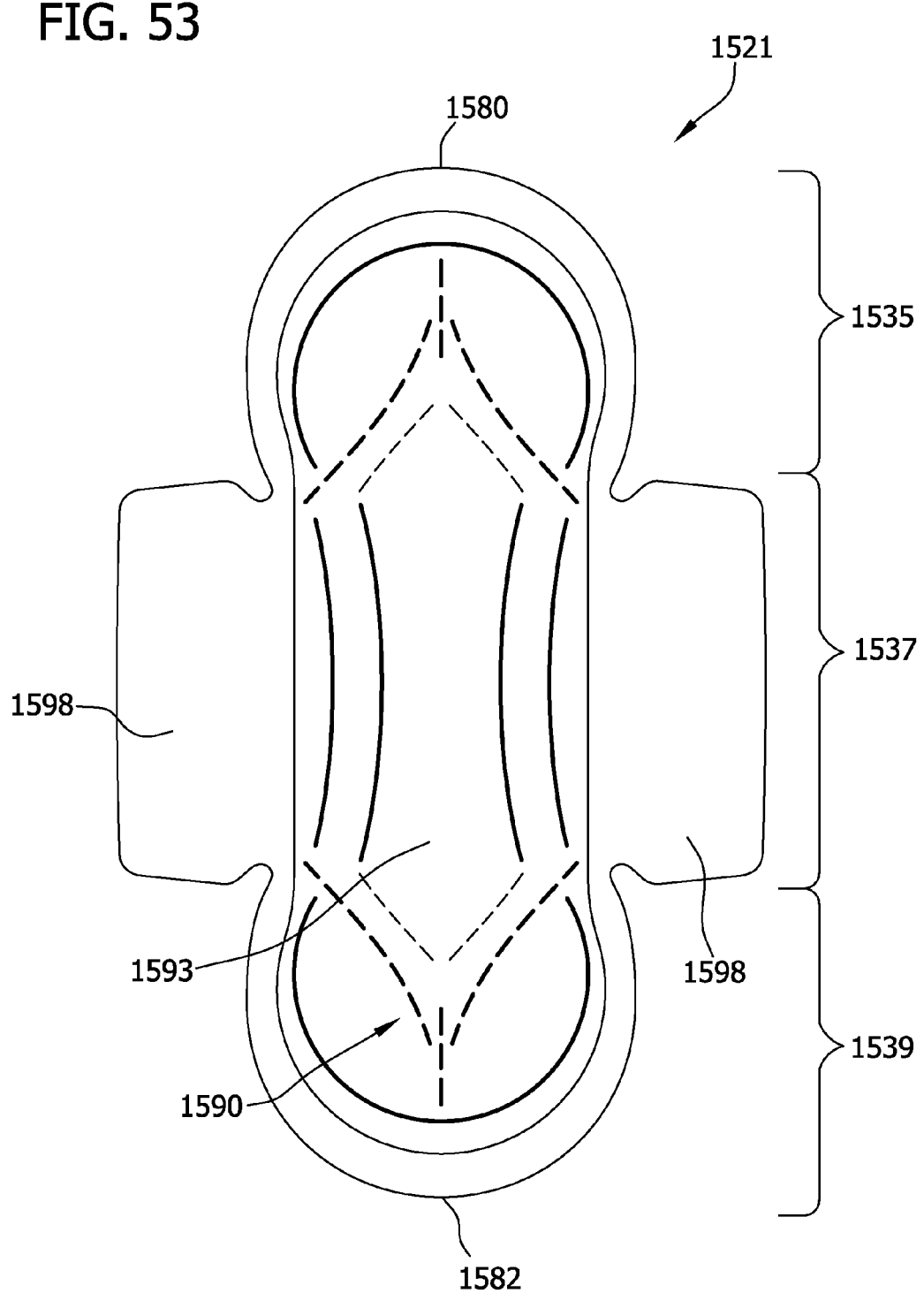
FIG. 53 shows a top view of another embodiment of an absorbent structure having wings.

FIG. 53 illustrates another embodiment of an absorbent structure 1521 having an upper portion 1535, a middle portion 1537, and a lower portion 1539. The absorbent structure 1521 also includes generally semi-circular upper and lower edges 1580, 1582. The middle portion 1537 of the absorbent structure 1521 includes a pair of opposed wings 1598 extending outward from the structure and that can be wrapped and secured around the undergarment of the wearer to help hold the structure in place. The wings 1598 can include a garment adhesive for adhering the wings to the wearer's undergarment. The absorbent structure 1521 has lines of weakness, indicated generally at 1590, to facilitate folding of the absorbent structure in one of the lower or upper portions 1537, 1539 and to define a relief for inhibiting folding of the absorbent structure in at least a central region 1593 of the middle portion 1537 during wear.

Although the present invention has been described with reference to various embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A feminine care absorbent article having a longitudinal axis and a transverse axis, the article comprising an absorbent structure configured for disposition adjacent a female wearer's vaginal region to absorb bodily fluids discharged by the wearer, the absorbent structure having end portions and a middle portion located between the end portions, the absorbent structure having a pair of lines of weakness disposed in one of the end portions and configured to facilitate folding of the absorbent structure in a longitudinal direction in response to a lateral compressive force, the pair of lines of weakness diverging from each other as the pair of lines of weakness extends from said one of the end portions toward the middle portion of the absorbent structure, the absorbent structure having a relief for inhibiting the longitudinal folding of the absorbent structure facilitated by the at least one line of weakness from extending beyond the middle portion of the absorbent structure.

2. The feminine care absorbent article of claim 1 wherein the end portions comprise an upper end portion and a lower end portion, the middle portion being located between the upper and lower end portions, the pair of lines of weakness being disposed in the lower end portion and configured to facilitate placement of the lower end portion within the wearer's gluteal cleft.

3. The feminine care absorbent article of claim 1 wherein pair of lines of weakness are formed by embossing lines that are defined by a plurality of discrete embossing elements.

4. The feminine care absorbent article of claim 1 further comprising a pair of opposed wings extending outward from middle portion.

5. The feminine care absorbent article of claim 1 further comprising a shell for supporting the absorbent structure at the vaginal region, the shell having a body-facing surface and a garment-facing surface, the body-facing surface having an adhesive thereon for adhering the shell directly to the wearer.

6. A feminine care absorbent article having a longitudinal axis and a transverse axis, the article comprising an absorbent structure configured for disposition adjacent a female wearer's vaginal region to absorb bodily fluids discharged by the wearer, the absorbent structure having an upper end portion, a lower end portion and a middle portion located between the end portions, both of the upper and lower end portions of the absorbent structure including a line of weakness configured to facilitate folding of the absorbent structure in a longitudinal direction in response to a lateral compressive force, wherein the line of weakness in the upper end portion of the absorbent structure is generally symmetric with respect to the line of weakness in the lower end portion, the absorbent structure having a relief for inhibiting the longitudinal folding of the absorbent structure facilitated by at least one of the lines of weakness from extending beyond the middle portion of the absorbent structure.

7. The feminine care absorbent article of claim 6 wherein the relief for inhibiting the longitudinal folding of the absorbent structure comprises a first relief, the first relief being configured to inhibit the longitudinal folding of the absorbent structure facilitated by the line of weakness in the upper portion from extending beyond the middle portion of the absorbent structure.

8. The feminine care absorbent article of claim 7 further comprising a second relief, the second relief being configured to inhibit the longitudinal folding of the absorbent structure facilitated by the line of weakness in the lower portion from extending beyond the middle portion of the absorbent structure.

9. The feminine care absorbent article of claim 6 further comprising a shell for supporting the absorbent structure at the vaginal region, the shell having a body-facing surface and a garment-facing surface, the body-facing surface having an adhesive thereon for adhering the shell directly to the wearer.

10. A feminine care absorbent article having a longitudinal axis and a transverse axis, the article comprising an absorbent structure configured for disposition adjacent a female wearer's vaginal region to absorb bodily fluids discharged by the wearer, the absorbent structure having an upper portion, a middle portion, and a lower portion, the absorbent structure having a first line of weakness disposed in the lower portion and configured for folding the absorbent structure in a longitudinal direction in response to a compressive force, the absorbent structure having a generally V-shaped second line of weakness disposed in the upper portion and being configured to resist folding of the absorbent structure in the upper portion of the absorbent structure, wherein the line of weakness in the upper end portion of the absorbent structure is generally symmetric with respect to the line of weakness in the lower end portion.

11. The feminine care absorbent article of claim 10 wherein the lower portion of the absorbent structure is configurable from a generally flat configuration to a raised wear configuration.

12. The feminine care absorbent article of claim 11 wherein the wear configuration, the lower portion of the absorbent structure includes a peak and sloping sidewalls extending downward from the peak.

13. The feminine care absorbent article of claim 12 wherein the wear configuration, the lower portion includes flanking portions extending outward from the sloping sidewalls.

14. The feminine care absorbent article of claim 10 further comprising a shell for supporting the absorbent structure at said vaginal region, the shell having a body-facing surface and a garment-facing surface, the body-facing surface having an adhesive thereon for adhering the shell directly to the wearer.

15. A feminine care absorbent article having a longitudinal axis and a transverse axis, the article comprising an absorbent structure configured for disposition adjacent a female wearer's vaginal region to absorb bodily fluids discharged by the wearer, the absorbent structure having an upper portion, a middle portion, and a lower portion, the lower portion having a first line of weakness configured for longitudinally folding the absorbent structure in response to a lateral compressive force, the absorbent structure having a second line of weakness defining a relief for inhibiting the longitudinally folding the absorbent structure facilitated by the first line of weakness from extending into the middle portion of the absorbent structure, the second line of weakness including an arcuate portion for facilitating transverse folding of the absorbent article, wherein the absorbent structure comprises an absorbent core and a top sheet overlying the absorbent core, at least one of the first line of weakness and the second line of weakness being defined by embossing lines formed in the top sheet and cuts formed in the absorbent core.

16. The feminine care absorbent article of claim 15 wherein the embossing lines formed in the top sheet are aligned with the cuts formed in the absorbent core.

17. The feminine care absorbent article of claim 15 wherein the absorbent structure further comprises a backsheet, the backsheet being free of the line of weakness.

18. The feminine care absorbent article of claim 15 further comprising a shell for supporting the absorbent structure at said vaginal region, the shell having a body-facing surface and a garment-facing surface, the body-facing surface having an adhesive thereon for adhering the shell directly to the wearer.

\* \* \* \* \*